United States Patent [19]
Ehrlich et al.

[11] Patent Number: 5,643,779
[45] Date of Patent: Jul. 1, 1997

[54] NUCLEIC ACID CODING FOR AN α-ACETOLACTATE SYNTHASE FROM LACTOCOCCUS AND ITS APPLICATIONS

[75] Inventors: Stanislav Ehrlich, Paris; Jean-Jacques Godon, Saint Pierre-de-Nemours; Pierre Renault, Montigny-le-Bretonneux, all of France

[73] Assignee: Biotechnology and Biological Sciences Research Council, Great Britain

[21] Appl. No.: 403,866

[22] PCT Filed: Sep. 27, 1993

[86] PCT No.: PCT/GB93/02012

§ 371 Date: Jul. 21, 1995

§ 102(e) Date: Jul. 21, 1995

[87] PCT Pub. No.: WO94/08020

PCT Pub. Date: Apr. 14, 1994

[30] Foreign Application Priority Data

Sep. 25, 1992 [FR] France .................................. 92 11470

[51] Int. Cl.⁶ ..................................................... C12N 9/88
[52] U.S. Cl. ......................... 435/232; 435/74; 435/252.3; 435/252.33; 435/252.8; 435/252.9; 435/320.1
[58] Field of Search ................................. 435/74, 252.3, 435/252.32, 252.9, 253.4, 885, 320.1, 172.3, 172.1, 183, 232

[56] References Cited

U.S. PATENT DOCUMENTS 5,420,021  5/1995  Marugg et al. ........................ 435/74

FOREIGN PATENT DOCUMENTS 0 436 886 A1  12/1990  European Pat. Off. .
0 500 188 A2  2/1992  European Pat. Off. .

OTHER PUBLICATIONS

Starrenburg et al., "Citrate Fermentation by Lactococcus and Leuconostoc spp.," *Applied and Environmental Microbiology*, 57(12):3535–3540 (Dec. 1991).

Snoep et al., "Isolation, Characterization, and Physiological Role of the Pyruvate Dehydrogenase Complex and α–Acetolactate Synthase of Lactococcus lactis subsp. lactis bv. diacetylactis," *Journal of Bacteriology*, 174(14):4838–4841 (Jul. 1992).

Zahler et al., "α–Acetolactate Synthesis by *Bacillus subtilis*," *Biosynth. Branched Chain Amino Acids, Proc. Workshop* 1988, pp. 25–32 (1990).

Godon et al. "Branched–Chain Amino Acid Biosynth. Gene in . . . " J. Bacteriol. 174, 6580–6589. Oct. 1992.

Hugenholtz et al. "Diacetyl production by different . . . " Appl. Microbiol. Biotechnol. 38, 17–22. 1992.

*Primary Examiner*—Robert A. Wax
*Assistant Examiner*—Nashaat T. Nashed
*Attorney, Agent, or Firm*—Nixon, Hargrave, Devans & Doyle

[57] ABSTRACT

The nucleic acid coding for an α-acetolactate synthase from Lactococcus is provided, as well as vectors containing this nucleic acid and the use of these vectors for transforming microorganisms in which the production of α-acetolactate will be promoted, The nucleic acid comprises one or the other or both of a first segment corresponding to the ilvB gene (which encodes one subunit of α-acetolactate synthase of *Lactococcus lactis* subsp. *lactis*) and a second segment corresponding to the ilvN gene (which encodes a second subunit of α-acetolactate synthase of *Lactococcus lactis* subsp. *lactis*).

17 Claims, 10 Drawing Sheets

```
PROTEINE  RESIDU         SEQUENCE CONSERVEE

ORF2       36   ILKDITWKVNPGENWVILGLNGSGKSSLLKLILAEEWKTSGEITVLNTQF---RNGEIPKLRKRISVVGSFIAERFQPNIKA
Nod1¹      27   VVNDLSFTIAAGRCFGLLGPNGAGKSTITRMILGMTSPSVGKITV----LGAQEPGQVRLARAKIGIVSQPDNLDL--EFTV
MalK²      18   VSKDINLDIHEGEFVVFVGPSGCGKSTLLRMIAGLETITSGDLFIGEKRMDTPPAE------R-GVGMVTQSYALYPHLSV
GlnQ³      16   VLHNIDLNIAQGRVVIIGPSGSGKSTLLRCINKLEEITSGDLIVDGLKVND-PKVDERLIRQE-A-GMVTQQFYLFPHLTA
ProV⁴      43   GVKDASLAIEEGEIFVIMGLSGSGKSTMVRLLNRLIEPTRGQVLIDGVDIAKISDAELREVRRK-KIAMVTQSFALMPHMTV
HlyB⁵     484   ILDNINLSIKQGEVIGIVGRSGSGKSTLTKLIQRFYIPENGQVLIDGHDLALADPNWLR--RQ---VGVVLQDNVLLNRSII
CyaB⁶     487   ALRNVSLRIAPGEVVGVVGRSGSGKSTLTRLIQRMFVADRGRVLIDGHDIGIVDSASLR--RQ---LGVVLQESTLFNRSVR
                      .     .   *  * ***         ..          .                     * **.      .
                                         ——————————
                                            NB1

ORF2      115   ENLVYTGKFNSSMLYKPYTDQELDEARQLLRQM--GAKSLIGRNYASLSQGEKQVLLIARSLILKPELLILDEATNGLDLFA
Nod1      103   RENLLV--YGRYFRMSTR--EIETVIPSLLEFA--RLESKANTRVADLSGGMKRRLTLAGALINDPQLLILDEPTTGLDPHA
MalK       95   AENM-S--FG-LKPAGAKKEVINQRVNQVAEVL--QLAHLLDRKPKALSGGQRQRVAIGRTLVAEPSVFLLDEPLSNLDAAL
GlnQ       94   LENV-M--FGPLRVRGANKEEAEKLARELLAKV--GLAERAHHYPSELSGGQQQRVAIARALAVKPKMLFDEPTSALDPEL
ProV      124   LDNT-A--FG-MELAGINAEERREKALDALRQV--GLENYAHSYPDELSGGMRQRVGLARALAINPDILLMDEAF9ALDPLI
HlyB      561   DNISLA--NPGMSVEKVIYAAKLAGAHDFISELREGYNTIVGEQGAGLSGGQRQRIAIARALVNNPKILIFDEATSALDYES
CyaB      564   DNIALT--RPGASMHEVVAAARLAGAHEFICQLPEGYDTMLGENGVGLSGGQRQRIGIARALIHRPRVLILDEATSALDYES
                                                  .               ————————
                                                                    NB2

ORF2      193   KEKLLKQLQQINQLKTAPTLIYISHHPDVITDIFTHLLLREGKVIQSGKKENLLNEKILTDFYQ    (259)
Nod1      181   RHLIWERLRSLLA-R-GKTILLTTHIMEEAERLCDRLCVLEAGRKIAEGRPHALIEEQIGCPVIE   (237)
MalK      169   RVQMRIEISRLHK-RLGRTMIYVTHDQVEAMTLADKIVVLDAGRVAQVGKPLAV-PLSGRPFCRR   (228)
GlnQ      172   RHEVLKVMQDL-A-EEGMTMVIVTHEIGFAEKVASRLFIDKGRIAEDGNPQVLIKNPPSQRLQE    (240)
ProV      200   RTEMQDELVKLQA-KHQRTIVFISHDLDEAMRIGDRIAIMQNGEVVQGTPDEILNNPANDYVRT    (400)
HlyB      641   EHVIMRNMHKICK---GRTVIIAHRLS-TVKNADRIIVMEKGKIVEQGKHKELLSEPESLYSYL    (707)
CyaB      644   EHIIQRNMRDICD---GRTVIIAHRLS-AVRCADRIVVMEGGEVAECGSHETLAAGG-LYARL    (712)
                                 *                                .
```

NUCLEIC ACID CODING FOR AN α-ACETOLACTATE SYNTHASE FROM LACTOCOCCUS AND ITS APPLICATIONS

This application is the U.S. national stage application of PCT International Application No. PCT/GB93/02012, filed 27 Sep. 1993, which claims priority of French Patent Application 92/11470, filed 25 September 1992.

The invention relates to a nucleic acid coding for an α-acetolactate synthase, as well as to vectors containing this nucleic acid and to the use of these vectors for transforming microorganisms in which the production of α-acetolactate and diacetyl will be promoted.

Diacetyl is a flavouring sought in the production of food products such as butter, crème fraîche and some cheeses. Conversely, this flavouring is undesirable in the production of other food products such as beer.

A limited number of bacteria, such as *Lactococcus lactis* subsp. *lactis* biovar *diacetylactis* as well as bacteria of the genera *Leuconostoc, Pediococcus, Lactobacillus*, naturally produce diacetyl; this production takes place from a substrate present in milk in small amounts, citrate; these bacterial strains are capable of metabolizing citrate to pyruvate, which is then converted to acetoin and to diacetyl.

α-Acetolactate is also an intermediate of the pathway of synthesis of the branched amino acids, which are leucine, isoleucine and valine. This pathway has been very widely studied in bacteria, fungi and plants (1, 2, 3, 4). However, the sequences of the assembly of genes involved in this pathway in one and the same microorganism have never been reported.

The regulation of the expression of the genes involved in the pathway of synthesis of the branched amino acids is complex on account of the steps common to the synthesis of these three amino acids, and this pathway is often presented as a model for the study of organization and regulation.

The organization of these genes has been characterized in *Escherichia coli* (3), *Salmonella typhimurium* (3), *Bacillus subtilis* (5, 6, 7), *Corynebacterium typhimurium* (8) and *Staphylococcus aureus* (9).

On the *E. coli* chromosome, the genes are localized in three groups (10). The largest, located at 85 minutes, is organized in one large transcription unit and two small transcription units, comprising the ilvGMEDA, ilvY and ilvC genes, respectively (11, 12); another group, located at 2 minutes, is composed of two transcription units comprising the ilvH and leuACBD genes (13, 14), and the last group, at 82 min, groups together the ilvBN genes in a single transcription unit.

A similar organization is found in other Enterobacteriaceae.

In *B. subtilis*, the ilvBN and leuACBD genes are encountered in one region of the chromosome (5) and the ilvAD genes in another region.

Three cloned nonadjacent chromosomal fragments of *C. glutamicum* carry five genes of the pathway of synthesis of the branched amino acids, ilvCBN, ilvA and ilvE (9).

In *S. aureus*, genetic mapping shows that eight genes are grouped together in the following order: ilvAB-CD, leuABCD.

The synthesis of the branched amino acids leucine, isoleucine and valine in *L. lactis* subsp. *lactis* is a complex pathway involving eight enzymes, four of which are common to the synthesis of the above three amino acids. The synthesis of valine involves only these four, whereas the synthesis of isoleucine and of leucine involves, respectively, one and four additional specific enzymes. In addition, this system is complicated by the fact that the excess of one of the three amino acids interferes in the synthesis of the other amino acids.

The present invention relates to the cloning, characterization and sequencing of the genes involved in the pathway of synthesis of the branched amino acids in *L. lactis* subsp. *lactis*. This work was carried out using the strain NCDO2118 (AFRC, Institute of Food Research Reading Laboratory, Shinfield, Reading, Berks, United Kingdom). The genes were characterized by cloning, complementation in *E. coli* and *B. subtilis* and sequence analysis. Nine structural genes are assembled on a 12-kb DNA fragment in the following order: leuABCDilvDBNCA.

Among these genes, the invention relates to nucleic acid sequence coding for two polypeptides forming the subunits of a protein possessing α-acetolactate synthase activity; this enzyme is of very special interest since it is responsible, in *L. lactis* subsp. *lactis*, for the direct conversion of pyruvate to α-acetolactate independently of the presence of citrate in the medium.

The techniques used for cloning and sequencing the nucleic acid of the invention will be described more particularly in the detailed description of the invention.

Reference will be made in what follows to the tables and figures, wherein:

Table I shows the bacterial strains, plasmids and phages used for cloning the *L. lactis* subsp. *lactis* genes involved in the pathway of synthesis of the branched amino acids;

Table II shows a comparison of proteins involved in the pathway of synthesis of the branched amino acids between *L. lactis* subsp. *lactis* and different microorganisms;

FIG. 1 shows the structure of the region of *L. lactis* subsp. *lactis* DNA carrying the genes involved in the pathway of synthesis of the branched amino acids;

FIGS. 2A–2F show the nucleotide sequence, together with the polypeptide sequence deduced from this nucleotide sequence, of the region of *L. lactis* subsp. *lactis* strain NCDO2118 DNA carrying the genes involved in the pathway of synthesis of the branched amino acids; nucleotides 8018 to 9742 of SEQ ID NO: 11 represent the ilvB gene (SEQ ID NO: 12) and encode 575 amino acids as shown (SEQ ID NO: 7); nucleotides 9738 to 10211 of SEQ ID NO: 11 represent the ilvN gene (SEQ ID NO: 13) and encode 158 amino acids as shown (SEQ ID NO: 8);

FIG. 3 shows the alignment of 6 ATP-binding proteins with ORF2 of *L. lactis;*

Figure 1:
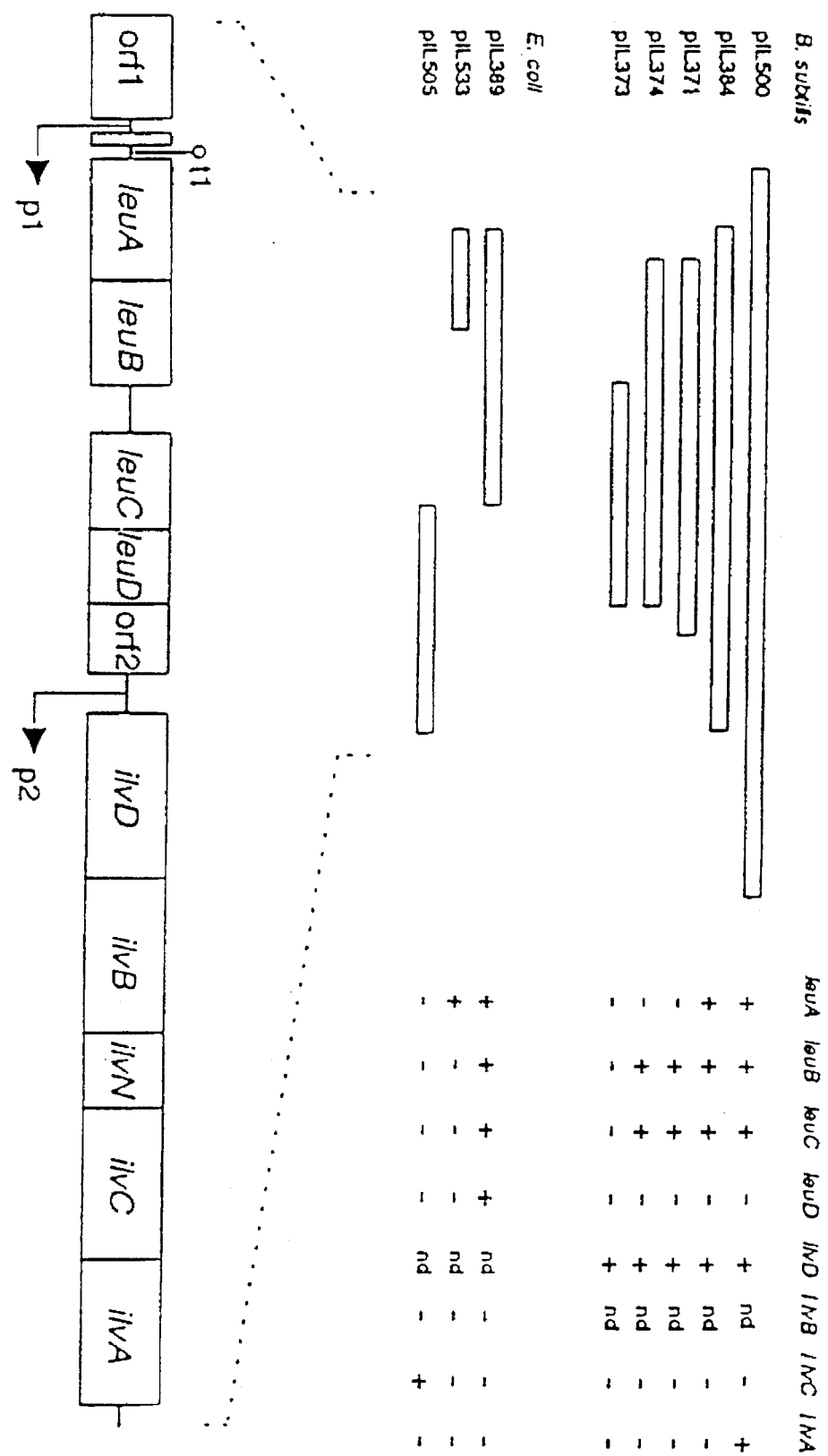
Figure 2A:
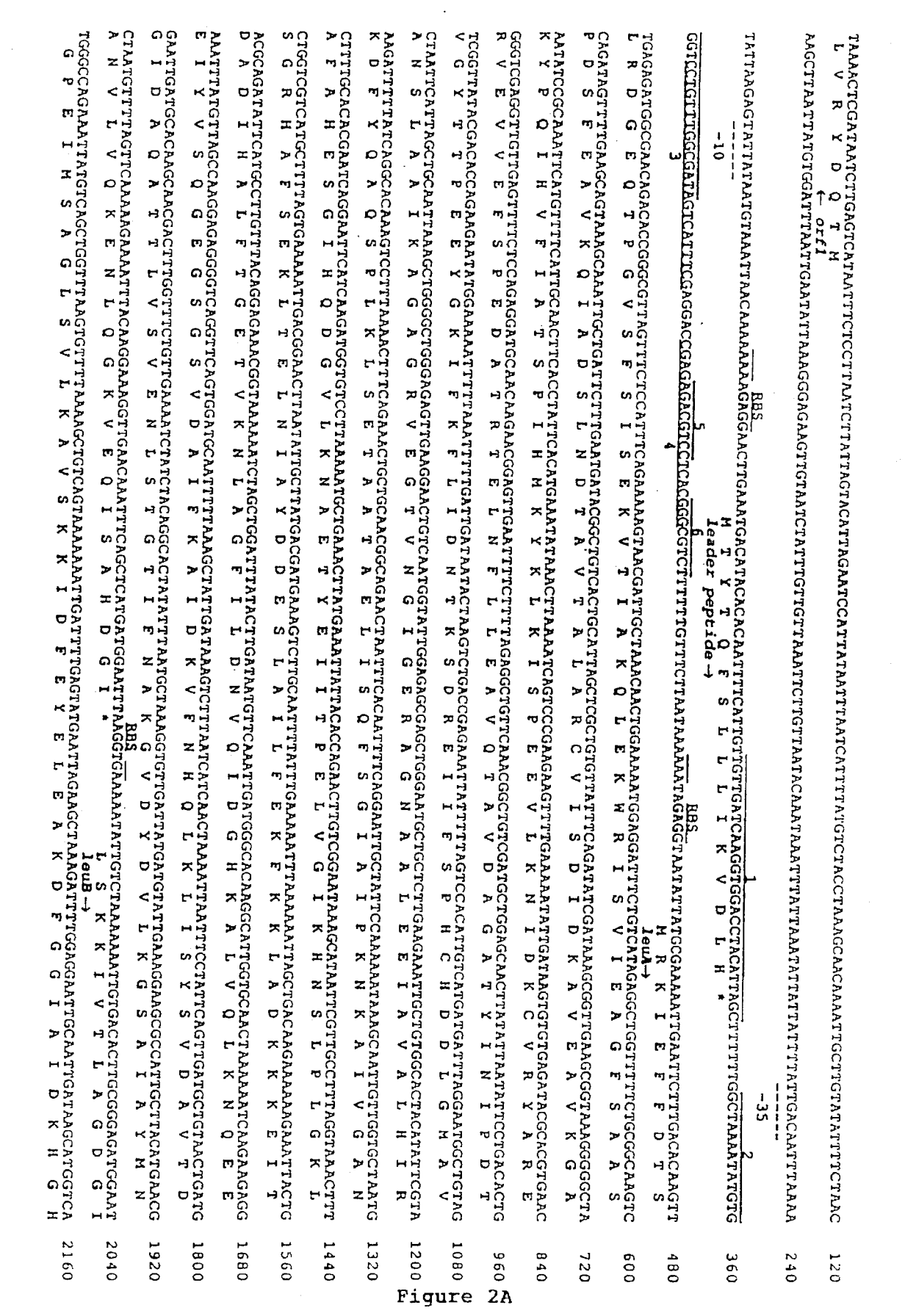
Figure 2B:
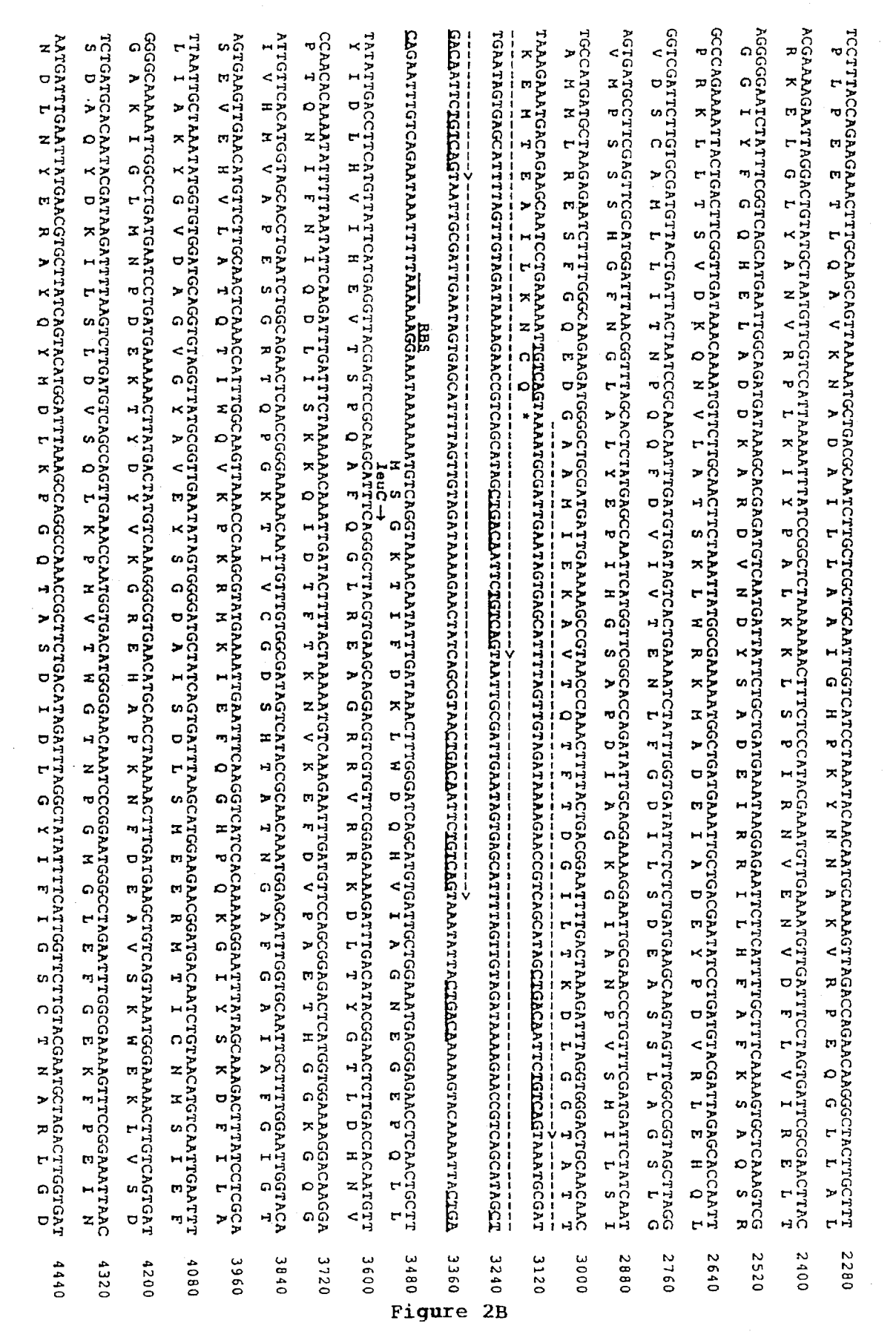
Figure 2C:
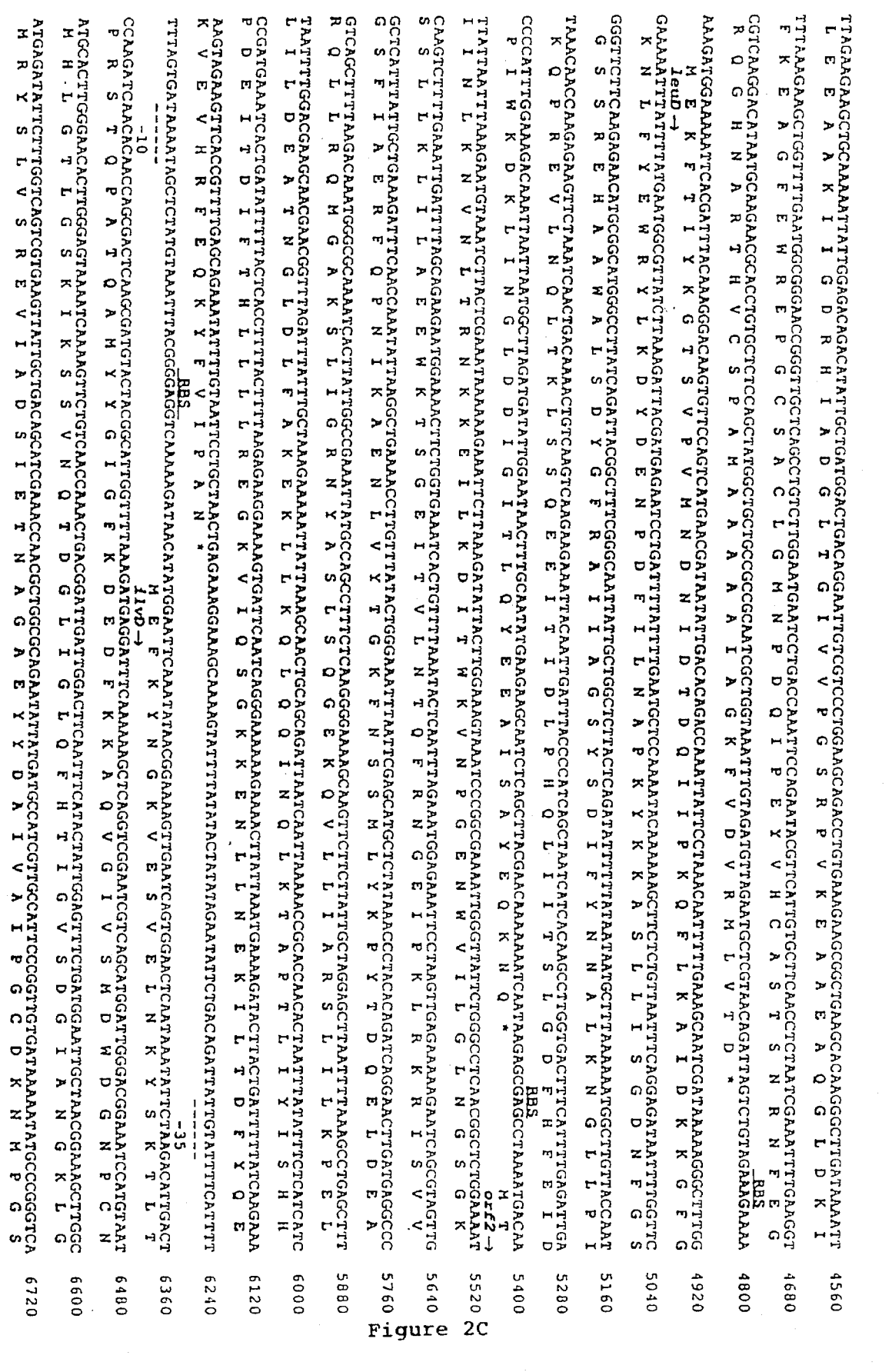
Figure 2D:
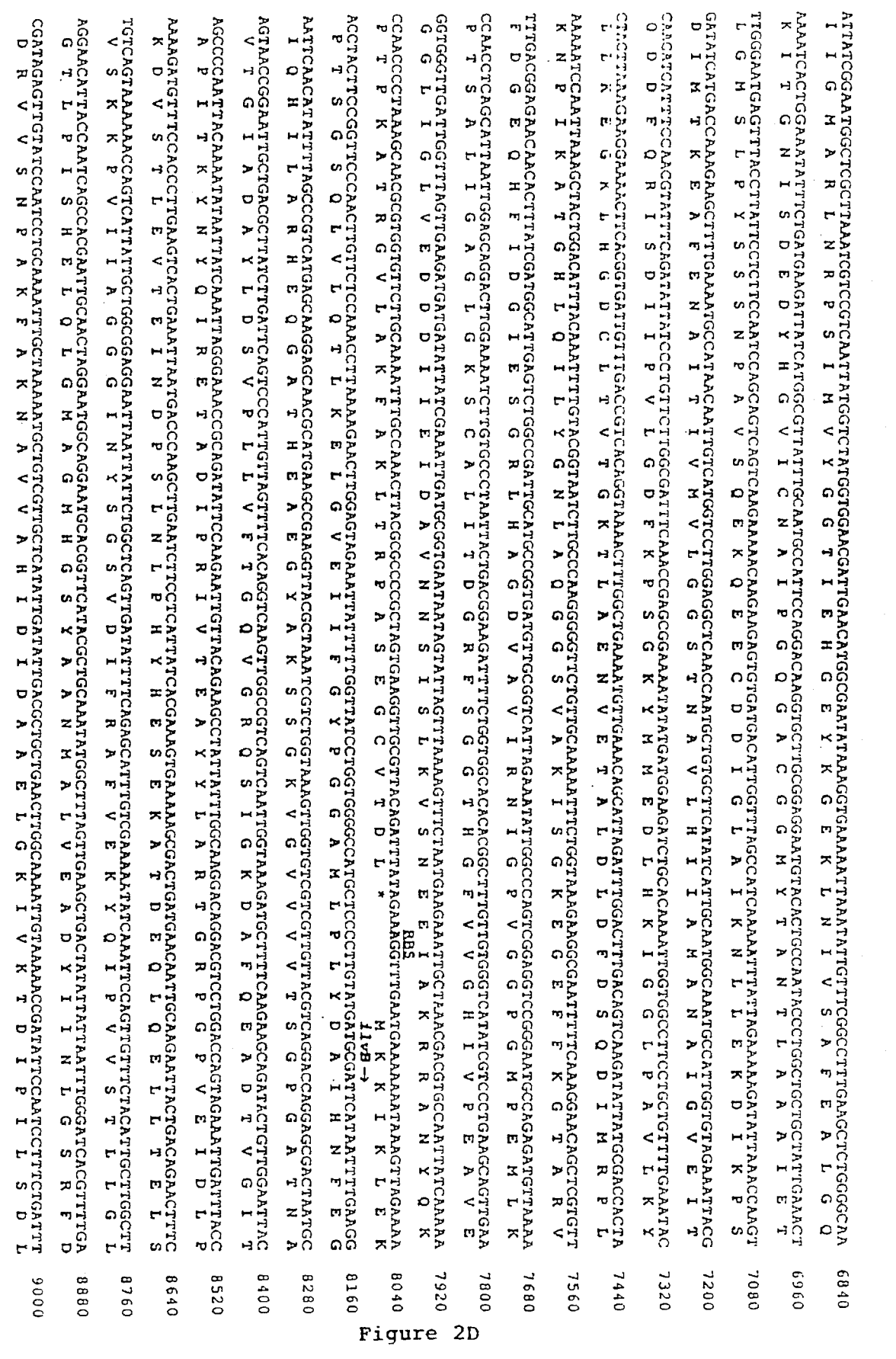
Figure 2E:
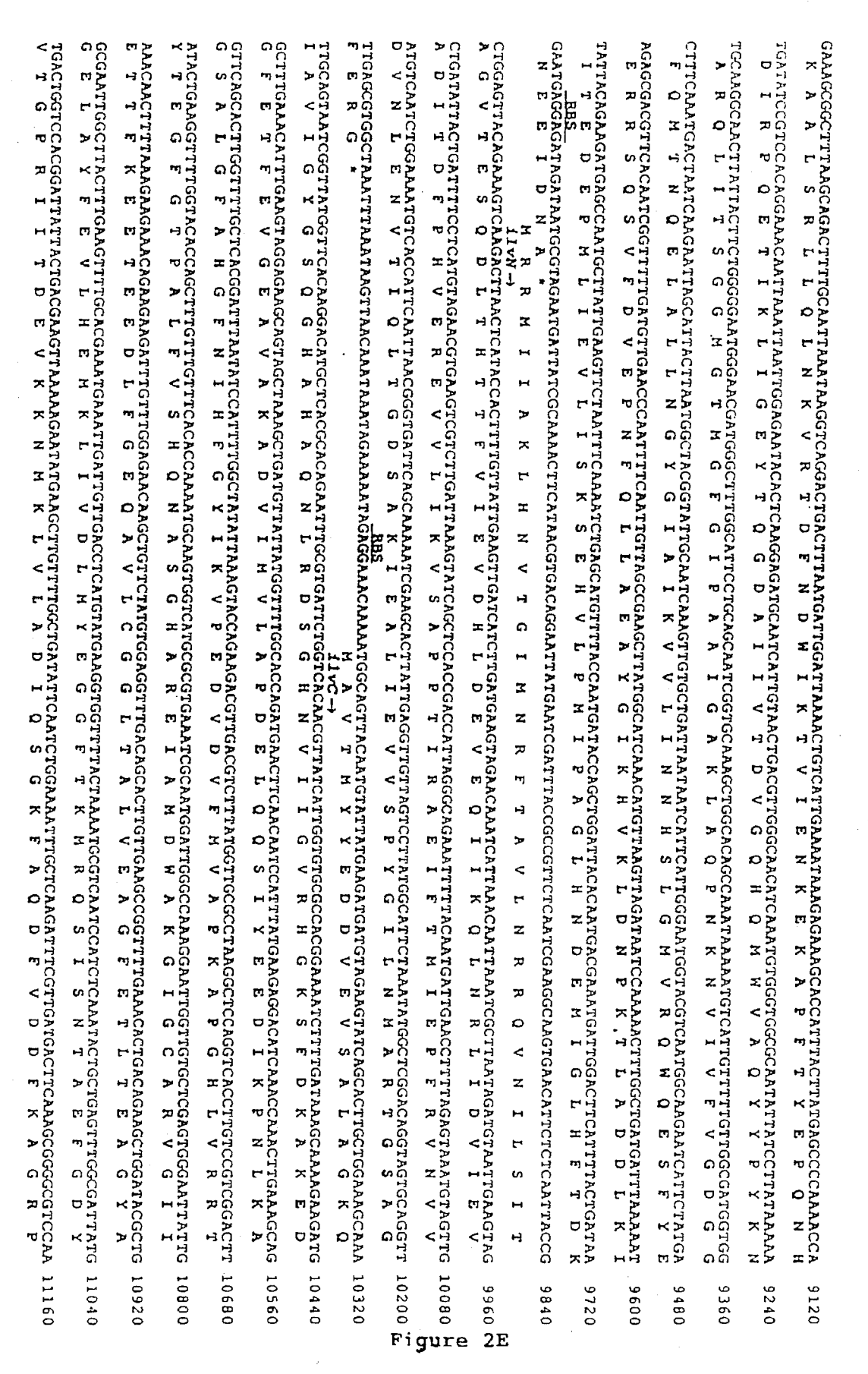
Figure 2F:
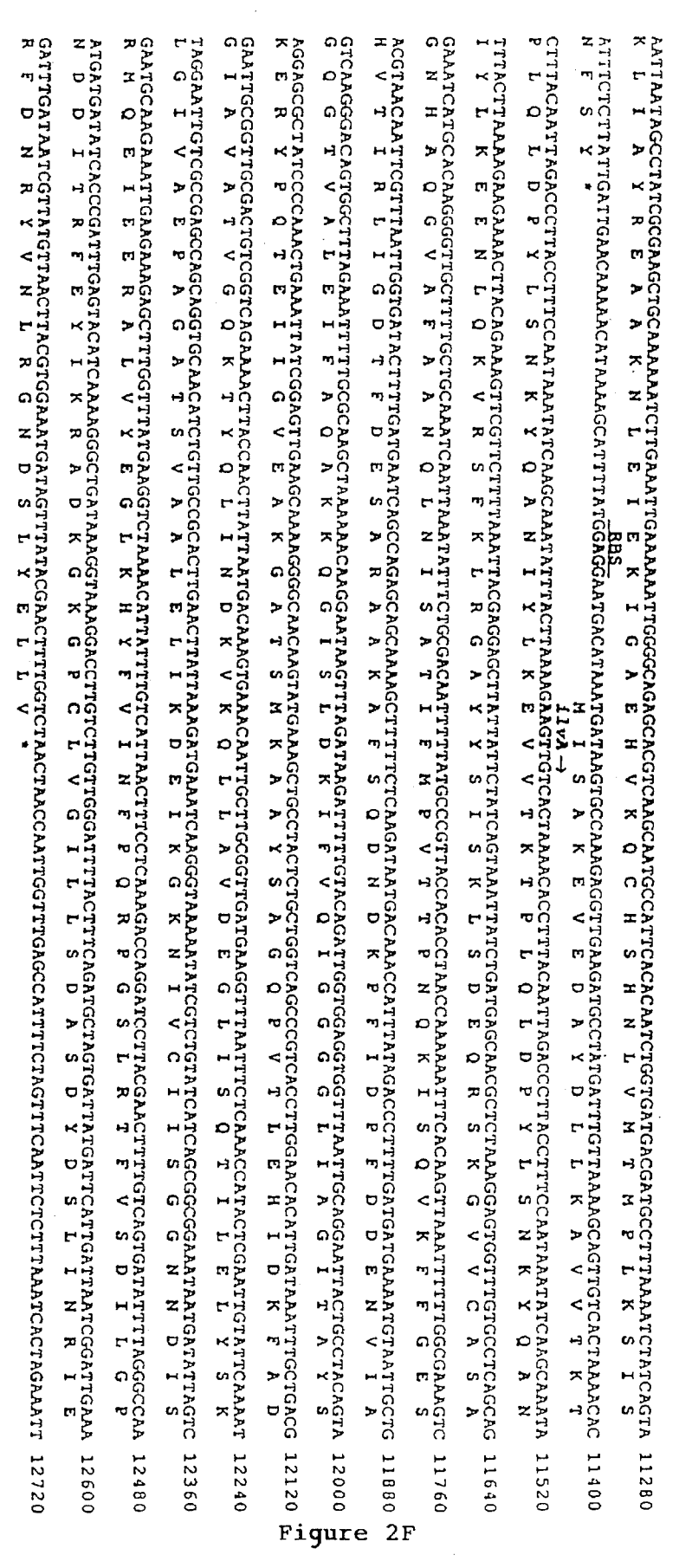

Research work carried out on the DNA of FIG. 2, and also on the polypeptide deduced from this DNA, leads to the following observations:

Ten genes are present in the region of *L. lactis* subsp. *lactis* DNA shown in FIG. 2:

the leuA gene of 1539 nucleotides, located between nucleotides 450 and 1988 of SEQ ID NO: 11 and coding for a polypeptide of 513 amino acids (SEQ ID NO: 1);

the leuB gene of 1041 nucleotides, located between nucleotides 2003 and 3037 of SEQ ID NO: 11 and coding for a polypeptide of 347 amino acids (SEQ ID No: 2 );

the leuC gene of 1380 nucleotides, located between nucleotides 3403 and 4782 of SEQ ID NO: 11 and coding for a polypeptide of 460 amino acids (SEQ ID NO: 3);

the leuD gene of 573 nucleotides, located between nucleotides 4805 and 5377 of SEQ ID NO: 11 and coding for a polypeptide of 191 amino acids (SEQ ID NO: 4);

the orf2 gene of 777 nucleotides, located between nucleotides 5394 and 6170 of SEQ ID NO: 11 and coding for a polypeptide of 259 amino acids (SEQ ID NO: 5);

the ilvD gene of 1710 nucleotides, located between nucleotides 6295 and 8004 of SEQ ID NO: 11 and coding for a polypeptide of 570 amino acids (SEQ ID NO: 6);

the ilvB gene of 1725 nucleotides (SEQ ID NO: 12 which includes the stop codon), located between nucleotides 8018 and 9742 of SEQ ID NO: 11 and coding for a polypeptide of 575 amino acids (SEQ ID NO: 7);

the ilvN gene of 474 nucleotides (SEQ ID NO: 13 which includes the stop codon), located between nucleotides 9738 and 10211 of SEQ ID NO: 11 and coding for a polypeptide of 158 amino acids (SEQ ID NO: 8);

the ilvC gene of 1032 nucleotides, located between nucleotides 10260 and 11291 of SEQ ID NO: 11 and coding for a polypeptide of 344 amino acids (SEQ ID NO: 9);

the ilvA gene of 1323 nucleotides, located between nucleotides 11337 and 12659 of SEQ ID NO: 11 and coding for a polypeptide of 441 amino acids (SEQ ID NO: 10).

The invention relates to any nucleic acid comprising all or part of the DNA sequence bounded by the nucleotides located at positions 8018 and 10211 of SEQ ID NO: 11 and as shown in FIG. 2, and coding for one or both subunits of a protein capable of converting pyruvate to α-acetolactate; and for any other novel polynucleotide, peptide or protein disclosed herein.

α-Acetolactate synthase of *L. lactis* subsp. *lactis* is a protein consisting of two subunits; the first subunit is a polypeptide of 575 amino acids (SEQ ID NO: 7) encoded by the fragment bounded by the nucleotides located at positions 8018 and 9742 of SEQ ID NO: 11 and as shown in FIG. 2, and corresponding to the ilvB gene (SEQ ID NO: 12); the second subunit is a polypeptide of 158 amino acids (SEQ ID NO: 8) encoded by the fragment bounded by the nucleotides located at positions 9738 and 10211 of SEQ ID NO: 11 and as shown in FIG. 2, and corresponding to the ilvN gene (SEQ ID NO: 15). Consequently, the α-acetolactate synthase activity of *L. lactis* subsp. *lactis* is possible only if both of these genes are expressed.

The subject of the invention is, more especially, the fragments of the above nucleic acid coding for one or both subunits of a protein capable of possessing the enzymatic properties of α-acetolactate synthase of *L. lactis* subsp. *lactis*. More specifically, the invention relates to nucleic acids comprising one or other or both of the following segments:

the first segment corresponding to the ilvB gene (SEQ ID NO: 12), bounded by the nucleotides located at positions 8018 and 9742 of SEQ ID NO: 11 and as shown in FIG. 2, and coding for the polypeptide of 575 amino acids (SEQ ID NO: 7) corresponding to one of the two subunits of α-acetolactate synthase of *L. lactis* subsp. *lactis*;

the second segment corresponding to the ilvN gene (SEQ ID NO: 13), bounded by the nucleotides located at positions 9738 and 10211 of SEQ ID NO: 11 and as shown in FIG. 2, and coding for the polypeptide of 158 amino acids (SEQ ID NO: 8) corresponding to the other subunit of α-acetolactate synthase of *L. lactis* subsp. *lactis*.

The invention also relates to the above nucleic acids in which the sequences are modified, provided the polypeptides encoded by these nucleic acids retain their enzymatic properties of the α-acetolactate synthase type.

Such modifications, without implied limitation, lead, for example, to variant nucleic acids which differ from the nucleic acid of the invention by the addition and/or deletion of one or more nucleotides and/or modification of one or more nucleotides.

Thus, the invention further relates to DNA sequences coding for α-acetolactate synthase of the pathway of synthesis of the branched amino acids of bacteria of the genus *Lactococcus*, such as *L. plantarum*, *L. rafinolactis* and *L. lactis*, for instance *L. lactis* subsp. *cremoris*; which DNA sequences display a strong homology with the nucleic acid sequence of ilvBN (SEQ ID NO: 14).

Advantageously, these DNA sequences are identified, and where appropriate selected, by genetic hybridization with one or more nucleic acid probes originating from the above nucleic acid sequences, under moderately stringent conditions.

As an example, a method for the identification of such a DNA sequence comprises the following steps:

extraction of the DNA from the bacterium;

digestion of this DNA with one or more restriction enzymes such as EcoRI;

transfer of the DNA fragments obtained onto a nitrocellulose membrane;

hybridization with the complete ilvBN sequence in a hybridization solution whose composition is: 6×SSC, approximately 10% formamide, 5×Denhardt, 100 ml of phosphate buffer pH 7.

The invention also relates to polypeptide sequences comprising all or part of the polypeptide sequences encoded, on the one hand by the DNA sequence bounded by the nucleotides located at positions 8018 and 9742 of SEQ ID NO: 11 and as shown in FIG. 2, and on the other hand by the DNA sequence bounded by the nucleotides located at positions 9738 and 10211 of SEQ ID NO: 11 and as shown in FIG. 2; these two polypeptides constituting the subunits of a protein possessing the enzymatic properties of α-acetolactate synthase of *L. lactis* subsp. *lactis*.

The subject of the invention is also any polypeptide sequence originating from each of the above polypeptide sequences, provided the protein formed from these polypeptides possesses enzymatic properties of the type possessed by α-acetolactate synthase.

The above polypeptides may be modified provided they retain the enzymatic properties defined above. For example, without implied limitation, polypeptides lying within the scope of the invention can differ from those defined above by the addition and/or deletion of one or more amino acids and/or modification of one or more amino acids.

A person skilled in the art has at his disposal means enabling him to identify those polypeptides of shorter sequences which lie within the field of the invention. A general means enabling him to undertake this identification consists in treating each of the above polypeptides with a protease that cleaves the polypeptides at a specific site, and then separating the fragments obtained and testing them for their enzymatic activity with respect to pyruvate.

Another means enabling regions of the polypeptides which are essential to the α-acetolactate synthase activity to be identified consists in cleaving the nucleic acids corresponding to the ilvB and ilvN genes, for example using one or more restriction enzymes, before introducing them into the cell host or the expression vector used for the production of a protein displaying α-acetolactate synthase activity. The truncated nucleic acid may thus be tested for its capacity to express effectively a product possessing α-acetolactate synthase activity or, on the contrary, no longer possessing it.

The subject of the invention is also any recombinant nucleic acid comprising at least one nucleotide sequence of the abovementioned type coding for α-acetolactate synthase, combined with at least one promoter and/or one transcription terminator recognized by the polymerases of the host into which the said recombinant nucleic acid is introduced.

The introduction of the recombinant nucleic acid may be carried out using vectors of the plasmid type capable of replicating in the host microorganism and of permitting the expression therein of the sequence coding for the enzyme, or alternatively the recombinant nucleic acid may be introduced directly into the genome by genetic engineering techniques known to a person skilled in the art.

The host microorganisms into which the recombinant nucleic acid is capable of being introduced are preferably prokaryotic cells such as *Lactococcus lactis, Leuconostoc lactis, Lactobacillus lactis, Lactobacillus plantarum*, but may also be eukaryotes such as yeasts.

More especially, the invention relates to all microorganisms capable of being used as leaven in an agri-foodstuffs process, in which microorganisms the recombinant nucleic acid of the invention is introduced for the purpose of obtaining an overproduction of diacetyl in an agri-foodstuffs product such as dairy product derivatives, fermented wheys, soft white cheeses, and the like.

Advantageously, the introduction of the recombinant nucleic acid of the invention into *L. lactis* bacteria is combined with an inhibition of the enzyme responsible in these bacteria for the conversion of acetolactate to acetoin (α-acetolactate decarboxylase) and/or of the enzyme involved in the conversion of pyruvate to lactate (lactate dehydrogenase), in order to increase the acetolactate pool leading to diacetyl.

The inhibition of these enzymes may be achieved by all chemical or biological means that enable the metabolic flux towards diacetyl production to be increased; a first biological means consists in deleting all or part of the wild-type genes coding or these enzymes; a second biological means consists in replacing the wild-type genes coding for these enzymes by mutated genes incapable of expressing the enzymes in question.

The recombinant nucleic acid of the invention may also be introduced into other microorganisms, such as *Bacillus*, for the production of diacetyl for non-agri-foodstuffs purposes, for example in cosmetology and as an antibacterial.

Other features of the invention will become apparent in the description which follows, which relates on the one hand to the cloning, characterization and sequencing of the region of *L. lactis* subsp. *lactis* DNA carrying the genes involved in the pathway of synthesis of the branched amino acids, and on the other hand to the introduction of a nucleic acid according to the invention, coding for a polypeptide displaying α-acetolactate synthase activity, into a cell host.

I—CLONING OF THE GENES INVOLVED IN THE SYNTHESIS OF AMINO ACIDS IN *L. LACTIS* SUBSP. *LACTIS*

1) Materials and Methods a) Bacterial strains, plasmids and culture media

The bacterial strains, plasmids and phages used for gene cloning are listed in Table I below.

TABLE I

| Strains and plasmids | Characteristics | Bibliographic references or sources |
|---|---|---|
| *L. lactis* subsp. *lactis* | | |
| NCDO2118 | natural isolate | NCDO |
| *B. subtilis* | | |
| CU740 | leuA5 trpC2 (SPβ) | (7) |
| CU741 | leuC7 trpC2 | (7) |
| CU315 | leuD117 trp2 (SPβ) | (15) |
| IL2685 | leuB6 trpC2 ilvA r⁻/m⁻ Cm$^R$ | |
| MT119 | leuB6 trpC2 r⁻/m⁻ | (16) |
| GSY184 | ilvC1 trpC2 | (17) |
| IL3151 | ilvD4 leuB6 r⁻/m⁺ | |
| 1012 | leuA8* metb5 r⁻/m⁺ | (18) |
| GSY276 | ilvD4 trpC2 | (17) |
| *E. coli* | | |
| CU518 | leuA371 | (19) |
| CU514 | leuB401 | (19) |
| CU520 | leuC171 | (19) |
| CU526 | leuD101 | (19) |
| AB1255 | tonA2 lacY1 tsx-5 supE44 gal-6 λ⁻ hisG1 rpsL8 malA1 xyl-7 mtl-2 ilvA201 metB1 | (20) |
| FD1062 | argH1 thi-1 ara-14 ilvI614 ilvH612 λ⁻ glyA18 relA1 spoT1 ilVB619 bglR20 rbs-5::tn5 | |
| JP58 | ilvG468 (ilvG⁺) thi-1 galK2 λ⁻ rpSL704 xyl-5 | (21) |
| TG1 | mtl-1 ilvC7 argE3 thi-1 supE thi D (lac-proAB) hsdD5 F⁺ traD36 proAB lacI zΔ15 | (22) |
| Plasmids | | |
| pIL253 | Em$^R$, 4.9-kb | (23) |
| pHV438 | Hybrid between pBR322, the Cm$^R$ gene of pC194, thyB and the X segments of *B. subtilis* DNA | (42) |
| pIL371 | 9.2 kb Sau3A fragment of the *L. lactis* chromosome in pIL253 | |
| pIL373 | 4.5-kb Sau3A fragment of the *L. lactis* chromosome in pIL253 | |
| pIL374 | 8.5-kb Sau3 fragment of the *L. lactis* chromosome in pIL253 | |
| pIL384 | 13-kb Sau3A fragment of the *L. lactis* chromosome in pIL253 | |
| pIL389 | 7.5-kb left-hand Sau3A fragment of pIL384 in pBS | |
| pIL500 | 18.5-kb XbaI fragment of the *L. lactis* chromosome in pIL253 | |
| pIL505 | 6.5-kb right-hand SmaI-Sau3A fragment of pIL384 in pBS | |
| pIL533 | 2.5-kb left-hand Sau3A-ExoIII fragment of pIL384 | |
| pBluescript | Ap$^R$, M13 ori, pBR322 ori | (Stratagene) |

*L. lactis* subsp. *lactis* strain IL1403 was cultured at 37° C. on M17 medium (25) in which lactose was replaced by glucose. *Escherichia coli* was cultured on Luria-Bertani (LB) medium or in M9 minimum medium (26) at 37° C. *Bacillus subtilis* was cultured on a medium at 37° C., on LB medium or in Spizizen-salt minimum medium supplemented with the appropriate amino acids. If necessary, erythromycin (5 µg/ml for *L. lactis* subsp. *lactis* or 0.3 µg/ml for *B. subtilis*), ampicillin (50 µg/ml for *E. coli*) or tetracycline (10 µg/ml for *E. coli*) is added to the medium.

b) Molecular cloning and DNA manipulation

The plasmids and the chromosomal DNA were prepared according to known techniques of the prior art (26, 27, 28, 29). Transformation of *E. coli* cells was carried out either by a standard $CaCl_2$ procedure (36) or by electroporation (30). Induction of competence and transformation of *B. subtilis* cells were carried out as described by Anagnotopoulos and Spizizen (31), with a few modifications (32). Southern blotting and DNA hybridizations were carried out as described by Maniatis et al. (26). Nucleic acid probes were prepared using [$\alpha$-$^{32}$P]-dCTP and a nick translation kit in accordance with the supplier's recommendation. The other molecular techniques were carried out as described by Maniatis et al. (26).

c) Analysis of the DNA sequence

The *E. coli* clones used for sequencing were obtained by subcloning DNA fragments into plasmids of the pBluescript family and using exonuclease III and mung bean nuclease from the company Stratagene in order to generate a series of clones containing overlapping DNA fragments.

The DNA was then sequenced using the "Taq DyeDeoxy Terminator Cycle Sequencing" kit and the "Sequencer 370A" marketed by the company Applied Biosystems. Nucleotide and polypeptide sequences were analysed with the University of Wisconsin's "BISANCE" and "GCG" softwares. Protein sequences were aligned with a "MUL-TALIN" software (33).

The nucleic acid sequences were determined on both strands. Restrictively, *B. subtills* strains mutated in the ilvA gene were prepared by transforming competent MT119 cells with pHV438 (34) to $Cm^R$. Integration of this plasmid in the chromosome by double crossing-over replaces the ilvA gene by the $Cm^R$ gene (24).

A representative ilvA leuB6 r$^-$/m$^-$Cm$^R$ clone is designated IL2685.

An ilvD4 leuB6 double mutant of *B. subtilis* was constructed by transformation, using GSY276 DNA to transform competent 1012 cells to cells which were prototrophic for methionine. The transformed cells were then tested for their requirements for isoleucine and leucine and for the absence of restriction by titration of the rho phage.

An ilvD4 leuB6 r$^-$/m$^+$ clone was designated IL3151.

2) Gene Cloning

Total DNA of *L. lactis* subsp. *lactis* NCDO2118 was partially digested with the endonuclease Sau3A1. 20 µg of DNA segments of size larger than 10 kb were ligated with 10 µg of DNA of plasmid vector pIL253 cleaved with BamHI, at a final concentration of 500 µg/ml.

The ligated mixture was used to transform competent cells of the mutant *B. subtilis* strain leuB6 ilV4, IL3151 to isoleucin-independent cells. Four transformants were also Em$^R$, and contained 18-, 14.2-, 13.5- or 9.5-kb plasmids designated pIL384, pIL371, pIL374 and pIL373, respectively.

According to a similar experiment, *L. lactis* subsp. *lactis* DNA cleaved with XbaI was cloned into pIL253 using the mutant *B. subtilis* ilvA strain IL2685 as recipient. The transformants were selected on a minimum medium enriched with leucine and tryptophan but lacking isoleucine.

Two Em$^R$ Ile$^+$ clones, containing an apparently identical 23.5-kb plasmid, designated pIL500, were obtained.

3) Complementation Experiments

The cloned DNA segments were used to complement, in *B. subtilis*, leu and ilv mutants, and in *E. coli* after subcloning into pBluescript. The results relating to these studies are reported in FIG. 1.

FIG. 1 shows the structure of the DNA region carrying the genes for the enzymes involved in the pathway of synthesis of the branched amino acids in *L. lactis*. In this figure, the open bars represent the segments used for the complementation experiments in *B. subtilis* and *E. Coli*. These segments are carried by the plasmids indicated in the figure, which were constructed as described in Table I above. The results of the complementation experiments with the mutants listed in Table I are represented by (+) and (−), referring to growth or the absence of growth on the culture medium, lacking the corresponding amino acids. The organization of the DNA region carrying the genes involved in the pathway of synthesis of the branched amino acids (orf1, leuA, leuB, leuC, leuD, orf2, ilvD, ilvB, ilvN, ilvC, ilvA) is also shown at the bottom of FIG. 1; p1 and p2 indicate the transcription promoters and t1 the transcription terminator. The open reading frame between p1 and t1 represents the leader peptide.

In these complementation experiments, the *E. coli* nomenclature has been used; the leuB and leuC genes of *E. coli* correspond to the leuC and leuB genes, respectively, of *B. subtils*, and the three isoenzymes of acetolactate synthase and of acetohydroxide synthase encoded by ilvBN, ilvIH and ilvGN in *E. coli* correspond to a single enzyme encoded by ilvBN in *B. subtilis*. The leuA, leuB, leuC, ilvD and ilvA genes complement the corresponding mutations in *B. subtilis*; the leuA, leuB, leuC, leuD and ilvC genes complement the corresponding mutations in *E. coli*.

These results are sufficient to identify nine genes involved in the pathway of biosynthesis of the branched amino acids in *L. lactis* subsp. *lactis*.

4) Nucleotide Sequences of the Genes

The nucleotide sequence of a region of 12,720 bp was determined. This sequence (SEQ ID NO: 11) is shown in FIG. 2. A computer analysis according to the method of Griskov et al. (35) discloses ten open reading frames (ORF) of size larger than 200 bp. Each ORF is preceded by a ribosome binding site, complementary to the 3' end of rRNA 163 of *L. lactis* subsp. *lactis* (36). All the ORFs begin with the codon ATG, except for the second which begins with the codon TTG; furthermore, four 72-bp repeat units are present between the second and the third ORF.

FIG. 2 shows the nucleotide sequence, and the polypeptide sequence deduced from this nucleotide sequence, of the DNA region coding for the genes involved in the pathway of synthesis of the branched amino acids of *L. lactis* strain NCDO2118; the numbers at the right indicate the position of the oligonucleotides; the names of the genes are indicated at the beginning of each amino acid sequence; the transcription stop codons and also the ribosome binding sites are indicated respectively by (*) and RBS; the consensus sequences "−10" and "−35" of the promoters are underlined; inverted repeat units, which can constitute "preamptors" and "terminators", are numbered (1,2) and (5, 6), respectively, and those capable of forming "antiterminators" are numbered (3 and 5), (see FIG. 4 below); the arrow (→) indicates the 72-bp direct repeat unit, and the bold characters indicate the 6-bp inverted repeat units which it contains.

5) Assignment of the ORFs

The proteins deduced from the ten ORFs were compared with the GENPRO and NBRF protein databases. Significant homologies were identified for ten ORFs; nine of them correspond to the genes involved in the pathway of synthesis of the branched amino acids, as seen in Table II below.

the functions of the different proteins are shown in the following manner:

([1]), nodulation in *Rhizobium leguminosarum* (55);
([2]), maltose transport in *E. coli* (56);
([3]), glutamine transport in *E. coli* (57);
([4]), glycine, betaine and proline transport in *E. coli* (58);

TABLE II

| Microorganism | %[a] of identical amino acids | | | | | | | | | Bibliographic references |
| --- | --- | --- | --- | --- | --- | --- | --- | --- | --- | --- |
| | LeuA | LeuB | LeuC | LeuD | IlvD | IlvB | IlvN | IlvC | IlvA | |
| *E. coli* | —[b] | — | — | 46 | 42 | 42[c] 43[e] 40[R] | <20[d] 37[f] <20[h] | 34 | 36 | (13, 11, 12, 37) (38) (11) |
| *Salmonella tryphenurium* | 41 | — | 49 | — | — | — | — | — | — | (39, 40) |
| *Bacillus subtilis* | — | 53 | — | — | — | — | — | — | 50 | Genbank (41) |
| *Bacillus coagulans* | — | 53 | — | — | — | — | — | — | — | (42) |
| *Thermus aquaticus* | — | 42 | — | — | — | — | — | — | — | (43) |
| *Saccharomyces cerevisiae* | 25 | 46 | 50[i] | 52[j] | — | 41 | — | 33 | 38 | (44, 45, 46, 47, 48, 49) |
| *Phycomyces blakesleeanus* | — | — | 50[i] | 49[j] | — | — | — | — | — | (50) |
| *Mucor circinelloides* | — | — | 49 | — | — | — | — | — | — | (51) |

In Table II:
[a]indicates that the percentage was calculated using a software (52) from the percentage identity by the size of the smallest protein;
[b]indicates sequences not available;
[c]indicates the comparison with IlvB nucleic acid;
[d]indicates the comparison with IlvN nucleic acid;
[e]indicates the comparison with IlvI nucleic acid;
[f]indicates the comparison with IlvH nucleic acid;
[g]indicates the comparison with IlvC nucleic acid;
[h]indicates the comparison with IlvM nucleic acid;
[i]N-terminal end of Leu1;
[j]C-terminal end of Leu1.

In addition, two genes detected by complementation, the ilvB gene (homologous to ilvB, ilvI and ilvG of *E. coli*) and the ilvN gene (homologous to ilvH of *E. coli*), for which complementation data were not obtained, were identified.

Most of the proteins of *L. lactis* were similar in size to their homologues. However, three exceptions were observed. Relative to the proteins of *E. coli*, the lactococcal proteins IlvA and IlvC lack the C-terminal amino acids 73 and 147, respectively, and IlvD displays a deletion of 36 amino acids. One of the ORFs, designated ORF2, codes for a protein not displaying any homology with the enzymes of the pathway of synthesis of the branched amino acids, but carries two regions that are conserved in a superfamily of ATP-binding proteins (53).

FIG. 3 shows the alignment of 6 ATP-binding proteins with the ORF2 sequence of *L. lactis*. Needleman's software was used to obtain these results (54). In FIG. 3:
- the binding domains (53) are represented by NB1 and NB2;
- a short sequence shared by all the members of the ATP-dependent family is indicated by the symbols (#);
- the symbols (λ) indicate amino acids common to all the proteins;
- the symbols (.) indicate conserved substitutions;
- the amino acids shown in bold characters are present in at least five proteins;
- the figures at the left indicate the position of the amino acids, and the figures in brackets indicate the size of the proteins;

([5]), haemolysin secretion in *E. coli* (59);
([6]), cyclolysine secretion in *Bordetella pertussis* (60).

The organization of the sequenced segments is presented in FIG. 1. All the genes, except for the first one, upstream of LeuA (ORF1), are transcribed in the same direction. The leu and ilv genes are grouped together, and the two groups are separated by 121 bp. The leu genes are separated by less than 19 bp, except for leuB and leuC which are separated by four 72-bp direct repeats. The distance between the ilv genes is between approximately 10 and 42 bp, except for ilvB and ilvN which are separated by 9 bp.

6) Transcription Signals

Figure 4A:
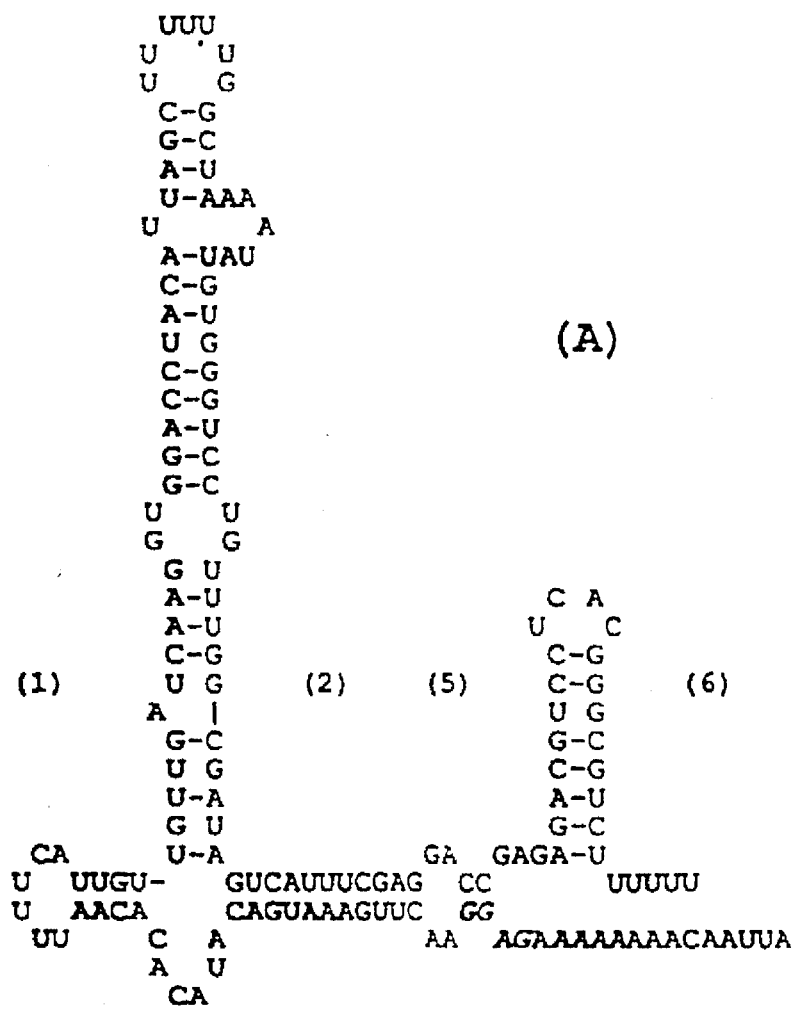
FIGS. 4A and 4B show the secondary structures of the major transcript serving as a transcription attenuator.
Figure 4B:
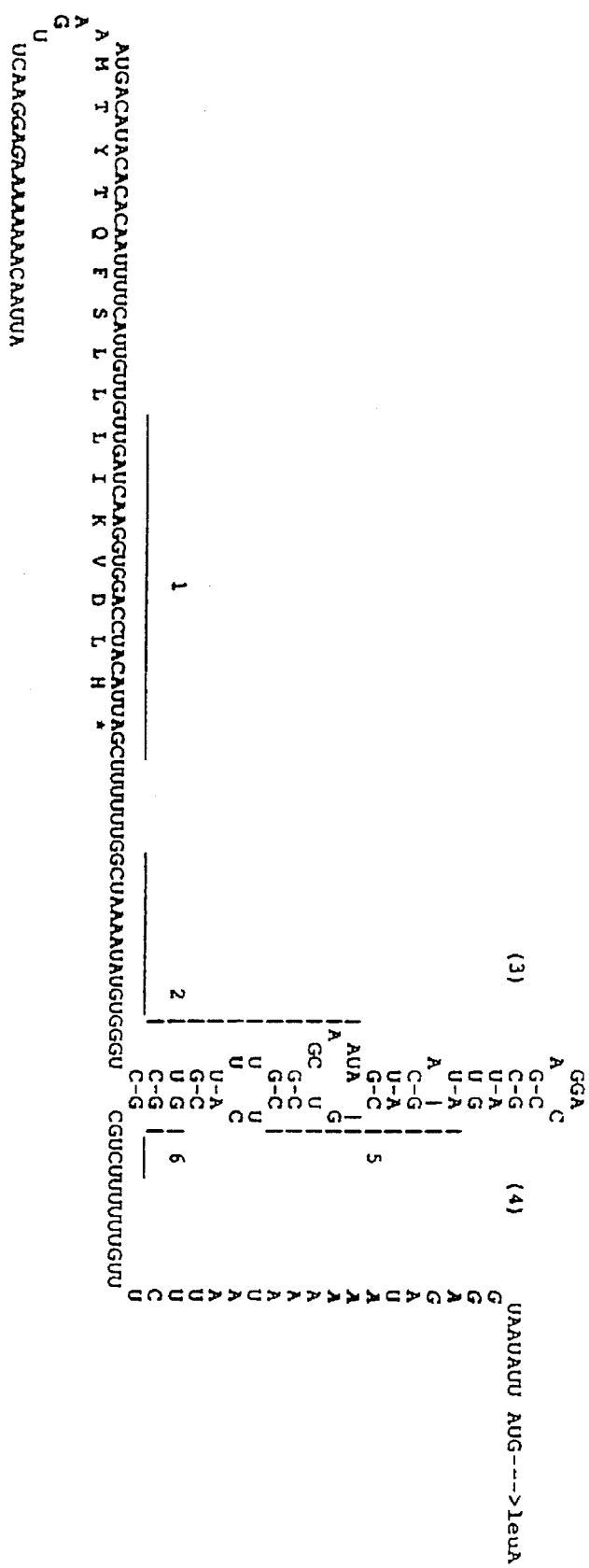

The sequences conforming to the consensus units of the lactococcus promoters were identified upstream of the assemblies of leu and ilv genes (see the positions of p1 and p2 in FIG. 1). The region between p1 and leuA strongly resembles the regulatory regions of the amino acid biosynthesis operons controlled by attenuation (61). The transcript initiated at p1 can follow two paths. One to the formation of a rho-independent transcription "terminator" (as shown in FIG. 4A). In addition, the transcript carries a 51-bp message, beginning with an ATG codon and ending with a TAG codon, which determines a leader peptide of 16 amino acids, four of which are a succession of leucine and isoleucine (as shown in FIG. 4B). The ribosome sited at the Leu and Ile codons prevents formation of the termination signal and leads to transcription of the leu genes downstream. Independent transcription "terminators" were not found between the two assemblies of genes or downstream of the ilvA gene.

7) Organization of the Ilv Operon

The genes involved in the pathway of synthesis of the branched amino acids in *L. lactis* subsp. *lactis* are organized in a large assembly divided into two units grouping together the leu and ilv genes. The two units are necessary for the synthesis of leucine, whereas only the second is required for the synthesis of isoleucine and valine. A transaminase, involved in the last step of the pathway of synthesis of the branched amino acids (product of the ilvE gene in *E. coli*), is not encoded by the assembly. This implies that this reaction is implemented by a non-specific transaminase, or alternatively that the corresponding gene in *L. lactis* subsp. *lactis* occurs elsewhere on the chromosome.

The leu and ilv genes are both preceded by a promoter; however, they are not separated by an independent transcription "terminator", suggesting that they form a single operon. This operon extends beyond the last biosynthesis gene, ilvA.

8) Regulation of the Ilv Operon

Sequence analysis strongly suggests that the operon is regulated by an attenuation mechanism, the mediator of which is a leucine-rich leader peptide. This peptide very closely resembles the leader peptide of the leu operon of *E. coli* and of *S. typhimurium* (62, 63), but differs from that of the ilvBN and ilvGMEDA operons of *E. coli*.

FIG. 4 shows the secondary structures of the leader transcript capable of participating as a mediator in transcription attenuation:

- at A, the termination topology is shown; units (1) and (2) are paired, and units (5) and (6) form a transcription terminator;
- at B, the antitermination topology is shown; units (3) and (4) are paired, and mask units (5) and (6).

In FIG. 4, the nucleotides in bold characters indicate the sequence coding for the leader peptide, and the nucleotides in bold italics indicate the ribosome binding sites of the leader peptide and the leuA gene. Stalling of the ribosome at the successive Leu and Ile residues could mask unit (1) and favour this topology.

Current models propose that the strength of the attenuation is dependent on the tRNA$^{leu}$ load during translation of the leader peptide. The presence of rare codons increases the response to leucine starvation by increasing the duration of ribosome stalling. In *E. coli*, the codon corresponding to the four leucine residues present in the leader peptide is CUA, which corresponds to only 2% of the leucine codons used for the proteins of this organism (64). In contrast, the leucine codon UUC, encountered three times in the leader transcript of the pathway of synthesis of the branched amino acids in *L. lactis*, corresponds to 24% of the leucine codons in the proteins of *L. lactis* (65). The isoleucine codon is also present in the leader peptide of *L. lactis*, following very closely the Leu codons, which is not the case in *E. coli*, and may hence affect the response of the operon to an arrest of the pathway of synthesis of the branched amino acids. Other studies are necessary to determine whether the model proposed for regulation in *E. coli* may be applied directly to *L. lactis*.

9) The Open Reading Frame ORF2

ORF2, inasmuch as it corresponds to a product belonging to the superfamily of ATP-binding proteins, is not a biosynthesis gene in the pathway of synthesis of the branched amino acids. The proteins of this superfamily are encountered both in prokaryotes and in eukaryotes, and share a similar base organization (66, 67). In prokaryotes, most of the members of this superfamily are components of the transport systems involving periplasmic binding proteins. These genes are generally cotranscribed with other genes (67), and have never been found in the biosynthesis operon. Other studies are necessary to establish the function of ORF2, but the latter is doubtless involved in the transport of the chain of synthesis of the branched amino acids, or in regulation of the genes of this pathway.

Isoleucine, leucine and valine represent 20% of the amino acids of *L. lactis* (68), whereas tryptophan and histidine, two other amino acids whose pathways of biosynthesis in *L. lactis* have been studied, represent less than 2%. This suggests that a fine regulation of the expression of the genes of the pathway of synthesis of the branched amino acids is necessary.

II—INTRODUCTION OF A NUCLEIC ACID CODING FOR AN α-ACETOLACTATE SYNTHASE INTO A HOST

The nucleic acid consisting of the DNA sequence bounded by the nucleotides located at positions 7977 and 10246 of SEQ ID NO: 11 and as shown in FIG. 2, and coding for the IlvB and IlvN polypeptides, is amplified by the Taq polymerase chain reaction from the DNA of FIG. 2, and using two oligo-nucleotides located upstream and downstream of the nucleic acid sequence coding for IlvBN.

The following two oligonucleotides were used:

CTAGTGAAGGTTGCGTTACA (SEQ ID No: 15)
TGCCATTTTTGTTTCCTCTA (SEQ ID No: 16)

After the polymerase chain reaction, the product of the reaction is cloned into an expression vector, such as pIL252, pIL253, pWV01, containing a promoter such as the promoter of the lactose operon or of the tryptophan operon, and where appropriate a terminator.

After cloning of the amplified segment in the appropriate orientation, the plasmid obtained is introduced by transformation into a strain of *L. lactis*, such as IL1403 or MG1363, which expresses IlvBN at a high level. This results in diversion of a part of the pyruvate pool obtained after glycolysis towards α-acetolactate, a precursor of diacetyl.

REFERENCES

1. Calvo, J. M. (1983) p. 267–284. In Herrman, K. M. Somerville, R. L. (eds.) Amino acids, biosynthesis and genetic regulation, Addison-Wesley, Reading, Mass.
2. Kohlhaw, G. B. (1983) p. 285–299. In Herrman, K. M. and Somerville, R. L. (eds.) Amino acids, biosynthesis and genetic regulation, Addison-Wesley, Reading, Mass.
3. Umbarger, H. E. (1983) p. 245–266. In Herman, K. M. and Somerville, R. L. (eds.) Amino acids, biosynthesis and genetic regulation, Addison-Wesley, Reading, Mass.
4. Umbarger, H. E. (1987) p. 353–367. In F. C. Neidhardt, J. L. Ingraham, K. B. Low, B. Magasanik, M. Schaechter and H. E. Umbarger (ed.), *Escherichia coli* and *Salmonella typhimurium*: Cellular and molecular biology, vol. 2. American Society for Microbiology, Washington, D.C.
5. Mackey, C. J., R. J. Warburg, H. O. Halvorson and S. A. Zahler. *Gene* 32, 49–56.
6. Vandeyar, M. A., C. J. Mackey, R. H. Lipsky and Z. A. Zahler (1986) p. 295–305. In Ganesan, A. T. and Hoch, J. A. (eds.), Bacillus molecular genetics and biotechnology applications. Academic Press Inc.
7. Ward, J. B., and S. A. Zahler (1973) *J. Bacteriol.* 116, 719–726.
8. Cordes, C., L. Eggeling and H. Sahm (1990) p. 339–351. In Heshlot, H., Davies, J., Florent, J., Bobichon, L., Durand, G., Penasse, L. (eds.), Société Française de microbiologie.
9. Pattee, P. A. (1976) *J. Bacteriol.* 127, 1167–1172.
10. Bachmann, B. J. (1987) p. 807–877. In F. C. Neidhardt, J. L. Ingraham, K. B. Low, B. Magasanik, M. Schaechter and H. E. Umbarger (ed.), *Escherichia Coli and Salmonella typhymurium*: Cellular and molecular biology, vol. 2. American Society for Microbiology, Washington, D.C.
11. Lawther, R. P., R. C. Wek, J. M. Lopes, R. Pereira, B. E. Taillon, and G. W. Hatfield (1987) *Nucleic Acids Res.* 15, 2137–2155.
12. Wek, R. C. and G. W. Hatfield (1986) *J. Bioch. Chem.* 261, 2441–2450.
13. Friedberg, D., E. R. Rosenthal, J. W. Jones and J. M. Calvo (1985) *Mol. Gen. Genet.* 199, 486–494.
14. Squires, C. H., M. DeFelice, S. R. Wessler and J. M. Calvo (1981) *J. Bacteriol.* 147, 797–804.
15. Mackey, C. J. and S. A. Zahler (1982) *J. Bacteriol.* 151, 1222–1229.
16. Tanaka, T. (1979) *Mol. Gen. Genet.* 175, 235–237.
17. Barat, M. C. Anagnostopoulos, and A. M. Schneider (1965) *J. Bacteriol.* 90, 357–369.
18. Ikawa, S., T. Shibata, T. Ando, and H. Saito (1980) *Mol. Gen. Genet.* 177, 359–368.
19. Somers, J. M., A. Amzallag, and R. B. Middleton (1973) *J. Bacteriol.* 113, 1268–1272.
20. Marsch, N. J., and D. E. Duggan (1972) *J. Bacteriol.* 109, 730–740.
21. Butlin, J. D., G. B. Cox and F. Gibson (1971) *Biochem. J.* 124, 75–81.
23. Simon, D., and A. Chopin (1988) *Biochimie* 70, 559–566.
24. Niaudet, B., L. Janniere, and S. D. Ehrlich (1985) *J. Bacteriol.* 163, 111–120.
25. Terzaghi, B. and W. E. Sandine (1975) *Appl. Microbiol.* 29, 807–813.
26. Cold Spring Harbor Laboratory, Cold Spring Harbor, N. Y. Maniatis, T., E. F. Fritsh, J. Sambrook (1982) Molecular cloning: a laboratory manual.
27. Loureire des Santos, A. L., A. Chopin (1987) *FEMS Microbiol. Lett.* 42, 209–212.
28. Simon, D., A. Rouault, M. C. Chopin (1985) *FEMS Microbiol. Lett.* 26, 239–241.
29. te Riele, H., B. Michel, S. D. Ehrlich (1986) *Proc. Natl. Acad. Sci. USA* 83, 2541–2545.
30. Dower, W. J., J. F. Miller, C. W. Ragsdale (1988) *Nuclei. Acid. Res.* 16, 6127–6145.
31. Anagnostopoulos, C. J. Spizizen (1961) *J. Bacteriol.* 81, 741–746.
32. Bron, S. (1990) Plasmids; in "Molecular Biology for Bacillus", C. R. Harwood, S. Cutting, pp. 148–149, John Wiley and Sons Ltd.
33. Corpet, F. (1988) *Nuclei. Acid. Res.* 16, 10881–10890.
34. Niaudel, B., and S. D. Ehrlich (1982) p. 201–209. in M. Polsinelli and G. Mazza (cds.), Transformation-80. Cotswold Press, Oxford UK.
35. Gribskov, G., J. Devereux, and R. R. Burgess (1984) *Nucleic Acids Res.* 12, 539–549.
36. de Vos, W. M. (1987) *FES Microbiol. Rev.* 46, 281–295.
37. Wek, R. C., C. A. Hauser and G. W. Hatfield (1985) *Nucleic Acid Res.* 13, 2995–4010.
38. Squires, C. H., M. Defelice, J. Devereux and J. M. Calvo (1983) *Nucleic Acids Res.* 11(52), 5299–5313.
39. Ricca, E. and J. M. Calvo (1990) *Nucleic Acid Res.* 18, 1290.
40. Rosenthal, E. R. and J. M. Calvo. *Nucleic Acid Res.* 18, 3072.
41. Imai, R., T. Sekiguchi, Y. Nosoh and K. Tsuda (1987) *Nucleic Acids Res.* 15, 4988.
42. Sekiguchi, T., Ortega-Cesena, Y. Nosoh, S. Ohashi, K. Tsuda and S. Kanaya (1986) *Biochimmica and Biophsica Acta.* 867, 36–44.
43. Kagawa, Y., H. Nojim, N. Nukiwa, M. Ishizuka, T. Nakajima, T. Yasuhara, T. Tanaka and T. Oshima. (1984) *J. Biol. Chem.* 259, 2956–2960.
44. Andreadis, A., Y.-P. Hsu, G. B. Kohlaw and P. Schimmel (1982) *Cell.* 31, 319–325.
45. Beltzer, J. P., L.-F. L. Chang, A. E. Hinkkanen and G. B. Kohlaw (1986) *J. Biol. Chem.* 261, 5160–5167.
46. Falco, S. C., K. S. Dumas and K. J. Livak (1985) *Nucleic Acid Res.* 13, 11.
47. Kielland-Brandt M. C., S. Holmhertg, J. G. L. Petersen and T. Nilssen-Tillgren (1984) *Carlsberg Res. Commun.* 49, 567–575.
48. Petersen J. G. L. and S. Holmberg (1986) *Nucleic Acids Res.* 14, 9631–9651.
49. Skala J., E. Capieaux, E. Balzl, W. Chen and A. Goffeau (1991) *Yeast* 7, 281–285.
50. Iturriaga, E. A., J. M. Diaz-Minguez, Z. P. Benito, M. I. Alvarez, and A. T. Eslava (1990) *Nucleic Acid Res.* 18, 4612.
51. Roncero, M. I. G., L. P. Jepsen, P. Stroman and R. van Heeswijck (1989) *Gene* 84, 335–343.
52. Wilbur, W. J. and D. Lipman (1983) *Proc. Natl. Acad. Sci. USA* 80, 726–730.
53. Higgins, C. F., M. L. Gallagher, M. L. Mimmack and S. R. Pearce (1988) *Bioassays* 8, 111–116.
54. Needleman, S. S., and C. D. Wunsch (1970) *J. Mol. Biol.* 48, 443–453.
55. Evans, I. J. and J. A. Downie (1986) *Gene* 43, 95–101.
56. Gilson, E., H. Nikaido and M. Hofnung (1982) *Nucleic Acids Res.* 10, 7449–7458.
57. Nohno, T., T. Saito and J. S. Hong (1986) *Mol. Gen. Genet.* 205, 260–269.
58. Gowrishankar, J. (1989) *J. Bacteriol.* 171, 1923–1931.
59. Felmlee, T., S. Pellett and R. A. Welch (1985) *J. Bacteriol.* 163, 94–105.
60. Glaser, P., H. Sakamoto, J. Bellalou, A. Ullmann and A. Danchin (1988) *EMBO J.* 7, 3997–4004.
61. Kolter, R. and C. Yanofski (1982) *Ann. Rev. Genet.* 16, 113–134.
62. Frieden, P., T. Newman and M. Freundlich (1982) *Proc. Natl. Acad. Sci. USA* 79, 6156–6160.
63. Wessler, S. R. and J. Calvo (1981) *J. Mol. Biol.* 149, 579–597.
64. Sharp, P. M., E. Cowe, D. G. Higgins, D. C. Shields, K. H. Wolfe, and F. Wright (1988) *Nucleic Acid Res.* 16, 8207–8211.
65. Van de Cuchte, M., J. Kok and G. Venema (1982) *FEMS Microbiol. Rev.* 88, 73–92.
66. Higgins, C. F., I. D. Hilce, G. P. C. Salmond, D. R. Gill, J. A. Downie, I. J. Evans, I. B. Holland, L. Cray, S. D. Bucked, A. W. Bell and M. A. Hermodson. (1986) *Nature* 323, 448–450.
67. Higgins, C. F., I. D. Hiles, K. Whalley and D. J. Jamieson (1985) *EMBO J.* 4, 113–1040.
68. Thomas, T. D. and G. G. Prichard (1987) *FEMS Microbiology Rev.* 46, 245–268.

SEQUENCE LISTING

| | |
|---|---|
| LOCUS | LACLEUILV    12720 bp ds-DNA    BCT    02-NOV-1992 |
| DEFINITION | *Lactococcus lactis* operon (leuA, leuB, leuC, leuD, ilvD, ilvB, ilvN, ilvC, ilvA) genes complete cds; complete ORF2. |
| ACCESSION | M90761 |
| KEYWORDS | ilvA gene; ilvB gene; ilvC gene; ilvD gene; ilvN gene; leuA gene; leuB gene; leuC gene; leuD gene; operon. |
| SOURCE | *Lactococcus lactis* (library: NCDO2118) DNA. |
| ORGANISM | *Lactococcus lactis* Prokaryotae; Firmicutes; Firmibacteria; Gram-positive cocci; Streptococcaceae. |
| REFERENCE | 1 (bases 1 to 12720) |
| AUTHORS | Godon, J.-J.J.-J., Chopin, M.-C.M. and Ehrlich, D. S. |
| TITLE | Branched-chain amino acid biosythesis genes in *Lactococcus lactis* subup. lactis. |
| JOURNAL | J. Bacteriol. 174, 6580–6589 (1992) |
| STANDARD | full automatic |
| FEATURES | Location/Qualifiers |
| attenuator | 260. .450 /note="putative" |
| repeat_region | 3039. .3327 /function="unknown" /rpt_type=DIRECT /note="putative" |
| CDS | 450. .1991 /EC_number="4.1.3.12" /gene="leuA" /citation=[1] /note="putative" /codon_start=1 |

/translation="MRKIEFFDTSLRDGEQTPGVSFSISEKVTIAKQLEKWRISVIEA

GFSAASPDSFEAVKQIADSLNDTAVTALARCVISDIDKAVEAVKGAKYPQIHVFIATS

PIHMKYKLKISPEEVLKNIDKCVRYARERVEVVEFSPEDATRTELNFLLEAVQTAVDA

GATYINIPDTVGYTTPEEYGKIFKFLIDNTKSDREIIFSPHCHDDLGMAVANSLAAIK

AGAGRVEGTVNGIGERAGNAALEEIAVALHIRKDFYQAQSPLKLSETAATAELISQFS

GIAIPKNKAIVGANAFAHESGIHQDGVLKNAETYEIITPELVGIKHNSLPLGKLSGRH

AFSEKLTELNIAYDDESLAILFEKFKKLADKKKEITDADIHALFTGETVKNLAGFILD

NVQIDGHKALVQLKNQEEEIYVSQGEGSGSVDAIFKAIDKVFNHQLKLISYSVDAVTD

GIDAQATTLVSVENLSTGTIFNAKGVDYDVLKGSAIAYMNANVLVQKENLQGKVEQIS

AHDGI"

| | |
|---|---|
| CDS | 2003. .3040 /gene="leuB" /note="putative" /codon_start=1 |

/translation="LSKKIVTLAGDGIGPEIMSAGLSVLKAVSKKIDFEYELEAKDFG

GIAIDKHGHPLPEETLQAVKNADAILLAAIGHPKYNNAKVRPEQGLLALRKELGLYAN

VRPLKIYPALKKLSPIRNVENVDFLVIRELTGGIYFGQHELADDKARDVNDYSADEIR

RILHFAFKSAQSRPRKLLTSVDKQNVLATSKLWRKMADEIADEYPDVRLEHQLVDSCA

MLLITNPQQFDVIVTENLFGDILSDEASSLAGSLGVMPSSSHGFNGLALYEPIHGSAP

DIAGKGIANPVSMILSIAMMLRESFGQEDGAAMIEKAVTQTFTDGILTKDLGGTATTK

EXTEAILKNCQ"

| | |
|---|---|
| CDS | 3403. .4785 /gene="leuC" /note="putative" /codon_start=1 |

/translation="MSGKTIFDKLWDQHVIAGNEGEPQLLYIDLHVIHEVTSPQAFQG

LREAGRRVRRKDLTYGTLDHNVPTQNIFNIQDLISKKQIDTFTKNVKEFDVPAETHGG

SEQUENCE LISTING

KGQGIVHMVAPESGRTQPGKTIVCGDSHTATNGAFGAIAFGIGTSEVEHVLATQTIWQ

VKPKRMKIEFQGHPQKGIYSKDFILALIAKYGVDAGVGYAVEYSGDAISDLSMEERMT

ICNMSIEFGAKIGLMNPDEKTYDYVKGREHAPKNFDEAVSKWEKLVSDSDAQYDKILS

LDVSQLKPMVTWGTNPGMGLEFGEKFPEINNDLNYERAYQYMDLKPGQTASDIDLGYI

FIGSCTNARLGDLEEAAKIIGDRHIADGLTGIVVPGSRPVKEAAEAQGLDKIFKEAGF

EWREPGCSACLGMNPDQIPEYVHCASTSNRNFEGRQGHNARTHLCSPAMAAAAAIAGK
FVDVRMLVTD"
    CDS                4805..5380
                    /gene="leuD"
                    /note="putative"
                    /codon_start=1
/translation="MEKFITYKGTSVPVMNDNIDTDQIIPKQFLKAIDKKGFGKNLFY

EWRYLKDYDENPDFILNAPKYKKASLLISGDNFGSGSSREHAAWALSDYGFRAIIAGS

YSDIFYNNALKNGLLPIKQPREVLNQLTKLSSQEEITIDLPHQLIITSLGDFHFEIDP
IWKDKLINGLDDIGITLQYEEAISAYEQKNQ"
    CDS                5394..6173
                    /function="unknown"
                    /note="ORF2; putative"
                    /codon_start=1
/translation="MTIINLKNVNLTRNKKEILKDITWKVNPGENWVILGLNGSGKSS

LLKLILAEEWKTSGEITVLNTQFRNGEIPKLRKRISVVGSFIAERFQPNIKAENLVYT

GKFNSSMLYKPYTDQELDEARQLLRQMGAKSLIGRNYASLSQGEKQVLLIARSLILKP

ELLILDEATNGLDLFAKEKLLKQLQQINQLKTAPTLIYISHHPDEITDIFTHLLLLRE

GKVIQSGKKENLLNEKILTDFYQEKVEVHRFEQKYFVIPAN"
    CDS                6295..8007
                    /gene="ilvD"
                    /note="putative"
                    /codon_start=1
/translation="MEFKYNGKVESVELNKYSKTLTPRSTQPATQAMYYGIGFKDEDF

KKAQVGIVSMDWDGNPCNMHLGTLGSKIKSSVNQTDGLIGLQFHTIGVSDGIANGKLG

MRYSLVSREVIADSIETNAGAEYYDAIVAIPGCDKNMPGSIIGMARLNRPSIMVYGGT

IEHGEYKGEKLNIVSAFEALGQKITGNISDEDYHGVICNAIPGQGACGGMYTANTLAA

AIETLGMSLPYSSSNPAVSQEKQEECDDIGLAIKNLLEKDIKPSDIMTKEAFENAITI

VMVLGGSTNAVLHIIAMANAIGVEITQDDFQRISDIIPVLGDFKPSGKYMMEDLHKIG

GLPAVLKYLLKEGKLHGDCLTVTGKTLAENVETALDLDFDSQDIMRPLKNPIKATGHL

QILYGNLAQGGSVAKISGKEGEFFKGTARVFDGEQHFIDGIESGRLHAGDVAVIRNIG

PVGGPGMPEMLKPTSALIGAGLGKSCALITDGRFSGGTHGFVVGHIVPEAVEGGLIGL

VEDDDIIEIDAVNNSISLKVSNEEIAKRRANYQKPTPKATRGVLAKFAKLTRPASEGC
VTDL"
    CDS                8018..9745
                    /gene="ilvB"
                    /note="putative"
                    /condon_start=1
/translation="MKKIKLEKPTSGSQLVLQTLKELGVEIIFGYPGGAMLPLYDAIH

NFEGIQHILARHEQGATHEAEGYAKSSGKVGVVVVTSGPGATNAVTGIADAYLDSVPL

LVFTGQVGRQSIGKDAFQEADTVGITAPITKYNYQIRETADIPRIVTEAYYLARTGRP

GPVEIDLPKDVSTLEVTEINDPSLNLPHYHESEKATDEQLQELLTELSVSKKPVIIAG

GGINYSGSVDIFRAFVEKYQIPVVSTLLGLGTLPISHELQLGMAGMHGSYAANMALVE

ADYIINLGSRFDDRVVSNPAKFAKNAVVAHIDIDAAELGKIVKTDIPILSDLKAALSR

LLQLNKVRTDFNDWIKTVIENKEKAPFTYEPQNHDIRPQETIKLIGEYTQGDAIIVTD

SEQUENCE LISTING

VGQHQMWVAQYYPYKNARQLITSGGMGTMGFGIPAAIGAKLAQPNKNVIVFVGDGGFQ

MTNQELALLNGYGIAIKVVLINNHSLGMVRQWQESFYEERRSQSVFDVEPNFQLLAEA

YGIKHVKLDNPKTLADDLKITTEDEPMLIEVLISKSEHVLPMIPAGLHNDEMIGLHFT
DKNEEIDNA"

```
CDS             9738..10214
                /gene="ilvN"
                /note="putative"
                /condon_start=1
```

/translation="MRRMIIAKLHNVTGIMNRFTAVLNRRQVNILSITAGVTESQDLT

HTTFVIEVDHLDEVEQIIKQLNRLIDVIEVADITDFPHVEREVVLIKVSAPPTIRAEI

FTMIEPFRVNVVDVNLENVTIQLTGDSAKIEALIEVVSPYGILNMARTGSAGFERG"

```
CDS             10260..11294
                /gene="ilvC"
                /note="putative"
                /condon_start=1
```

/translation="MAVTMYYEDDVEVSALAGKQIAVIGYGSQGHAHAQNLRDSGHNV

IIGVRHGKSFDKAKEDGFETFEVGEAVAKADVIMVLAPDELQQSIYEEDIKPNLKAGS

ALGFAHGFNIHFGYIKVPEDVDVFMVAPKAPGHLVRRTYTEGFGTPALFVSHQNASGH

AREIAMDWAKGIGCARVGIIETTFKEETEEDLFGEQAVLCGGLTALVEAGFETLTEAG

YAGELAYFEVLHEMKLIVDLMYEGGFTKMRQSISNTAEFGDYVTGPRIITDEVKKNMK

LVLADIQSGKFAQDFVDDFKAGRPKLIAYREAAKNLEIEKIGAEHVKQCHSHNLVMTM
PLKSISNFSY"

```
CDS             11337..12662
                /gene="ilvA"
                /note="putative"
                /condon_start=1
```

/translation="MISAKEVEDAYDLLKAVVTKTPLQLDPYLSNKYQANIYLKEVVT

KTPLQLDPYLSNKYQANIYLKEENLQKVRSFKLRGAYYSISKLSDEQRSKGVVCASAG

NHAQGVAFAANQLNISATIFMPVTIPNQKISQVKFFGESHVTIRLIGDTFDESARAAK

AFSQDNDKPFIDPFDDENVIAGQGTVALEIFAQAKKQGISLDKIFVQIGGGGLIAGIT

AYSKERYPQTEIIGVEAKGATSMKAAYSAGQPVTLEHIDKFADGIAVATVGQKTYQLI

NDKVKQLLAVDEGLISQTILELYSKLGIVAEPAGATSVAALELIKDEIKGKNIVCIIS

GGNNDISRMQEIEERALVYEGLKHYFVINFPQRPGSLRTFVSDILGPNDDITRFEYIK

RADKGKGPCLVGILLSDASDYDSLINRIERFDNRYVNLRGNDSLYELLV"

```
BASE COUNT    4254 a    2046 c    2621 g    3799 t
ORIGIN
M90761    Length: 12720    April 6, 1993    18:44    Type: N
Check: 7819..
     1    TAAAACTCGA TAATCTTGAG TCATAATTTC TCCTTAATCT
TATTAGTACA
    51    TTAGAATCCA TTATAATTTA ATCATTTTAT GTCTACCTAA
AGCAACAAAA
   101    TTGCTTGTAT ATTTTCTAAC AAGCTTAATT ATGTGGATTT
AATTGAATAT
   151    TAAAGGGAGA AGTTGTAATC TATTTGTTGT TAAATTCTTG
TTAATACAAA
   201    TAAATTTATT AAATATTATT ATTTTATTGA CAATTTAAAA
TATTAAGAGT
   251    ATTATAATGT AAATTAACAA AAAAAAGAGG AACTTGAAAT
GACATACACA
   301    CAATTTTCAT TGTTGTTGAT CAAGGTGGAC CTACATTAGC
TTTTTTGGCT
   351    AAAATATGTG GGTCCTGTTT GGCGATAGTC ATTTCGAGGA
CCGAGAGACG
   401    TCCTCACGGG CGTCTTTTTT GTTTCTTAAT AAAAAATAGA
GGTAATATTA
   451    TGCGAAAAAT TGAATTCTTT GACACAAGTT TGAGAGATGG
CGAACAGACA
   501    CCGGGCGTTA GTTTCTCCAT TTCAGAAAAA GTAACGATTG
CTAAACAACT
   551    GGAAAAATGG AGGATTTCTG TCATAGAGGC TGGTTTTTCT
GCGGCAAGTC
```

-continued

SEQUENCE LISTING

```
 601  CAGATAGTTT TGAAGCAGTA AAGCAAATTG CTGATTCTTT
      GAATGATACG
 651  GCTGTCACTG CATTAGCTCG CTGTGTTATT TCAGATATCG
      ATAAAGCGGT
 701  TGAAGCGGTA AAGGGGGCTA AATATCCGCA AATTCATGTT
      TTCATTGCAA
 751  CTTCACCTAT TCACATGAAA TATAAACTTA AAATCAGTCC
      CGAAGAAGTT
 801  TTGAAAAATA TTGATAAGTG TGTGAGATAC GCACGTGAAC
      GGGTCGAGGT
 851  TGTTGAGTTT TCTCCAGAGG ATGCAACAAG AACGGAGTTG
      AATTTTCTTT
 901  TAGAGGCTGT TCAAACGGCT GTCGATGCTG GAGCAACTTA
      TATTAATATT
 951  CCTGACACTG TCGGTTATAC GACACCAGAA GAATATGGAA
      AAATTTTTAA
1001  ATTTTTGATT GATAATACTA AGTCTGACCG AGAAATTATT
      TTTAGTCCAC
1051  ATTGTCATGA TGATTTAGGA ATGGCTGTAG CTAATTCATT
      AGCTGCAATT
1101  AAAGCTGGGG CTGGGAGAGT TGAAGGAACT GTCAATGGTA
      TTGGAGAGCG
1151  AGCTGGGAAT GCTGCTCTTG AAGAAATTGC TGTGGCACTA
      CATATTCGTA
1201  AAGATTTTTA TCAGGCACAA AGTCCTTTAA AACTTTCAGA
      AACTGCTGCA
1251  ACGGCAGAAC TAATTTCACA ATTTTCAGGA ATTGCTATTC
      CAAAAAATAA
1301  AGCAATTGTT GGTGCTAATG CTTTTGCACA CGAATCAGGA
      ATTCATCAAG
1351  ATGGTGTCCT TAAAAATGCT GAAACTTATG AAATTATTAC
      ACCAGAACTT
1401  GTCGGAATAA AGCATAATTC GTTGCCTTTA CGTAAACTTT
      CTGGTCGTCA
1451  TGCTTTTAGT GAAAAATTGA CGGAACTTAA TATTGCTTAT
      GACGATGAAA
1501  GTCTTGCAAT TTTATTTGAA AAATTTAAAA AATTAGCTGA
      CAAGAAAAAA
1551  GAAATTACTG ACGCAGATAT TCATGCCTTG TTTACAGGAG
      AAACGGTAAA
1601  AAATCTAGCT GGATTTATAC TTGATAATGT TCAAATTGAT
      GGGCACAAGG
1651  CATTGGTGCA ACTAAAAAAT CAAGAAGAGG AAATTTATGT
      TAGCCAAGGA
1701  GAGGGGTCAG GTTCAGTGGA TGCAATTTTT AAAGCTATTG
      ATAAAGTCTT
1751  TAATCATCAA CTAAAATTAA TTTCCTATTC AGTTGATGCT
      GTAACTGATG
1801  GAATTGATGC ACAAGCAACG ACTTTGGTTT CTGTTGAAAA
      TCTATCTACA
1851  GGCACTATAT TTAATGCTAA AGGTGTTGAT TATGATGTAT
      TGAAAGGAAG
1901  CGCCATTGCT TACATGAACG CTAATGTTTT AGTTCAAAAA
      GAAAATTTAC
1951  AAGGAAAGGT TGAACAAATT TCAGCTCATG ATGGAATTTA
      AGGTGAAAAA
2001  TATTGTCTAA AAAAATTGTG ACACTTGCGG GAGATGGAAT
      TGGGCCAGAA
2051  ATTATGTCAG CTGGTTTAAG TGTTTTAAAA GCTGTCAGTA
      AAAAAATTGA
2101  TTTTGAGTAT GAATTAGAAG CTAAAGATTT TGGAGGAATT
      GCAATTGATA
2151  AGCATGGTCA TCCTTTACCA GAAGAAACTT TGCAAGCAGT
      TAAAAATGCT
2201  GACGCAATCT TGCTCGCTGC AATTGGTCAT CCTAAATACA
      ACAATGCAAA
2251  AGTTAGACCA GAACAAGGGC TACTTGCTTT ACGAAAAGAA
      TTAGGACTGT
2301  ATGCTAATGT TCGTCCATTA AAAATTTATC CGGCTCTAAA
      AAAACTTTCT
2351  CCCATACGAA ATGTTGAAAA TGTTGATTTC CTAGTGATTC
      GCGAACTTAC
2401  AGGGGGAATC TATTTCGGTC AGCATGAATT GGCAGATGAT
      AAAGCACGAG
2451  ATGTCAATGA TTATTCTGCT GATGAAATAA GGAGAATTCT
      TCATTTTGCT
2501  TTCAAAAGTG CTCAAAGTCG GCCCAGAAAA TTACTGACTT
      CGGTTGATAA
```

SEQUENCE LISTING

```
2551  ACAAAATGTT CTTGCAACTT CTAAATTATG GCGAAAAATG
      GCTGATGAAA
2601  TTGCTGACGA ATATCCTGAT GTACGATTAG AGCACCAATT
      GGTCGATTCT
2651  TGTGCGATGT TACTGATTAC TAATCCGCAA CAATTTGATG
      TGATAGTCAC
2701  TGAAAATCTA TTTGGTGATA TTCTCTCTGA TGAAGCAAGT
      AGTTTGGCCG
2751  GTAGCTTAGG AGTGATGCCT TCGAGTTCGC ATGGATTTAA
      CGGTTTAGCA
2801  CTCTATGAGC CAATTCATGG TTCGGCACCA GATATTGCAG
      GAAAAGGAAT
2851  TGCGAACCCT GTTTCGATGA TTCTATCAAT TGCCATGATG
      CTAAGAGAAT
2901  CTTTTGGGCA AGAAGATGGG GCTGCGATGA TTGAAAAAGC
      CGTAACCCAA
2951  ACTTTTACTG ACGGAATTTT GACTAAAGAT TTAGGTGGGA
      CTGCAACAAC
3001  TAAAGAAATG ACAGAAGCAA TCCTGAAAAA TTGTCAGTAA
      AATGCGATTG
3051  AATAGTGAGC ATTTTAGTTG TAGATAAAAG AACCGTCAGC
      ATAGCTGACA
3101  ATTCTGTCAG TAAATGCGAT TGAATAGTGA GCATTTTAGT
      TGTAGATAAA
3151  AGAACCGTCA GCATAGCTGA CAATTCTGTC AGTAATTGCG
      ATTGAATAGT
3201  GAGCATTTTA GTTGTAGATA AAAGAACCGT CAGCATAGCT
      GACAATTCTG
3251  TCAGTAATTG CGATTGAATA GTGAGCATTT TAGTTGTAGA
      TAAAAGAACT
3301  ATCAGCGTAA CTGACAATTC TGTCAGTAAA TATTACTGAC
      AAAAAGTACA
3351  AAATTACTGA CAGAATTTGT CAGAATAAAT TTTTAAAAAA
      GGAAATAAAA
3401  AAATGTCAGG TAAAACAATA TTTGATAAAC TTTGGGATCA
      GCATGTGATT
3451  GCTGGAAATG AGGGAGAACC TCAACTGCTT TATATTGACC
      TTCATGTTAT
3501  TCATGAGGTT ACGAGTCCGC AAGCATTTCA GGGCTTACGT
      GAAGCAGGAC
3551  GTCGTGTTCG GAGAAAAGAT TTGACATACG GAACTCTTGA
      CCACAATGTT
3601  CCAACACAAA ATATTTTTAA TATTCAAGAT TTGATTTCTA
      AAAAACAAAT
3651  TGATACTTTT ACTAAAAATG TCAAAGAATT TGATGTTCCA
      GCGGAGACTC
3701  ATGGTGGAAA AGGACAAGGA ATTGTTCACA TGGTAGCACC
      TGAATCTGGC
3751  AGAACTCAAC CGGGAAAAAC AATTGTTTGT GGCGATAGTC
      ATACCGCAAC
3801  AAATGGAGCA TTTGGTGCAA TTGCTTTTGG AATTGGTACA
      AGTGAAGTTG
3851  AACATGTTCT TGCAACTCAA ACCATTTGGC AAGTTAAACC
      CAAGCGTATG
3901  AAAATTGAAT TTCAAGGTCA TCCACAAAAA GGAATTTATA
      GCAAAGACTT
3951  TATCCTCGCA TTAATTGCTA AATATGGTGT GGATGCAGGT
      GTAGGTTATG
4001  CGGTTGAATA TAGTGGGGAT GCTATCAGTG ATTTAAGCAT
      GGAAGAACGG
4051  ATGACAATCT GTAACATGTC AATTGAATTT GGGGCAAAAA
      TTGGCCTGAT
4101  GAATCCTGAT GAAAAAACTT ATGACTATGT CAAAGGGCGT
      GAACATGCAC
4151  CTAAAAACTT TGATGAAGCT GTCAGTAAAT GGGAAAAACT
      TGTCAGTGAT
4201  TCTGATGCAC AATACGATAA GATTTTAAGT CTTGATGTCA
      GCCAGTTGAA
4251  ACCAATGGTG ACATGGGGAA CAAATCCCGG AATGGGCCTA
      GAATTTGGCG
4301  AAAAGTTTCC GGAAATTAAC AATGATTTGA ATTATGAACG
      TGCTTATCAG
4351  TACATGGATT TAAAGCCAGG CCAAACCGCT TCTGACATAG
      ATTAGGCTA
4401  TATTTTCATT GGTTCTTGTA CGAATGCTAG ACTTGGTGAT
      TTAGAAGAAG
4451  CTGCAAAAAT TATTGGAGAC AGACATATTG CTGATGGACT
      GACAGGAATT
```

SEQUENCE LISTING

| | | |
|---|---|---|
| 4501 | GTCGTCCCTG GAAGCAGACC TGTGAAAGAA GCGGCTGAAG | CACAAGGGCT |
| 4551 | TGATAAAATT TTTAAAGAAG CTGGTTTTGA ATGGCGGGAA | CCGGGTTGCT |
| 4601 | CAGCCTGTCT TGGAATGAAT CCTGACCAAA TTCCAGAATA | CGTTCATTGT |
| 4651 | GCTTCAACCT CTAATCGAAA TTTTGAAGGT CGTCAAGGAC | ATAATGCAAG |
| 4701 | AACGCACCTG TGCTCTCCAG CTATGGCTGC TGCCGCCGCA | ATCGCTGGTA |
| 4751 | AATTTGTAGA TGTTAGAATG CTCGTAACAG ATTAGTCTGT | AGAAAGAAAA |
| 4801 | AAAGATGGAA AAATTCACGA TTTACAAAGG GACAAGTGTT | CCAGTCATGA |
| 4851 | ACGATAATAT TGACACAGAC CAAATTATTC CTAAACAATT | TTTGAAAGCA |
| 4901 | ATCGATAAAA AGGGCTTTGG GAAAAATTTA TTTTATGAAT | GGCGTTATCT |
| 4951 | TAAAGATTAC GATGAGAATC CTGATTTTAT TTTGAATGCT | CCAAAATACA |
| 5001 | AAAAAGCTTC TCTGTTAATT TCAGGAGATA ATTTTGGTTC | GGGTTCTTCA |
| 5051 | AGAGAACATG CGGCATGGGC CTTATCAGAT TACGGCTTTC | GGGCAATTAT |
| 5101 | TGCTGGCTCT TACTCAGATA TTTTTTATAA TAATGCTTTA | AAAAATGGCT |
| 5151 | TGTTACCAAT TAAACAACCA AGAGAAGTTC TAAATCAACT | GACAAAACTG |
| 5201 | TCAAGTCAAG AAGAAATTAC AATTGATTTA CCCCATCAGC | TAATCATCAC |
| 5251 | AAGCCTTGGT GACTTTCATT TTGAGATTGA CCCCATTTGG | AAAGACAAAT |
| 5301 | TAATTAATGG CTTAGATGAT ATTGGAATAA CTTTGCAATA | TGAAGAAGCA |
| 5351 | ATCTCAGCTT ACGAACAAAA AAATCAATAA GAGCGAGCCT | AAAATGACAA |
| 5401 | TTATTAATTT AAAGAATGTA AATCTTACTC GAAATAAAAA | AGAAATTCTT |
| 5451 | AAAGATATTA CTTGGAAAGT AAATCCCGGC GAAAATTGGG | TTATTCTGGG |
| 5501 | CCTCAACGGC TCTGGAAAAT CAAGTCTTTT GAAATTGATT | TTAGCAGAAG |
| 5551 | AATGGAAAAC TTCTGGTGAA ATCACTGTTT TAAATACTCA | ATTTAGAAAT |
| 5601 | GGAGAAATTC CTAAGTTGAG AAAAAGAATC AGCGTAGTTG | GCTCATTTAT |
| 5651 | TGCTGAAAGA TTTCAACCAA ATATTAAGGC TGAAAACCTT | GTTTATACTG |
| 5701 | GGAAATTTAA TTCGAGCATG CTCTATAAAC CCTACACAGA | TCAGGAACTT |
| 5751 | GATGAGGCCC GTCAGCTTTT AAGACAAATG GGCGCAAAAT | CACTTATTGG |
| 5801 | CCGAAATTAT GCCAGCCTTT CTCAAGGGGA AAAGCAAGTT | CTTCTTATTG |
| 5851 | CTAGGAGCTT AATTTTAAAG CCTGAGCTTT TAATTTTGGA | CGAAGCAACG |
| 5901 | AACGGTTTAG ATTTATTTGC TAAAGAAAAA TTATTAAAGC | AACTGCAGCA |
| 5951 | GATTAATCAA TTAAAAACCG CACCAACACT AATTTATATT | TCTCATCATC |
| 6001 | CCGATGAAAT CACTGATATT TTTACTCACC TTTTACTTTT | AAGAGAAGGA |
| 6051 | AAAGTGATTC AATCAGGGAA AAAAGAAAAC TTATTAAATG | AAAAGATACT |
| 6101 | TACTGATTTT TATCAAGAAA AAGTAGAAGT TCACCGTTTT | GAGCAGAAAT |
| 6151 | ATTTTGTAAT TCCTGCTAAC TGAGAAAGGA AAGCAAAAGT | ATTTTATATA |
| 6201 | CTATATAGAA TATTCTGACA GATTATTGTA TTTTCATTTT | TTTAGTGATA |
| 6251 | AAATAGCTCT ATGTAAATTT ACGGGGAGGT CAAAAAGATA | ACATATGGAA |
| 6301 | TTCAAATATA ACGGAAAAGT TGAATCAGTG GAACTCAATA | AATATTCTAA |
| 6351 | GACATTGACT CCAAGATCAA CACAACCAGC GACTCAAGCG | ATGTACTACG |
| 6401 | GCATTGGTTT TAAAGATGAG GATTTCAAAA AAGCTCAGGT | CGGAATCGTC |

SEQUENCE LISTING

| | |
|---|---|
| 6451 | AGCATGGATT GGGACGGAAA TCCATGTAAT ATGCACTTGG GAACACTTGG |
| 6501 | GAGTAAAATC AAAAGTTCTG TCAACCAAAC TGACGGATTG ATTGGACTTC |
| 6551 | AATTTCATAC TATTGGAGTT TCTGATGGAA TTGCTAACGG AAAGCTTGGC |
| 6601 | ATGAGATATT CTTTGGTCAG TCGTGAAGTT ATTGCTGACA GCATCGAAAC |
| 6651 | CAACGCTGGC GCAGAATATT ATGATGCCAT CGTTGCCATT CCCGGTTGTG |
| 6701 | ATAAAAATAT GCCCGGGTCA ATTATCGGAA TGGCTCGCTT AAATCGTCCG |
| 6751 | TCAATTATGG TCTATGGTGG AACGATTGAA CATGGCGAAT ATAAAGGTGA |
| 6801 | AAAATTAAAT ATTGTTTCGG CCTTTGAAGC TCTGGGGCAA AAAATCACTG |
| 6851 | GAAATATTTC TGATGAAGAT TATCATGGCG TTATTTGCAA TGCCATTCCA |
| 6901 | GGACAAGGTG CTTGCGGAGG AATGTACACT GCCAATACCC TGGCTGCTGC |
| 6951 | TATTGAAACT TTGGGAATGA GTTTACCTTA TTCCTCTTCC AATCCAGCAG |
| 7001 | TCAGTCAAGA AAAACAAGAA GAGTGTGATG ACATTGGTTT AGCCATCAAA |
| 7051 | AATTTATTAG AAAAAGATAT TAAACCAAGT GATATCATGA CCAAAGAAGC |
| 7101 | TTTTGAAAAT GCCATAACAA TTGTCATGGT CCTTGGAGGC TCAACCAATG |
| 7151 | CTGTGCTTCA TATCATTGCA ATGGCAAATG CCATTGGTGT AGAAATTACG |
| 7201 | CAAGATGATT TCCAACGTAT TTCAGATATT ATCCCTGTTC TTGGCGATTT |
| 7251 | CAAACCGAGC GGAAAATATA TGATGGAAGA TCTGCACAAA ATTGGTGGCC |
| 7301 | TTCCTGCTGT TTTGAAATAC CTACTTAAAG AAGGAAAACT TCACGGTGAT |
| 7351 | TGTTTGACCG TCACAGGTAA AACTTTGGCT GAAAATGTTG AAACAGCATT |
| 7401 | AGATTTGGAC TTTGACAGTC AAGATATTAT GCGACCACTA AAAAATCCAA |
| 7451 | TTAAAGCTAC TGGACATTTA CAAATTTTGT ACGGTAATCT TGCCCAAGGG |
| 7501 | GGTTCTGTTG CAAAAATTTC TGGTAAAGAA GGCGAATTTT TCAAAGGAAC |
| 7551 | AGCTCGTGTT TTTGACGGAG AACAACACTT TATCGATGGC ATTGAGTCTG |
| 7601 | GCCGATTGCA TGCCGGTGAT GTTGCGGTCA TTAGAAATAT TGGCCCAGTC |
| 7651 | GGAGGTCCGG GAATGCCAGA GATGTTAAAA CCAACCTCAG CATTAATTGG |
| 7701 | AGCAGGACTT GGAAAATCTT GTGCCCTAAT TACTGACGGA AGATTTTCTG |
| 7751 | GTGGCACACA CGGCTTTGTT GTGGGTCATA TCGTCCCTGA AGCAGTTGAA |
| 7801 | GGTGGGTTGA TTGGTTTAGT TGAAGATGAT GATATTATCG AAATTGATGC |
| 7851 | GGTGAATAAT AGTATTAGTT TAAAAGTTTC TAATGAAGAA ATTGCTAAAC |
| 7901 | GACGTGCCAA TTATCAAAAA CCAACCCCTA AAGCAACGCG TGGTGTTCTT |
| 7951 | GCAAAATTTG CCAAACTTAC GCGCCCCGCT AGTGAAGGTT GCGTTACAGA |
| 8001 | TTTATAGAAA GGTTTGAATG AAAAAAATAA AGTTAGAAAA ACCTACTTCC |
| 8051 | GGTTCCCAAC TTGTTCTCCA AACCTTAAAA GAACTTGGAG TAGAAATTAT |
| 8101 | TTTTGGTTAT CCTGGTGGGG CCATGCTCCC CTTGTATGAT GCGATTCATA |
| 8151 | ATTTTGAAGG AATTCAACAT ATTTTAGCCC GTCATGAGCA AGGAGCAACG |
| 8201 | CATGAAGCCG AAGGTTACGC TAAATCGTCT GGTAAAGTTG GTGTCGTCGT |
| 8251 | TGTTACGTCA GGACCAGGAG CGACTAATGC AGTAACCGGA ATTGCTGACG |
| 8301 | CTTATCTTGA TTCAGTCCCA TTGTTAGTTT TCACAGGTCA AGTTGGCCGT |
| 8351 | CAGTCAATTG GTAAAGATGC TTTTCAAGAA GCAGATACTG TTGGAATTAC |

SEQUENCE LISTING

```
8401  AGCCCCAATT ACAAAATATA ATTATCAAAT TAGGGAAACC
GCAGATATTC
8451  CAAGAATTGT TACAGAAGCC TATTATTTGG CAAGGACAGG
ACGTCCTGGA
8501  CCAGTAGAAA TTGATTTACC AAAAGATGTT TCCACCCTTG
AAGTCACTGA
8551  AATTAATGAC CCAAGCTTGA ATCTTCCTCA TTATCACGAA
AGTGAAAAAG
8601  CGACTGATGA ACAATTGCAA GAATTACTGA CAGAACTTTC
TGTCAGTAAA
8651  AAACCAGTCA TTATTGCTGG CGGAGGAATT AATTATTCTG
GCTCAGTTGA
8701  TATTTTCAGA GCATTTGTCG AAAAATATCA AATTCCAGTT
GTTTCTACAT
8751  TGCTTGGCTT AGGAACATTA CCAATCAGCC ACGAATTGCA
ACTAGGAATG
8801  GCAGGAATGC ACGGTTCATA CGCTGCAAAT ATGGCTTTAG
TTGAAGCTGA
8851  CTATATTATT AATTTGGGAT CACGTTTTGA CGATAGAGTT
GTATCCAATC
8901  CTGCAAAATT TGCTAAAAAT GCTGTCGTTG CTCATATTGA
TATTGACGCT
8951  GCTGAACTTG GCAAAATTGT AAAAACCGAT ATTCCAATCC
TTTCTGATTT
9001  GAAAGCGGCT TTAAGCAGAC TTTTGCAATT AAATAAGGTC
AGGACTGACT
9051  TTAATGATTG GATTAAAACT GTCATTGAAA ATAAAGAGAA
AGCACCATTT
9101  ACTTATGAGC CCCAAAACCA TGATATCCGT CCACAGGAAA
CAATTAAATT
9151  AATTGGAGAA TACACTCAAG GAGATGCAAT CATTGTAACT
GACGTTGGGC
9201  AACATCAAAT GTGGGTGGCG CAATATTATC CTTATAAAAA
TGCAAGGCAA
9251  CTTATTACTT CTGGGGGAAT GGGAACGATG GGCTTTGGCA
TTCCTGCAGC
9301  AATCGGTGCA AAGCTGGCAC AGCCAAATAA AAATGTCATT
GTTTTTGTTG
9351  GCGATGGTGG CTTTCAAATG ACTAATCAAG AATTAGCATT
ACTTAATGGC
9401  TACGGTATTG CAATCAAAGT TGTGCTGATT AATAATCATT
CATTGGGAAT
9451  GGTACGTCAA TGGCAAGAAT CATTCTATGA AGAGCGACGT
TCACAATCGG
9501  TTTTTGATGT TGAACCCAAT TTTCAATTGT TAGCCGAAGC
TTATGGCATC
9551  AAACATGTTA AGTTAGATAA TCCAAAAACT TTGGCTGATG
ATTTAAAAAT
9601  TATTACAGAA GATGAGCCAA TGCTTATTGA AGTTCTAATT
TCAAAATCTG
9651  AGCATGTTTT ACCAATGATA CCAGCTGGAT TACACAATGA
CGAAATGATT
9701  GGACTTCATT TTACTGATAA GAATGAGGAG ATAGATAATG
CGTAGAATGA
9751  TTATCGCAAA ACTTCATAAC GTGACAGGAA TTATGAATCG
ATTTACCGCC
9801  GTTCTCAATC GAAGGCAAGT GAACATTCTC TCAATTACCG
CTGGAGTTAC
9851  AGAAAGTCAA GACTTAACTC ATACCACTTT TGTTATTGAA
GTTGATCATC
9901  TTGATGAAGT AGAACAAATC ATTAAACAAT TAAATCGCTT
AATAGATGTA
9951  ATTGAAGTAG CTGATATTAC TGATTTTCCT CATGTAGAAC
GTGAAGTCGT
10001 CTTGATTAAA GTATCAGCTC CACCGACCAT TAGGGCAGAA
ATTTTTACAA
10051 TGATTGAACC TTTTAGAGTA AATGTAGTTG ATGTCAATCT
GGAAAATGTC
10101 ACCATTCAAT TAACGGGTGA TTCAGCAAAA ATCGAAGCAC
TTATTGAGGT
10151 TGTTAGTCCT TATGGCATTC TAAATATGGC TCGGACAGGT
AGTGCAGGTT
10201 TTGAGCGTGG CTAAATTTAA ATAAGTTAAC AAATAAATAG
AAAAATAGAG
10251 GAAACAAAAA TGGCAGTTAC AATGTATTAT GAAGATGATG
TAGAAGTATC
10301 AGCACTTGCT GGAAAGCAAA TTGCAGTAAT CGGTTATGGT
TCACAAGGAC
```

SEQUENCE LISTING

| | |
|---|---|
| 10351 | ATGCTCACGC ACAGAATTTG CGTGATTCTG GTCACAACGT |
| TATCATTGGT | |
| 10401 | GTGCGCCACG GAAAATCTTT TGATAAAGCA AAAGAAGATG |
| GCTTTGAAAC | |
| 10451 | ATTTGAAGTA GGAGAAGCAG TAGCTAAAGC TGATGTTATT |
| ATGGTTTTGG | |
| 10501 | CACCAGATGA ACTTCAACAA TCCATTTATG AAGAGGACAT |
| CAAACCAAAC | |
| 10551 | TTGAAAGCAG GTTCAGCACT TGGTTTTGCT CACGGATTTA |
| ATATCCATTT | |
| 10601 | TGGCTATATT AAAGTACCAG AAGACGTTGA CGTCTTTATG |
| GTTGCGCCTA | |
| 10651 | AGGCTCCAGG TCACCTTGTC CGTCGGACTT ATACTGAAGG |
| TTTTGGTACA | |
| 10701 | CCAGCTTTGT TTGTTTCACA CCAAAATGCA AGTGGTCATG |
| CGCGTGAAAT | |
| 10751 | CGCAATGGAT TGGGCCAAAG GAATTGGTTG TGCTCGAGTG |
| GGAATTATTG | |
| 10801 | AAACAACTTT TAAAGAAGAA ACAGAAGAAG ATTTGTTTGG |
| AGAACAAGCT | |
| 10851 | GTTCTATGTG GAGGTTTGAC AGCACTTGTT GAAGCCGGTT |
| TTGAAACACT | |
| 10901 | GACAGAAGCT GGATACGCTG GCGAATTGGC TTACTTTGAA |
| GTTTTGCACG | |
| 10951 | AAATGAAATT GATTGTTGAC CTCATGTATG AAGGTGGTTT |
| TACTAAAATG | |
| 11001 | CGTCAATCCA TCTCAAATAC TGCTGAGTTT GGCGATTATG |
| TGACTGGTCC | |
| 11051 | ACGGATTATT ACTGACGAAG TTAAAAAGAA TATGAAGCTT |
| GTTTTGGCTG | |
| 11101 | ATATTCAATC TGGAAAATTT GCTCAAGATT TCGTTGATGA |
| CTTCAAAGCG | |
| 11151 | GGGCGTCCAA AATTAATAGC CTATCGCGAA GCTGCAAAAA |
| ATCTTGAAAT | |
| 11201 | TGAAAAAATT GGGGCAGAGC ACGTCAAGCA ATGCCATTCA |
| CACAATCTGG | |
| 11251 | TGATGACGAT GCCTTTAAAA TCTATCAGTA ATTTCTCTTA |
| TTGATTGAAC | |
| 11301 | AAAAACATAA AAGCATTTTA TGGAGGAATG ACATAAATGA |
| TAAGTGCCAA | |
| 11351 | AGAGGTTGAA GATGCCTATG ATTTGTTAAA AGCAGTTGTC |
| ACTAAAACAC | |
| 11401 | CTTTACAATT AGACCCTTAC CTTTCCAATA AATATCAAGC |
| AAATATTTAC | |
| 11451 | TTAAAAGAAG TTGTCACTAA AACACCTTTA CAATTAGACC |
| CTTACCTTTC | |
| 11501 | CAATAAATAT CAAGCAAATA TTTACTTAAA AGAAGAAAAC |
| TTACAGAAAG | |
| 11551 | TTCGTTCTTT TAAATTACGA GGAGCTTATT ATTCTATCAG |
| TAAATTATCT | |
| 11601 | GATGAGCAAC GCTCTAAAGG AGTGGTTTGT GCCTCAGCAG |
| GAAATCATGC | |
| 11651 | ACAAGGGGTT GCTTTTGCTG CAAATCAATT AAATATTTCT |
| GCGACAATTT | |
| 11701 | TTATGCCCGT TACCACACCT AACCAAAAAA TTTCACAAGT |
| TAAATTTTTT | |
| 11751 | GGCGAAAGTC ACGTAACAAT TCGTTTAATT GGTGATACTT |
| TTGATGAATC | |
| 11801 | AGCCAGAGCA GCAAAAGCTT TTTCTCAAGA TAATGACAAA |
| CCATTTATAG | |
| 11851 | ACCCTTTTGA TGATGAAAAT GTAATTGCTG GTCAAGGGAC |
| AGTGGCTTTA | |
| 11901 | GAAATTTTTG CGCAAGCTAA AAAACAAGGA ATAAGTTTAG |
| ATAAGATTTT | |
| 11951 | TGTACAGATT GGTGGAGGTG GTTTAATTGC AGGAATTACT |
| GCCTACAGTA | |
| 12001 | AGGAGCGCTA TCCCCAAACT GAAATTATCG GAGTTGAAGC |
| AAAAGGGGCA | |
| 12051 | ACAAGTATGA AAGCTGCCTA CTCTGCTGGT CAGCCCGTCA |
| CCTTGGAACA | |
| 12101 | CATTGATAAA TTTGCTGACG GAATTGCGGT TGCGACTGTC |
| GGTCAGAAAA | |
| 12151 | CTTACCAACT TATTAATGAC AAAGTGAAAC AATTGCTTGC |
| GGTTGATGAA | |
| 12201 | GGTTTAATTT CTCAAACCAT ACTCGAATTG TATTCAAAAT |
| TAGGAATTGT | |
| 12251 | CGCCGAGCCA GCAGGTGCAA CATCTGTTGC CGCACTTGAA |
| CTTATTAAAG | |

SEQUENCE LISTING

| | |
|---|---|
| 12301 | ATGAAATCAA GGGTAAAAAT ATCGTCTGTA TCATCAGCGG |
| CGGAAATAAT | |
| 12351 | GATATTAGTC GAATGCAAGA AATTGAAGAA AGAGCTTTGG |
| TTTATGAAGG | |
| 12401 | TCTAAAACAT TATTTTGTCA TTAACTTTCC TCAAAGACCA |
| GGATCCTTAC | |
| 12451 | GAACTTTTGT CAGTGATATT TTAGGGCCAA ATGATGATAT |
| CACCCGATTT | |
| 12501 | GAGTACATCA AAAGGGCTGA TAAAGGTAAA GGACCTTGTC |
| TTGTTGGGAT | |
| 12551 | TTTACTTTCA GATGCTAGTG ATTATGATTC ATTGATTAAT |
| CGGATTGAAA | |
| 12601 | GATTTGATAA TCGTTATGTT AACTTACGTG GAAATGATAG |
| TTTATACGAA | |
| 12651 | CTTTTGGTCT AACTAACCAA TTGGTTTGAG CCATTTTCTA |
| GTTTCAATTC | |
| 12701 | TCTTTAAATC ACTAGAAATT | ilvb    Length: 1728    September 22, 1993    11:08    Type: N
Check: 9885 ..

| | |
|---|---|
| 1 | ATGAAAAAAA TAAAGTTAGA AAACCTACT TCCGGTTCCC |
| AACTTGTTCT | |
| 51 | CCAAACCTTA AAAGAACTTG GAGTAGAAAT TATTTTTGGT |
| TATCCTGGTG | |
| 101 | GGGCCATGCT CCCCTTGTAT GATGCGATTC ATAATTTTGA |
| AGGAATTCAA | |
| 151 | CATATTTTAG CCCGTCATGA GCAAGGAGCA ACGCATGAAG |
| CCGAAGGTTA | |
| 201 | CGCTAAATCG TCTGGTAAAG TTGGTGTCGT CGTTGTTACG |
| TCAGGACCAG | |
| 251 | GAGCGACTAA TGCAGTAACC GGAATTGCTG ACGCTTATCT |
| TGATTCAGTC | |
| 301 | CCATTGTTAG TTTTCACAGG TCAAGTTGGC CGTCAGTCAA |
| TTGGTAAAGA | |
| 351 | TGCTTTTCAA GAAGCAGATA CTGTTGGAAT TACAGCCCCA |
| ATTACAAAAT | |
| 401 | ATAATTATCA AATTAGGGAA ACCGCAGATA TTCCAAGAAT |
| TGTTACAGAA | |
| 451 | GCCTATTATT TGGCAAGGAC AGGACGTCCT GGACCAGTAG |
| AAATTGATTT | |
| 501 | ACCAAAAGAT GTTTCCACCC TTGAAGTCAC TGAAATTAAT |
| GACCCAAGCT | |
| 551 | TGAATCTTCC TCATTATCAC GAAAGTGAAA AAGCGACTGA |
| TGAACAATTG | |
| 601 | CAAGAATTAC TGACAGAACT TTCTGTCAGT AAAAAACCAG |
| TCATTATTGC | |
| 651 | TGGCGGAGGA ATTAATTATT CTGGCTCAGT TGATATTTTC |
| AGAGCATTTG | |
| 701 | TCGAAAAATA TCAAATTCCA GTTGTTTCTA CATTGCTTGG |
| CTTAGGAACA | |
| 751 | TTACCAATCA GCCACGAATT GCAACTAGGA ATGGCAGGAA |
| TGCACGGTTC | |
| 801 | ATACGCTGCA AATATGGCTT TAGTTGAAGC TGACTATATT |
| ATTAATTTGG | |
| 851 | GATCACGTTT TGACGATAGA GTTGTATCCA ATCCTGCAAA |
| ATTTGCTAAA | |
| 901 | AATGCTGTCG TTGCTCATAT TGATATTGAC GCTGCTGAAC |
| TTGGCAAAAT | |
| 951 | TGTAAAAACC GATATTCCAA TCCTTTCTGA TTTGAAAGCG |
| GCTTTAAGCA | |
| 1001 | GACTTTTGCA ATTAAATAAG GTCAGGACTG ACTTTAATGA |
| TTGGATTAAA | |
| 1051 | ACTGTCATTG AAAATAAAGA GAAAGCACCA TTTACTTATG |
| AGCCCCAAAA | |
| 1101 | CCATGATATC CGTCCACAGG AAACAATTAA ATTAATTGGA |
| GAATACACTC | |
| 1151 | AAGGAGATGC AATCATTGTA ACTGACGTTG GGCAACATCA |
| AATGTGGGTG | |
| 1201 | GCGCAATATT ATCCTTATAA AAATGCAAGG CAACTTATTA |
| CTTCTGGGGG | |
| 1251 | AATGGGAACG ATGGGCTTTG GCATTCCTGC AGCAATCGGT |
| GCAAAGCTGG | |
| 1301 | CACAGCCAAA TAAAAATGTC ATTGTTTTTG TTGGCGATGG |
| TGGCTTTCAA | |
| 1351 | ATGACTAATC AAGAATTAGC ATTACTTAAT GGCTACGGTA |
| TTGCAATCAA | |
| 1401 | AGTTGTGCTG ATTAATAATC ATTCATTGGG AATGGTACGT |
| CAATGGCAAG | |
| 1451 | AATCATTCTA TGAAGAGCGA CGTTCACAAT CGGTTTTTGA |

SEQUENCE LISTING

```
      TGTTGAACCC
1501  AATTTTCAAT TGTTAGCCGA AGCTTATGGC ATCAAACATG
      TTAAGTTAGA
1551  TAATCCAAAA ACTTTGGCTG ATGATTAAAA AATTATTACA
      GAAGATGAGC
1601  CAATGCTTAT TGAAGTTCTA ATTTCAAAAT CTGAGCATGT
      TTTACCAATG
1651  ATACCAGCTG GATTACACAA TGACGAAATG ATTGGACTTC
      ATTTTACTGA
1701  TAAGAATGAG GAGATAGATA ATGCGTAG
``` ilvn    Length: 477    September 22, 1993    11:09    Type: N
Check: 6061 . .

```
      1     ATGCGTAGAA TGATTATCGC AAAACTTCAT AACGTGACAG
      GAATTATGAA
      51    TCGATTTACC GCCGTTCTCA ATCGAAGGCA AGTGAACATT
      CTCTCAATTA
      101   CCGCTGGAGT TACAGAAAGT CAAGACTTAA CTCATACCAC
      TTTTGTTATT
      151   GAAGTTGATC ATCTTGATGA AGTAGAACAA ATCATTAAAC
      AATTAAATCG
      201   CTTAATAGAT GTAATTGAAG TAGCTGATAT TACTGATTTT
      CCTCATGTAG
      251   AACGTGAAGT CGTCTTGATT AAAGTATCAG CTCCACCGAC
      CATTAGGGCA
      301   GAAATTTTTA CAATGATTGA ACCTTTTAGA GTAAATGTAG
      TTGATGTCAA
      351   TCTGGAAAAT GTCACCATTC AATTAACGGG TGATTCAGCA
      AAAATCGAAG
      401   CACTTATTGA GGTTGTTAGT CCTTATGGCA TTCTAAATAT
      GGCTCGGACA
      451   GGTAGTGCAG GTTTTGAGCG TGGCTAA
``` ilvbn    Length: 2231    September 22, 1993    11:12    Type: N
Check: 7704 . .

```
      1     ATTTATAGAA AGGTTTGAAT GAAAAAAATA AAGTTAGAAA
      AACCTACTTC
      51    CGGTTCCCAA CTTGTTCTCC AAACCTTAAA AGAACTTGGA
      GTAGAAATTA
      101   TTTTTGGTTA TCCTGGTGGG GCCATGCTCC CCTTGTATGA
      TGCGATTCAT
      151   AATTTTGAAG GAATTCAACA TATTTTAGCC CGTCATGAGC
      AAGGAGCAAC
      201   GCATGAAGCC GAAGGTTACG CTAAATCGTC TGGTAAAGTT
      GGTGTCGTCG
      251   TTGTTACGTC AGGACCAGGA GCGACTAATG CAGTAACCGG
      AATTGCTGAC
      301   GCTTATCTTG ATTCAGTCCC ATTGTTAGTT TTCACAGGTC
      AAGTTGGCCG
      351   TCAGTCAATT GGTAAAGATG CTTTTCAAGA AGCAGATACT
      GTTGGAATTA
      401   CAGCCCCAAT TACAAAATAT AATTATCAAA TTAGGGAAAC
      CGCAGATATT
      451   CCAAGAATTG TTACAGAAGC CTATTATTTG GCAAGGACAG
      GACGTCCTGG
      501   ACCAGTAGAA ATTGATTTAC CAAAAGATGT TTCCACCCTT
      GAAGTCACTG
      551   AAATTAATGA CCCAAGCTTG AATCTTCCTC ATTATCACGA
      AAGTGAAAAA
      601   GCGACTGATG AACAATTGCA AGAATTACTG ACAGAACTTT
      CTGTCAGTAA
      651   AAAACCAGTC ATTATTGCTG GCGGAGGAAT TAATTATTCT
      GGCTCAGTTG
      701   ATATTTTCAG AGCATTTGTC GAAAAATATC AAATTCCAGT
      TGTTTCTACA
      751   TTGCTTGGCT TAGGAACATT ACCAATCAGC CACGAATTGC
      AACTAGGAAT
      801   GGCAGGAATG CACGGTTCAT ACGCTGCAAA TATGGCTTTA
      GTTGAAGCTG
      851   ACTATATTAT TAATTTGGGA TCACGTTTTG ACGATAGAGT
      TGTATCCAAT
      901   CCTGCAAAAT TTGCTAAAAA TGCTGTCGTT GCTCATATTG
      ATATTGACGC
      951   TGCTGAACTT GGCAAAATTG TAAAAACCGA TATTCCAATC
      CTTTCTGATT
      1001  TGAAAGCGGC TTTAAGCAGA CTTTTGCAAT TAAATAAGGT
      CAGGACTGAC
      1051  TTTAATGATT GGATTAAAAC TGTCATTGAA AATAAAGAGA
      AAGCACCATT
      1101  TACTTATGAG CCCCAAAACC ATGATATCCG TCCACAGGAA
```

SEQUENCE LISTING

| | | |
|---|---|---|
| ACAATTAAAT | | |
| 1151 | TAATTGGAGA ATACACTCAA GGAGATGCAA TCATTGTAAC | |
| TGACGTTGGG | | |
| 1201 | CAACATCAAA TGTGGGTGGC GCAATATTAT CCTTATAAAA | |
| ATGCAAGGCA | | |
| 1251 | ACTTATTACT TCTGGGGGAA TGGGAACGAT GGGCTTTGGC | |
| ATTCCTGCAG | | |
| 1301 | CAATCGGTGC AAAGCTGGCA CAGCCAAATA AAAATGTCAT | |
| TGTTTTTGTT | | |
| 1351 | GGCGATGGTG GCTTTCAAAT GACTAATCAA GAATTAGCAT | |
| TACTTAATGG | | |
| 1401 | CTACGGTATT GCAATCAAAG TTGTGCTGAT TAATAATCAT | |
| TCATTGGGAA | | |
| 1451 | TGGTACGTCA ATGGCAAGAA TCATTCTATG AAGAGCGACG | |
| TTCACAATCG | | |
| 1501 | GTTTTTGATG TTGAACCCAA TTTTCAATTG TTAGCCGAAG | |
| CTTATGGCAT | | |
| 1551 | CAAACATGTT AAGTTAGATA ATCCAAAAAC TTTGGCTGAT | |
| GATTTAAAAA | | |
| 1601 | TTATTACAGA AGATGAGCCA ATGCTTATTG AAGTTCTAAT | |
| TTCAAAATCT | | |
| 1651 | GAGCATGTTT TACCAATGAT ACCAGCTGGA TTACACAATG | |
| ACGAAATGAT | | |
| 1701 | TGGACTTCAT TTTACTGATA AGAATGAGGA GATAGATAAT | |
| GCGTAGAATG | | |
| 1751 | ATTATCGCAA AACTTCATAA CGTGACAGGA ATTATGAATC | |
| GATTTACCGC | | |
| 1801 | CGTTCTCAAT CGAAGGCAAG TGAACATTCT CTCAATTACC | |
| GCTGGAGTTA | | |
| 1851 | CAGAAAGTCA AGACTTAACT CATACCACTT TTGTTATTGA | |
| AGTTGATCAT | | |
| 1901 | CTTGATGAAG TAGAACAAAT CATTAAACAA TTAAATCGCT | |
| TAATAGATGT | | |
| 1951 | AATTGAAGTA GCTGATATTA CTGATTTTCC TCATGTAGAA | |
| CGTGAAGTCG | | |
| 2001 | TCTTGATTAA AGTATCAGCT CCACCGACCA TTAGGGCAGA | |
| AATTTTTACA | | |
| 2051 | ATGATTGAAC CTTTTAGAGT AAATGTAGTT GATGTCAATC | |
| TGGAAAATGT | | |
| 2101 | CACCATTCAA TTAACGGGTG ATTCAGCAAA AATCGAAGCA | |
| CTTATTGAGG | | |
| 2151 | TTGTTAGTCC TTATGGCATT CTAAATATGG CTCGGACAGG | |
| TAGTGCAGGT | | |
| 2201 | TTTGAGCGTG GCTAAATTTA AATAAGTTAA C | |

---

We claim:

1. An isolated nucleic acid molecule encoding a subunit of an α-acetolactate synthase, said nucleic acid molecule having a nucleotide sequence as shown in SEQ ID NO: 12.

2. An isolated nucleic acid molecule encoding a subunit of an α-acetolactate synthase, said nucleic acid molecule having a nucleotide sequence as shown in SEQ ID NO: 13.

3. An isolated nucleic acid molecule encoding a subunit of an α-acetolactate synthase, said nucleic acid molecule encoding an amino acid sequence as shown in SEQ ID NO: 7.

4. An isolated nucleic acid molecule encoding a subunit of an α-acetolactate synthase, said nucleic acid molecule encoding an amino acid sequence as shown in SEQ ID NO: 8.

5. An isolated subunit of an α-acetolactate synthase having an amino acid sequence as shown in SEQ ID NO: 7.

6. An isolated subunit of an α-acetolactate synthase having an amino acid sequence as shown in SEQ ID NO: 8.

7. An isolated α-acetolactate synthase comprising a first subunit having an amino acid sequence as shown in SEQ ID NO: 7 and a second subunit having an amino acid sequence as shown in SEQ ID NO: 8.

8. The isolated nucleic acid molecule of claim 3 further comprising one or more regulatory elements selected from the group consisting of a promoter and a transcription termination signal.

9. An expression vector comprising the nucleic acid molecule of claim 3.

10. A host cell comprising the expression vector of claim 9.

11. A host cell comprising the nucleic acid molecule of claim 3.

12. The host cell of claim 11 wherein a gene coding for lactate dehydrogenase and/or a gene coding for alpha-acetolactate decarboxylase of said host cell are inactivated.

13. The isolated nucleic acid molecule of claim 4 further comprising one or more regulatory elements selected from the group consisting of a promoter and transcription termination signal.

14. An expression vector comprising the nucleic acid molecule of claim 4.

15. A host cell comprising the expression vector of claim 14.

16. A host cell comprising the nucleic acid molecule of claim 4.

17. The host cell of claim 16 wherein a gene coding for lactate dehydrogenase and/or a gene coding for alpha-acetolactate decarboxylase of said host cell are inactivated.

* * * * *

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 513 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: LEUA ( x i ) SEQUENCE DESCRIPTION: SEQ ID NO: 1:

```
Met  Arg  Lys  Ile  Glu  Phe  Phe  Asp  Thr  Ser  Leu  Arg  Asp  Gly  Glu  Gln
 1                  5                        10                       15

Thr  Pro  Gly  Val  Ser  Phe  Ser  Ile  Ser  Glu  Lys  Val  Thr  Ile  Ala  Lys
                20                       25                       30
```

```
Gln Leu Glu Lys Trp Arg Ile Ser Val Ile Glu Ala Gly Phe Ser Ala
         35                  40                  45
Ala Ser Pro Asp Ser Phe Glu Ala Val Lys Gln Ile Ala Asp Ser Leu
         50                  55                  60
Asn Asp Thr Ala Val Thr Ala Leu Ala Arg Cys Val Ile Ser Asp Ile
 65                  70                  75                  80
Asp Lys Ala Val Glu Ala Val Lys Gly Ala Lys Tyr Pro Gln Ile His
                     85                  90                  95
Val Phe Ile Ala Thr Ser Pro Ile His Met Lys Tyr Lys Leu Lys Ile
            100                 105                 110
Ser Pro Glu Glu Val Leu Lys Asn Ile Asp Lys Cys Val Arg Tyr Ala
            115                 120                 125
Arg Glu Arg Val Glu Val Val Glu Phe Ser Pro Glu Asp Ala Thr Arg
        130                 135                 140
Thr Glu Leu Asn Phe Leu Leu Glu Ala Val Gln Thr Ala Val Asp Ala
145                 150                 155                 160
Gly Ala Thr Tyr Ile Asn Ile Pro Asp Thr Val Gly Tyr Thr Thr Pro
                165                 170                 175
Glu Glu Tyr Gly Lys Ile Phe Lys Phe Leu Ile Asp Asn Thr Lys Ser
            180                 185                 190
Asp Arg Glu Ile Ile Phe Ser Pro His Cys His Asp Asp Leu Gly Met
        195                 200                 205
Ala Val Ala Asn Ser Leu Ala Ala Ile Lys Ala Gly Ala Gly Arg Val
    210                 215                 220
Glu Gly Thr Val Asn Gly Ile Gly Glu Arg Ala Gly Asn Ala Ala Leu
225                 230                 235                 240
Glu Glu Ile Ala Val Ala Leu His Ile Arg Lys Asp Phe Tyr Gln Ala
                245                 250                 255
Gln Ser Pro Leu Lys Leu Ser Glu Thr Ala Ala Thr Ala Glu Leu Ile
            260                 265                 270
Ser Gln Phe Ser Gly Ile Ala Ile Pro Lys Asn Lys Ala Ile Val Gly
        275                 280                 285
Ala Asn Ala Phe Ala His Glu Ser Gly Ile His Gln Asp Gly Val Leu
    290                 295                 300
Lys Asn Ala Glu Thr Tyr Glu Ile Ile Thr Pro Glu Leu Val Gly Ile
305                 310                 315                 320
Lys His Asn Ser Leu Pro Leu Gly Lys Leu Ser Gly Arg His Ala Phe
                325                 330                 335
Ser Glu Lys Leu Thr Glu Leu Asn Ile Ala Tyr Asp Asp Glu Ser Leu
            340                 345                 350
Ala Ile Leu Phe Glu Lys Phe Lys Lys Leu Ala Asp Lys Lys Lys Glu
        355                 360                 365
Ile Thr Asp Ala Asp Ile His Ala Leu Phe Thr Gly Glu Thr Val Lys
    370                 375                 380
Asn Leu Ala Gly Phe Ile Leu Asp Asn Val Gln Ile Asp Gly His Lys
385                 390                 395                 400
Ala Leu Val Gln Leu Lys Asn Gln Glu Glu Glu Ile Tyr Val Ser Gln
                405                 410                 415
Gly Glu Gly Ser Gly Ser Val Asp Ala Ile Phe Lys Ala Ile Asp Lys
            420                 425                 430
Val Phe Asn His Gln Leu Lys Leu Ile Ser Tyr Ser Val Asp Ala Val
        435                 440                 445
Thr Asp Gly Ile Asp Ala Gln Ala Thr Thr Leu Val Ser Val Glu Asn
```

|   |   |   |   |   | 450 |   |   |   |   | 455 |   |   |   |   | 460 |   |
|---|---|---|---|---|---|---|---|---|---|---|---|---|---|---|---|---|
| Leu | Ser | Thr | Gly | Thr | Ile | Phe | Asn | Ala | Lys | Gly | Val | Asp | Tyr | Asp | Val |
| 465 |   |   |   |   | 470 |   |   |   |   | 475 |   |   |   |   | 480 |
| Leu | Lys | Gly | Ser | Ala | Ile | Ala | Tyr | Met | Asn | Ala | Asn | Val | Leu | Val | Gln |
|   |   |   |   | 485 |   |   |   |   | 490 |   |   |   |   | 495 |   |
| Lys | Glu | Asn | Leu | Gln | Gly | Lys | Val | Glu | Gln | Ile | Ser | Ala | His | Asp | Gly |
|   |   |   | 500 |   |   |   |   | 505 |   |   |   |   | 510 |   |   |
| Ile |   |   |   |   |   |   |   |   |   |   |   |   |   |   |   |

( 2 ) INFORMATION FOR SEQ ID NO: 2:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: LEUB ( x i ) SEQUENCE DESCRIPTION: SEQ ID NO: 2:

| Leu | Ser | Lys | Lys | Ile | Val | Thr | Leu | Ala | Gly | Asp | Gly | Ile | Gly | Pro | Glu |
|---|---|---|---|---|---|---|---|---|---|---|---|---|---|---|---|
| 1 |   |   |   | 5 |   |   |   |   | 10 |   |   |   |   | 15 |   |
| Ile | Met | Ser | Ala | Gly | Leu | Ser | Val | Leu | Lys | Ala | Val | Ser | Lys | Lys | Ile |
|   |   |   | 20 |   |   |   | 25 |   |   |   |   | 30 |   |   |   |
| Asp | Phe | Glu | Tyr | Glu | Leu | Glu | Ala | Lys | Asp | Phe | Gly | Gly | Ile | Ala | Ile |
|   |   | 35 |   |   |   |   | 40 |   |   |   |   | 45 |   |   |   |
| Asp | Lys | His | Gly | His | Pro | Leu | Pro | Glu | Glu | Thr | Leu | Gln | Ala | Val | Lys |
| 50 |   |   |   |   | 55 |   |   |   |   | 60 |   |   |   |   |   |
| Asn | Ala | Asp | Ala | Ile | Leu | Leu | Ala | Ala | Ile | Gly | His | Pro | Lys | Tyr | Asn |
| 65 |   |   |   |   | 70 |   |   |   |   | 75 |   |   |   |   | 80 |
| Asn | Ala | Lys | Val | Arg | Pro | Glu | Gln | Gly | Leu | Leu | Ala | Leu | Arg | Lys | Glu |
|   |   |   |   | 85 |   |   |   |   | 90 |   |   |   |   | 95 |   |
| Leu | Gly | Leu | Tyr | Ala | Asn | Val | Arg | Pro | Leu | Lys | Ile | Tyr | Pro | Ala | Leu |
|   |   |   | 100 |   |   |   |   | 105 |   |   |   |   | 110 |   |   |
| Lys | Lys | Leu | Ser | Pro | Ile | Arg | Asn | Val | Glu | Asn | Val | Asp | Phe | Leu | Val |
|   |   |   | 115 |   |   |   |   | 120 |   |   |   |   | 125 |   |   |
| Ile | Arg | Glu | Leu | Thr | Gly | Gly | Ile | Tyr | Phe | Gly | Gln | His | Glu | Leu | Ala |
|   | 130 |   |   |   |   | 135 |   |   |   |   | 140 |   |   |   |   |
| Asp | Asp | Lys | Ala | Arg | Asp | Val | Asn | Asp | Tyr | Ser | Ala | Asp | Glu | Ile | Arg |
| 145 |   |   |   |   | 150 |   |   |   |   | 155 |   |   |   |   | 160 |
| Arg | Ile | Leu | His | Phe | Ala | Phe | Lys | Ser | Ala | Gln | Ser | Arg | Pro | Arg | Lys |
|   |   |   |   | 165 |   |   |   |   | 170 |   |   |   |   | 175 |   |
| Leu | Leu | Thr | Ser | Val | Asp | Lys | Gln | Asn | Val | Leu | Ala | Thr | Ser | Lys | Leu |
|   |   |   | 180 |   |   |   |   | 185 |   |   |   |   | 190 |   |   |
| Trp | Arg | Lys | Met | Ala | Asp | Glu | Ile | Ala | Asp | Glu | Tyr | Pro | Asp | Val | Arg |
|   |   | 195 |   |   |   |   | 200 |   |   |   |   | 205 |   |   |   |
| Leu | Glu | His | Gln | Leu | Val | Asp | Ser | Cys | Ala | Met | Leu | Leu | Ile | Thr | Asn |
|   | 210 |   |   |   |   | 215 |   |   |   |   | 220 |   |   |   |   |
| Pro | Gln | Gln | Phe | Asp | Val | Ile | Val | Thr | Glu | Asn | Leu | Phe | Gly | Asp | Ile |
| 225 |   |   |   |   | 230 |   |   |   |   | 235 |   |   |   |   | 240 |
| Leu | Ser | Asp | Glu | Ala | Ser | Ser | Leu | Ala | Gly | Ser | Leu | Gly | Val | Met | Pro |
|   |   |   |   | 245 |   |   |   |   | 250 |   |   |   |   | 255 |   |
| Ser | Ser | Ser | His | Gly | Phe | Asn | Gly | Leu | Ala | Leu | Tyr | Glu | Pro | Ile | His |

|   |   |   |   |   | 260 |   |   |   |   | 265 |   |   |   |   | 270 |   |
|---|---|---|---|---|---|---|---|---|---|---|---|---|---|---|---|---|

Gly Ser Ala Pro Asp Ile Ala Gly Lys Gly Ile Ala Asn Pro Val Ser
275 280 285

Met Ile Leu Ser Ile Ala Met Met Leu Arg Glu Ser Phe Gly Gln Glu
290 295 300

Asp Gly Ala Ala Met Ile Glu Lys Ala Val Thr Gln Thr Phe Thr Asp
305 310 315 320

Gly Ile Leu Thr Lys Asp Leu Gly Gly Thr Ala Thr Thr Lys Glu Met
325 330 335

Thr Glu Ala Ile Leu Lys Asn Cys Gln
340 345

(2) INFORMATION FOR SEQ ID NO: 3:

(i) SEQUENCE CHARACTERISTICS:
        (A) LENGTH: 460 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Lactococcus lactis subsp. lactis
        (C) INDIVIDUAL ISOLATE: LEUC (xi) SEQUENCE DESCRIPTION: SEQ ID NO: 3:

Met Ser Gly Lys Thr Ile Phe Asp Lys Leu Trp Asp Gln His Val Ile
1 5 10 15

Ala Gly Asn Glu Gly Glu Pro Gln Leu Leu Tyr Ile Asp Leu His Val
20 25 30

Ile His Glu Val Thr Ser Pro Gln Ala Phe Gln Gly Leu Arg Glu Ala
35 40 45

Gly Arg Arg Val Arg Arg Lys Asp Leu Thr Tyr Gly Thr Leu Asp His
50 55 60

Asn Val Pro Thr Gln Asn Ile Phe Asn Ile Gln Asp Leu Ile Ser Lys
65 70 75 80

Lys Gln Ile Asp Thr Phe Thr Lys Asn Val Lys Glu Phe Asp Val Pro
85 90 95

Ala Glu Thr His Gly Gly Lys Gly Gln Gly Ile Val His Met Val Ala
100 105 110

Pro Glu Ser Gly Arg Thr Gln Pro Gly Lys Thr Ile Val Cys Gly Asp
115 120 125

Ser His Thr Ala Thr Asn Gly Ala Phe Gly Ala Ile Ala Phe Gly Ile
130 135 140

Gly Thr Ser Glu Val Glu His Val Leu Ala Thr Gln Thr Ile Trp Gln
145 150 155 160

Val Lys Pro Lys Arg Met Lys Ile Glu Phe Gln Gly His Pro Gln Lys
165 170 175

Gly Ile Tyr Ser Lys Asp Phe Ile Leu Ala Leu Ile Ala Lys Tyr Gly
180 185 190

Val Asp Ala Gly Val Gly Tyr Ala Val Glu Tyr Ser Gly Asp Ala Ile
195 200 205

Ser Asp Leu Ser Met Glu Glu Arg Met Thr Ile Cys Asn Met Ser Ile
210 215 220

Glu Phe Gly Ala Lys Ile Gly Leu Met Asn Pro Asp Glu Lys Thr Tyr
225 230 235 240

-continued

```
Asp  Tyr  Val  Lys  Gly  Arg  Glu  His  Ala  Pro  Lys  Asn  Phe  Asp  Glu  Ala
               245                250                          255

Val  Ser  Lys  Trp  Glu  Lys  Leu  Val  Ser  Asp  Ser  Asp  Ala  Gln  Tyr  Asp
               260                265                          270

Lys  Ile  Leu  Ser  Leu  Asp  Val  Ser  Gln  Leu  Lys  Pro  Met  Val  Thr  Trp
               275                280                          285

Gly  Thr  Asn  Pro  Gly  Met  Gly  Leu  Glu  Phe  Gly  Glu  Lys  Phe  Pro  Glu
               290                295                          300

Ile  Asn  Asn  Asp  Leu  Asn  Tyr  Glu  Arg  Ala  Tyr  Gln  Tyr  Met  Asp  Leu
305                           310                315                          320

Lys  Pro  Gly  Gln  Thr  Ala  Ser  Asp  Ile  Asp  Leu  Gly  Tyr  Ile  Phe  Ile
               325                330                          335

Gly  Ser  Cys  Thr  Asn  Ala  Arg  Leu  Gly  Asp  Leu  Glu  Glu  Ala  Ala  Lys
               340                345                          350

Ile  Ile  Gly  Asp  Arg  His  Ile  Ala  Asp  Gly  Leu  Thr  Gly  Ile  Val  Val
               355                360                          365

Pro  Gly  Ser  Arg  Pro  Val  Lys  Glu  Ala  Ala  Glu  Ala  Gln  Gly  Leu  Asp
               370                375                          380

Lys  Ile  Phe  Lys  Glu  Ala  Gly  Phe  Glu  Trp  Arg  Glu  Pro  Gly  Cys  Ser
385                           390                395                          400

Ala  Cys  Leu  Gly  Met  Asn  Pro  Asp  Gln  Ile  Pro  Glu  Tyr  Val  His  Cys
               405                410                          415

Ala  Ser  Thr  Ser  Asn  Arg  Asn  Phe  Glu  Gly  Arg  Gln  Gly  His  Asn  Ala
               420                425                          430

Arg  Thr  His  Leu  Cys  Ser  Pro  Ala  Met  Ala  Ala  Ala  Ala  Ile  Ile  Ala
               435                440                          445

Gly  Lys  Phe  Val  Asp  Val  Arg  Met  Leu  Val  Thr  Asp
               450                455                460
```

(2) INFORMATION FOR SEQ ID NO: 4:

(i) SEQUENCE CHARACTERISTICS:
        (A) LENGTH: 191 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Lactococcus lactis subsp. lactis
        (C) INDIVIDUAL ISOLATE: LEUD (xi) SEQUENCE DESCRIPTION: SEQ ID NO: 4:

```
Met  Glu  Lys  Phe  Thr  Ile  Tyr  Lys  Gly  Thr  Ser  Val  Pro  Val  Met  Asn
1                   5                         10                          15

Asp  Asn  Ile  Asp  Thr  Asp  Gln  Ile  Ile  Pro  Lys  Gln  Phe  Leu  Lys  Ala
               20                 25                          30

Ile  Asp  Lys  Lys  Gly  Phe  Gly  Lys  Asn  Leu  Phe  Tyr  Glu  Trp  Arg  Tyr
               35                 40                          45

Leu  Lys  Asp  Tyr  Asp  Glu  Asn  Pro  Asp  Phe  Ile  Leu  Asn  Ala  Pro  Lys
50                  55                         60

Tyr  Lys  Lys  Ala  Ser  Leu  Leu  Ile  Ser  Gly  Asp  Asn  Phe  Gly  Ser  Gly
65                  70                         75                          80

Ser  Ser  Arg  Glu  His  Ala  Ala  Trp  Ala  Leu  Ser  Asp  Tyr  Gly  Phe  Arg
               85                 90                          95

Ala  Ile  Ile  Ala  Gly  Ser  Tyr  Ser  Asp  Ile  Phe  Tyr  Asn  Asn  Ala  Leu
               100                105                         110
```

```
Lys  Asn  Gly  Leu  Leu  Pro  Ile  Lys  Gln  Pro  Arg  Glu  Val  Leu  Asn  Gln
               115                      120                     125

Leu  Thr  Lys  Leu  Ser  Ser  Gln  Glu  Ile  Thr  Ile  Asp  Leu  Pro  His
     130                      135                     140

Gln  Leu  Ile  Ile  Thr  Ser  Leu  Gly  Asp  Phe  His  Phe  Glu  Ile  Asp  Pro
145                           150                     155                     160

Ile  Trp  Lys  Asp  Lys  Leu  Ile  Asn  Gly  Leu  Asp  Asp  Ile  Gly  Ile  Thr
               165                      170                     175

Leu  Gln  Tyr  Glu  Glu  Ala  Ile  Ser  Ala  Tyr  Glu  Gln  Lys  Asn  Gln
               180                      185                     190
```

( 2 ) INFORMATION FOR SEQ ID NO: 5:

( i ) SEQUENCE CHARACTERISTICS:
        ( A ) LENGTH: 259 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: ORF2

( x i ) SEQUENCE DESCRIPTION: SEQ ID NO: 5:

```
Met  Thr  Ile  Ile  Asn  Leu  Lys  Asn  Val  Asn  Leu  Thr  Arg  Asn  Lys  Lys
1                        5                       10                      15

Glu  Ile  Leu  Lys  Asp  Ile  Thr  Trp  Lys  Val  Asn  Pro  Gly  Glu  Asn  Trp
               20                       25                      30

Val  Ile  Leu  Gly  Leu  Asn  Gly  Ser  Gly  Lys  Ser  Ser  Leu  Leu  Lys  Leu
               35                       40                      45

Ile  Leu  Ala  Glu  Glu  Trp  Lys  Thr  Ser  Gly  Glu  Ile  Thr  Val  Leu  Asn
     50                       55                      60

Thr  Gln  Phe  Arg  Asn  Gly  Glu  Ile  Pro  Lys  Leu  Arg  Lys  Arg  Ile  Ser
65                       70                      75                      80

Val  Val  Gly  Ser  Phe  Ile  Ala  Glu  Arg  Phe  Gln  Pro  Asn  Ile  Lys  Ala
               85                       90                      95

Glu  Asn  Leu  Val  Tyr  Thr  Gly  Lys  Phe  Asn  Ser  Ser  Met  Leu  Tyr  Lys
               100                      105                     110

Pro  Tyr  Thr  Asp  Gln  Glu  Leu  Asp  Glu  Ala  Arg  Gln  Leu  Leu  Arg  Gln
               115                      120                     125

Met  Gly  Ala  Lys  Ser  Leu  Ile  Gly  Arg  Asn  Tyr  Ala  Ser  Leu  Ser  Gln
     130                      135                     140

Gly  Glu  Lys  Gln  Val  Leu  Leu  Ile  Ala  Arg  Ser  Leu  Ile  Leu  Lys  Pro
145                           150                     155                     160

Glu  Leu  Leu  Ile  Leu  Asp  Glu  Ala  Thr  Asn  Gly  Leu  Asp  Leu  Phe  Ala
                    165                      170                     175

Lys  Glu  Lys  Leu  Leu  Lys  Gln  Leu  Gln  Gln  Ile  Asn  Gln  Leu  Lys  Thr
               180                      185                     190

Ala  Pro  Thr  Leu  Ile  Tyr  Ile  Ser  His  His  Pro  Asp  Glu  Ile  Thr  Asp
               195                      200                     205

Ile  Phe  Thr  His  Leu  Leu  Leu  Leu  Arg  Glu  Gly  Lys  Val  Ile  Gln  Ser
     210                      215                     220

Gly  Lys  Lys  Glu  Asn  Leu  Leu  Asn  Glu  Lys  Ile  Leu  Thr  Asp  Phe  Tyr
225                      230                     235                     240

Gln  Glu  Lys  Val  Glu  Val  His  Arg  Phe  Glu  Gln  Lys  Tyr  Phe  Val  Ile
```

Pro Ala Asn (2) INFORMATION FOR SEQ ID NO: 6:

(i) SEQUENCE CHARACTERISTICS:
        (A) LENGTH: 570 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Lactococcus lactis subsp. lactis
        (C) INDIVIDUAL ISOLATE: ILVD (xi) SEQUENCE DESCRIPTION: SEQ ID NO: 6:

```
Met Glu Phe Lys Tyr Asn Gly Lys Val Glu Ser Val Glu Leu Asn Lys
  1               5                  10                  15

Tyr Ser Lys Thr Leu Thr Pro Arg Ser Thr Gln Pro Ala Thr Gln Ala
                 20                  25                  30

Met Tyr Tyr Gly Ile Gly Phe Lys Asp Glu Asp Phe Lys Lys Ala Gln
             35                  40                  45

Val Gly Ile Val Ser Met Asp Trp Asp Gly Asn Pro Cys Asn Met His
         50                  55                  60

Leu Gly Thr Leu Gly Ser Lys Ile Lys Ser Ser Val Asn Gln Thr Asp
 65                  70                  75                  80

Gly Leu Ile Gly Leu Gln Phe His Thr Ile Gly Val Ser Asp Gly Ile
                 85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
            115                 120                 125

Ile Val Ala Ile Pro Gly Cys Asp Lys Asn Met Pro Gly Ser Ile Ile
        130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
                165                 170                 175

Phe Glu Ala Leu Gly Gln Lys Ile Thr Gly Asn Ile Ser Asp Glu Asp
            180                 185                 190

Tyr His Gly Val Ile Cys Asn Ala Ile Pro Gly Gln Gly Ala Cys Gly
        195                 200                 205

Gly Met Tyr Thr Ala Asn Thr Leu Ala Ala Ala Ile Glu Thr Leu Gly
210                 215                 220

Met Ser Leu Pro Tyr Ser Ser Asn Pro Ala Val Ser Gln Glu Lys
225                 230                 235                 240

Gln Glu Glu Cys Asp Asp Ile Gly Leu Ala Ile Lys Asn Leu Leu Glu
                245                 250                 255

Lys Asp Ile Lys Pro Ser Asp Ile Met Thr Lys Glu Ala Phe Glu Asn
            260                 265                 270

Ala Ile Thr Ile Val Met Val Leu Gly Gly Ser Thr Asn Ala Val Leu
        275                 280                 285

His Ile Ile Ala Met Ala Asn Ala Ile Gly Val Glu Ile Thr Gln Asp
        290                 295                 300

Asp Phe Gln Arg Ile Ser Asp Ile Ile Pro Val Leu Gly Asp Phe Lys
```

| | | | | | | | | | | | | | | | |
|---|---|---|---|---|---|---|---|---|---|---|---|---|---|---|---|
| 305 | | | | | 310 | | | | | 315 | | | | | 320 |
| Pro | Ser | Gly | Lys | Tyr | Met | Met | Glu | Asp | Leu | His | Lys | Ile | Gly | Gly | Leu |
| | | | | 325 | | | | | 330 | | | | | 335 | |
| Pro | Ala | Val | Leu | Lys | Tyr | Leu | Leu | Lys | Glu | Gly | Lys | Leu | His | Gly | Asp |
| | | | 340 | | | | | 345 | | | | | 350 | | |
| Cys | Leu | Thr | Val | Thr | Gly | Lys | Thr | Leu | Ala | Glu | Asn | Val | Glu | Thr | Ala |
| | | 355 | | | | | 360 | | | | | 365 | | | |
| Leu | Asp | Leu | Asp | Phe | Asp | Ser | Gln | Asp | Ile | Met | Arg | Pro | Leu | Lys | Asn |
| | 370 | | | | | 375 | | | | | 380 | | | | |
| Pro | Ile | Lys | Ala | Thr | Gly | His | Leu | Gln | Ile | Leu | Tyr | Gly | Asn | Leu | Ala |
| 385 | | | | | 390 | | | | | 395 | | | | | 400 |
| Gln | Gly | Gly | Ser | Val | Ala | Lys | Ile | Ser | Gly | Lys | Glu | Gly | Glu | Phe | Phe |
| | | | | 405 | | | | | 410 | | | | | 415 | |
| Lys | Gly | Thr | Ala | Arg | Val | Phe | Asp | Gly | Glu | Gln | His | Phe | Ile | Asp | Gly |
| | | | 420 | | | | | 425 | | | | | 430 | | |
| Ile | Glu | Ser | Gly | Arg | Leu | His | Ala | Gly | Asp | Val | Ala | Val | Ile | Arg | Asn |
| | | 435 | | | | | 440 | | | | | 445 | | | |
| Ile | Gly | Pro | Val | Gly | Gly | Pro | Gly | Met | Pro | Glu | Met | Leu | Lys | Pro | Thr |
| | 450 | | | | | 455 | | | | | 460 | | | | |
| Ser | Ala | Leu | Ile | Gly | Ala | Gly | Leu | Gly | Lys | Ser | Cys | Ala | Leu | Ile | Thr |
| 465 | | | | | 470 | | | | | 475 | | | | | 480 |
| Asp | Gly | Arg | Phe | Ser | Gly | Gly | Thr | His | Gly | Phe | Val | Val | Gly | His | Ile |
| | | | | 485 | | | | | 490 | | | | | 495 | |
| Val | Pro | Glu | Ala | Val | Glu | Gly | Gly | Leu | Ile | Gly | Leu | Val | Glu | Asp | Asp |
| | | | 500 | | | | | 505 | | | | | 510 | | |
| Asp | Ile | Ile | Glu | Ile | Asp | Ala | Val | Asn | Asn | Ser | Ile | Ser | Leu | Lys | Val |
| | | 515 | | | | | 520 | | | | | 525 | | | |
| Ser | Asn | Glu | Glu | Ile | Ala | Lys | Arg | Arg | Ala | Asn | Tyr | Gln | Lys | Pro | Thr |
| | 530 | | | | | 535 | | | | | 540 | | | | |
| Pro | Lys | Ala | Thr | Arg | Gly | Val | Leu | Ala | Lys | Phe | Ala | Lys | Leu | Thr | Arg |
| 545 | | | | | 550 | | | | | 555 | | | | | 560 |
| Pro | Ala | Ser | Glu | Gly | Cys | Val | Thr | Asp | Leu | | | | | | |
| | | | | 565 | | | | | 570 | | | | | | |

( 2 ) INFORMATION FOR SEQ ID NO: 7:

( i ) SEQUENCE CHARACTERISTICS:
        ( A ) LENGTH: 575 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: ILVB ( x i ) SEQUENCE DESCRIPTION: SEQ ID NO: 7:

| | | | | | | | | | | | | | | | |
|---|---|---|---|---|---|---|---|---|---|---|---|---|---|---|---|
| Met | Lys | Lys | Ile | Lys | Leu | Glu | Lys | Pro | Thr | Ser | Gly | Ser | Gln | Leu | Val |
| 1 | | | | 5 | | | | | 10 | | | | | 15 | |
| Leu | Gln | Thr | Leu | Lys | Glu | Leu | Gly | Val | Glu | Ile | Ile | Phe | Gly | Tyr | Pro |
| | | | 20 | | | | | 25 | | | | | 30 | | |
| Gly | Gly | Ala | Met | Leu | Pro | Leu | Tyr | Asp | Ala | Ile | His | Asn | Phe | Glu | Gly |
| | | | 35 | | | | | 40 | | | | | 45 | | |
| Ile | Gln | His | Ile | Leu | Ala | Arg | His | Glu | Gln | Gly | Ala | Thr | His | Glu | Ala |
| | | 50 | | | | | 55 | | | | | 60 | | | |

| Glu 65 | Gly | Tyr | Ala | Lys 70 | Ser | Ser | Gly | Lys 75 | Val | Gly | Val | Val | Val | Val | Thr 80 |
| Ser | Gly | Pro | Gly | Ala 85 | Thr | Asn | Ala | Val | Thr 90 | Gly | Ile | Ala | Asp | Ala 95 | Tyr |
| Leu | Asp | Ser | Val | Pro 100 | Leu | Leu | Val | Phe | Thr 105 | Gly | Gln | Val | Gly | Arg 110 | Gln |
| Ser | Ile | Gly 115 | Lys | Asp | Ala | Phe | Gln 120 | Glu | Ala | Asp | Thr | Val 125 | Gly | Ile | Thr |
| Ala | Pro 130 | Ile | Thr | Lys | Tyr | Asn 135 | Tyr | Gln | Ile | Arg | Glu 140 | Thr | Ala | Asp | Ile |
| Pro 145 | Arg | Ile | Val | Thr | Glu 150 | Ala | Tyr | Tyr | Leu | Ala 155 | Arg | Thr | Gly | Arg | Pro 160 |
| Gly | Pro | Val | Glu | Ile 165 | Asp | Leu | Pro | Lys | Asp 170 | Val | Ser | Thr | Leu | Glu 175 | Val |
| Thr | Glu | Ile | Asn 180 | Asp | Pro | Ser | Leu | Asn 185 | Leu | Pro | His | Tyr | His 190 | Glu | Ser |
| Glu | Lys | Ala 195 | Thr | Asp | Glu | Gln | Leu 200 | Gln | Glu | Leu | Leu | Thr 205 | Glu | Leu | Ser |
| Val | Ser 210 | Lys | Lys | Pro | Val | Ile 215 | Ile | Ala | Gly | Gly | Gly 220 | Ile | Asn | Tyr | Ser |
| Gly 225 | Ser | Val | Asp | Ile | Phe 230 | Arg | Ala | Phe | Val | Glu 235 | Lys | Tyr | Gln | Ile | Pro 240 |
| Val | Val | Ser | Thr | Leu 245 | Leu | Gly | Leu | Gly | Thr 250 | Leu | Pro | Ile | Ser | His 255 | Glu |
| Leu | Gln | Leu | Gly 260 | Met | Ala | Gly | Met | His 265 | Gly | Ser | Tyr | Ala | Ala 270 | Asn | Met |
| Ala | Leu | Val 275 | Glu | Ala | Asp | Tyr | Ile 280 | Ile | Asn | Leu | Gly | Ser 285 | Arg | Phe | Asp |
| Asp | Arg 290 | Val | Val | Ser | Asn | Pro 295 | Ala | Lys | Phe | Ala | Lys 300 | Asn | Ala | Val | Val |
| Ala 305 | His | Ile | Asp | Ile | Asp 310 | Ala | Ala | Glu | Leu | Gly 315 | Lys | Ile | Val | Lys | Thr 320 |
| Asp | Ile | Pro | Ile | Leu 325 | Ser | Asp | Leu | Lys | Ala 330 | Ala | Leu | Ser | Arg | Leu 335 | Leu |
| Gln | Leu | Asn | Lys 340 | Val | Arg | Thr | Asp | Phe 345 | Asn | Asp | Trp | Ile | Lys 350 | Thr | Val |
| Ile | Glu | Asn 355 | Lys | Glu | Lys | Ala | Pro 360 | Phe | Thr | Tyr | Glu | Pro 365 | Gln | Asn | His |
| Asp | Ile 370 | Arg | Pro | Gln | Glu | Thr 375 | Ile | Lys | Leu | Ile | Gly 380 | Glu | Tyr | Thr | Gln |
| Gly 385 | Asp | Ala | Ile | Ile | Val 390 | Thr | Asp | Val | Gly | Gln 395 | His | Gln | Met | Trp | Val 400 |
| Ala | Gln | Tyr | Tyr | Pro 405 | Tyr | Lys | Asn | Ala | Arg 410 | Gln | Leu | Ile | Thr | Ser 415 | Gly |
| Gly | Met | Gly | Thr 420 | Met | Gly | Phe | Gly | Ile 425 | Pro | Ala | Ala | Ile | Gly 430 | Ala | Lys |
| Leu | Ala | Gln 435 | Pro | Asn | Lys | Asn | Val 440 | Ile | Val | Phe | Val | Gly 445 | Asp | Gly | Gly |
| Phe | Gln 450 | Met | Thr | Asn | Gln | Glu 455 | Leu | Ala | Leu | Leu | Asn 460 | Gly | Tyr | Gly | Ile |
| Ala 465 | Ile | Lys | Val | Val | Leu 470 | Ile | Asn | Asn | His | Ser 475 | Leu | Gly | Met | Val | Arg 480 |
| Gln | Trp | Gln | Glu | Ser 485 | Phe | Tyr | Glu | Glu | Arg 490 | Arg | Ser | Gln | Ser | Val 495 | Phe |

```
    Asp  Val  Glu  Pro  Asn  Phe  Gln  Leu  Leu  Ala  Glu  Ala  Tyr  Gly  Ile  Lys
                   500                      505                      510

His  Val  Lys  Leu  Asp  Asn  Pro  Lys  Thr  Leu  Ala  Asp  Asp  Leu  Lys  Ile
              515                      520                      525

Ile  Thr  Glu  Asp  Glu  Pro  Met  Leu  Ile  Glu  Val  Leu  Ile  Ser  Lys  Ser
              530                      535                      540

Glu  His  Val  Leu  Pro  Met  Ile  Pro  Ala  Gly  Leu  His  Asn  Asp  Glu  Met
    545                      550                      555                      560

Ile  Gly  Leu  His  Phe  Thr  Asp  Lys  Asn  Glu  Ile  Asp  Asn  Ala
                        565                      570                      575
```

( 2 ) INFORMATION FOR SEQ ID NO: 8:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: ILVN ( x i ) SEQUENCE DESCRIPTION: SEQ ID NO: 8:

```
    Met  Arg  Arg  Met  Ile  Ile  Ala  Lys  Leu  His  Asn  Val  Thr  Gly  Ile  Met
    1                   5                        10                       15

Asn  Arg  Phe  Thr  Ala  Val  Leu  Asn  Arg  Arg  Gln  Val  Asn  Ile  Leu  Ser
                   20                      25                       30

Ile  Thr  Ala  Gly  Val  Thr  Glu  Ser  Gln  Asp  Leu  Thr  His  Thr  Thr  Phe
              35                      40                       45

Val  Ile  Glu  Val  Asp  His  Leu  Asp  Glu  Val  Glu  Gln  Ile  Ile  Lys  Gln
              50                      55                       60

Leu  Asn  Arg  Leu  Ile  Asp  Val  Ile  Glu  Val  Ala  Asp  Ile  Thr  Asp  Phe
    65                       70                       75                       80

Pro  His  Val  Glu  Arg  Glu  Val  Val  Leu  Ile  Lys  Val  Ser  Ala  Pro  Pro
                        85                       90                       95

Thr  Ile  Arg  Ala  Glu  Ile  Phe  Thr  Met  Ile  Glu  Pro  Phe  Arg  Val  Asn
                   100                     105                      110

Val  Val  Asp  Val  Asn  Leu  Glu  Asn  Val  Thr  Ile  Gln  Leu  Thr  Gly  Asp
                   115                     120                      125

Ser  Ala  Lys  Ile  Glu  Ala  Leu  Ile  Glu  Val  Val  Ser  Pro  Tyr  Gly  Ile
              130                     135                      140

Leu  Asn  Met  Ala  Arg  Thr  Gly  Ser  Ala  Gly  Phe  Glu  Arg  Gly
    145                     150                      155
```

( 2 ) INFORMATION FOR SEQ ID NO: 9:

( i ) SEQUENCE CHARACTERISTICS:
        ( A ) LENGTH: 344 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: ILVC ( x i ) SEQUENCE DESCRIPTION: SEQ ID NO: 9:

| Met<br>1 | Ala | Val | Thr | Met<br>5 | Tyr | Tyr | Glu | Asp | Asp<br>10 | Val | Glu | Val | Ser | Ala<br>15 | Leu |
|---|---|---|---|---|---|---|---|---|---|---|---|---|---|---|---|
| Ala | Gly | Lys | Gln<br>20 | Ile | Ala | Val | Ile | Gly<br>25 | Tyr | Gly | Ser | Gln | Gly<br>30 | His | Ala |
| His | Ala | Gln<br>35 | Asn | Leu | Arg | Asp | Ser<br>40 | Gly | His | Asn | Val | Ile<br>45 | Ile | Gly | Val |
| Arg | His<br>50 | Gly | Lys | Ser | Phe | Asp<br>55 | Lys | Ala | Lys | Glu | Asp<br>60 | Gly | Phe | Glu | Thr |
| Phe<br>65 | Glu | Val | Gly | Glu | Ala<br>70 | Val | Ala | Lys | Ala | Asp<br>75 | Val | Ile | Met | Val | Leu<br>80 |
| Ala | Pro | Asp | Glu | Leu<br>85 | Gln | Gln | Ser | Ile | Tyr<br>90 | Glu | Glu | Asp | Ile | Lys<br>95 | Pro |
| Asn | Leu | Lys | Ala<br>100 | Gly | Ser | Ala | Leu | Gly<br>105 | Phe | Ala | His | Gly | Phe<br>110 | Asn | Ile |
| His | Phe | Gly<br>115 | Tyr | Ile | Lys | Val | Pro<br>120 | Glu | Asp | Val | Asp | Val<br>125 | Phe | Met | Val |
| Ala | Pro<br>130 | Lys | Ala | Pro | Gly | His<br>135 | Leu | Val | Arg | Arg | Thr<br>140 | Tyr | Thr | Glu | Gly |
| Phe<br>145 | Gly | Thr | Pro | Ala | Leu<br>150 | Phe | Val | Ser | His | Gln<br>155 | Asn | Ala | Ser | Gly | His<br>160 |
| Ala | Arg | Glu | Ile | Ala<br>165 | Met | Asp | Trp | Ala | Lys<br>170 | Gly | Ile | Gly | Cys | Ala<br>175 | Arg |
| Val | Gly | Ile | Ile | Glu<br>180 | Thr | Thr | Phe | Lys | Glu<br>185 | Glu | Thr | Glu | Glu | Asp<br>190 | Leu |
| Phe | Gly | Glu | Gln<br>195 | Ala | Val | Leu | Cys | Gly<br>200 | Gly | Leu | Thr | Ala | Leu<br>205 | Val | Glu |
| Ala | Gly<br>210 | Phe | Glu | Thr | Leu | Thr<br>215 | Glu | Ala | Gly | Tyr | Ala<br>220 | Gly | Glu | Leu | Ala |
| Tyr<br>225 | Phe | Glu | Val | Leu | His<br>230 | Glu | Met | Lys | Leu | Ile<br>235 | Val | Asp | Leu | Met | Tyr<br>240 |
| Glu | Gly | Gly | Phe | Thr<br>245 | Lys | Met | Arg | Gln | Ser<br>250 | Ile | Ser | Asn | Thr | Ala<br>255 | Glu |
| Phe | Gly | Asp | Tyr<br>260 | Val | Thr | Gly | Pro | Arg<br>265 | Ile | Ile | Thr | Asp | Glu<br>270 | Val | Lys |
| Lys | Asn | Met<br>275 | Lys | Leu | Val | Leu | Ala<br>280 | Asp | Ile | Gln | Ser | Gly<br>285 | Lys | Phe | Ala |
| Gln | Asp<br>290 | Phe | Val | Asp | Asp | Phe<br>295 | Lys | Ala | Gly | Arg | Pro<br>300 | Lys | Leu | Ile | Ala |
| Tyr<br>305 | Arg | Glu | Ala | Ala | Lys<br>310 | Asn | Leu | Glu | Ile | Glu<br>315 | Lys | Ile | Gly | Ala | Glu<br>320 |
| His | Val | Lys | Gln | Cys<br>325 | His | Ser | His | Asn | Leu<br>330 | Val | Met | Thr | Met | Pro<br>335 | Leu |
| Lys | Ser | Ile | Ser<br>340 | Asn | Phe | Ser | Tyr | | | | | | | | |

( 2 ) INFORMATION FOR SEQ ID NO: 10:

( i ) SEQUENCE CHARACTERISTICS:
       ( A ) LENGTH: 441 amino acids
       ( B ) TYPE: amino acid
       ( D ) TOPOLOGY: linear ( i i ) MOLECULE TYPE: protein ( i i i ) HYPOTHETICAL: NO (vi) ORIGINAL SOURCE:
    (A) ORGANISM: Lactococcus lactis subsp. lactis
    (C) INDIVIDUAL ISOLATE: ILVA (xi) SEQUENCE DESCRIPTION: SEQ ID NO: 10:

```
Met  Ile  Ser  Ala  Lys  Glu  Val  Glu  Asp  Ala  Tyr  Asp  Leu  Leu  Lys  Ala
1              5                        10                       15

Val  Val  Thr  Lys  Thr  Pro  Leu  Gln  Leu  Asp  Pro  Tyr  Leu  Ser  Asn  Lys
               20                   25                        30

Tyr  Gln  Ala  Asn  Ile  Tyr  Leu  Lys  Glu  Val  Val  Thr  Lys  Thr  Pro  Leu
          35                        40                        45

Gln  Leu  Asp  Pro  Tyr  Leu  Ser  Asn  Lys  Tyr  Gln  Ala  Asn  Ile  Tyr  Leu
     50                        55                   60

Lys  Glu  Glu  Asn  Leu  Gln  Lys  Val  Arg  Ser  Phe  Lys  Leu  Arg  Gly  Ala
65                        70                   75                            80

Tyr  Tyr  Ser  Ile  Ser  Lys  Leu  Ser  Asp  Glu  Gln  Arg  Ser  Lys  Gly  Val
                    85                        90                        95

Val  Cys  Ala  Ser  Ala  Gly  Asn  His  Ala  Gln  Gly  Val  Ala  Phe  Ala  Ala
               100                      105                      110

Asn  Gln  Leu  Asn  Ile  Ser  Ala  Thr  Ile  Phe  Met  Pro  Val  Thr  Thr  Pro
          115                      120                      125

Asn  Gln  Lys  Ile  Ser  Gln  Val  Lys  Phe  Phe  Gly  Glu  Ser  His  Val  Thr
     130                      135                      140

Ile  Arg  Leu  Ile  Gly  Asp  Thr  Phe  Asp  Glu  Ser  Ala  Arg  Ala  Ala  Lys
145                      150                      155                      160

Ala  Phe  Ser  Gln  Asp  Asn  Asp  Lys  Pro  Phe  Ile  Asp  Pro  Phe  Asp  Asp
               165                      170                      175

Glu  Asn  Val  Ile  Ala  Gly  Gln  Gly  Thr  Val  Ala  Leu  Glu  Ile  Phe  Ala
               180                      185                      190

Gln  Ala  Lys  Lys  Gln  Gly  Ile  Ser  Leu  Asp  Lys  Ile  Phe  Val  Gln  Ile
          195                      200                      205

Gly  Gly  Gly  Gly  Leu  Ile  Ala  Gly  Ile  Thr  Ala  Tyr  Ser  Lys  Glu  Arg
          210                      215                      220

Tyr  Pro  Gln  Thr  Glu  Ile  Ile  Gly  Val  Glu  Ala  Lys  Gly  Ala  Thr  Ser
225                      230                      235                      240

Met  Lys  Ala  Ala  Tyr  Ser  Ala  Gly  Gln  Pro  Val  Thr  Leu  Glu  His  Ile
               245                      250                      255

Asp  Lys  Phe  Ala  Asp  Gly  Ile  Ala  Val  Ala  Thr  Val  Gly  Gln  Lys  Thr
               260                      265                      270

Tyr  Gln  Leu  Ile  Asn  Asp  Lys  Val  Lys  Gln  Leu  Leu  Ala  Val  Asp  Glu
          275                      280                      285

Gly  Leu  Ile  Ser  Gln  Thr  Ile  Leu  Glu  Leu  Tyr  Ser  Lys  Leu  Gly  Ile
     290                      295                      300

Val  Ala  Glu  Pro  Ala  Gly  Ala  Thr  Ser  Val  Ala  Ala  Leu  Glu  Leu  Ile
305                      310                      315                      320

Lys  Asp  Glu  Ile  Lys  Gly  Lys  Asn  Ile  Val  Cys  Ile  Ile  Ser  Gly  Gly
               325                      330                      335

Asn  Asn  Asp  Ile  Ser  Arg  Met  Gln  Glu  Ile  Glu  Glu  Arg  Ala  Leu  Val
               340                      345                      350

Tyr  Glu  Gly  Leu  Lys  His  Tyr  Phe  Val  Ile  Asn  Phe  Pro  Gln  Arg  Pro
          355                      360                      365

Gly  Ser  Leu  Arg  Thr  Phe  Val  Ser  Asp  Ile  Leu  Gly  Pro  Asn  Asp  Asp
     370                      375                      380

Ile  Thr  Arg  Phe  Glu  Tyr  Ile  Lys  Arg  Ala  Asp  Lys  Gly  Lys  Gly  Pro
385                      390                      395                      400
```

```
        Cys  Leu  Val  Gly  Ile  Leu  Leu  Ser  Asp  Ala  Ser  Asp  Tyr  Asp  Ser  Leu
                            405                      410                      415

Ile  Asn  Arg  Ile  Glu  Arg  Phe  Asp  Asn  Arg  Tyr  Val  Asn  Leu  Arg  Gly
                            420                      425                      430

Asn  Asp  Ser  Leu  Tyr  Glu  Leu  Leu  Val
                       435                 440
```

( 2 ) INFORMATION FOR SEQ ID NO: 11:

( i ) SEQUENCE CHARACTERISTICS:
        ( A ) LENGTH: 12720 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Lactococcus lactis subsp. lactis ( x i ) SEQUENCE DESCRIPTION: SEQ ID NO: 11:

```
TAAAACTCGA  TAATCTTGAG  TCATAATTTC  TCCTTAATCT  TATTAGTACA  TTAGAATCCA    60
TTATAATTTA  ATCATTTTAT  GTCTACCTAA  AGCAACAAAA  TTGCTTGTAT  ATTTTCTAAC   120
AAGCTTAATT  ATGTGGATTT  AATTGAATAT  TAAAGGGAGA  AGTTGTAATC  TATTTGTTGT   180
TAAATTCTTG  TTAATACAAA  TAAATTTATT  AAATATTATT  ATTTTATTGA  CAATTTAAAA   240
TATTAAGAGT  ATTATAATGT  AAATTAACAA  AAAAAAGAGG  AACTTGAAAT  GACATACACA   300
CAATTTTCAT  TGTTGTTGAT  CAAGGTGGAC  CTACATTAGC  TTTTTTGGCT  AAAATATGTG   360
GGTCCTGTTT  GGCGATAGTC  ATTTCGAGGA  CCGAGAGACG  TCCTCACGGG  CGTCTTTTTT   420
GTTTCTTAAT  AAAAAATAGA  GGTAATATTA  TGCGAAAAAT  TGAATTCTTT  GACACAAGTT   480
TGAGAGATGG  CGAACAGACA  CCGGGCGTTA  GTTTCTCCAT  TTCAGAAAAA  GTAACGATTG   540
CTAAACAACT  GGAAAAATGG  AGGATTTCTG  TCATAGAGGC  TGGTTTTTCT  GCGGCAAGTC   600
CAGATAGTTT  TGAAGCAGTA  AAGCAAATTG  CTGATTCTTT  GAATGATACG  GCTGTCACTG   660
CATTAGCTCG  CTGTGTTATT  TCAGATATCG  ATAAAGCGGT  TGAAGCGGTA  AAGGGGGCTA   720
AATATCCGCA  AATTCATGTT  TTCATTGCAA  CTTCACCTAT  TCACATGAAA  TATAAACTTA   780
AAATCAGTCC  CGAAGAAGTT  TTGAAAAATA  TTGATAAGTG  TGTGAGATAC  GCACGTGAAC   840
GGGTCGAGGT  TGTTGAGTTT  CTCCAGAGG  ATGCAACAAG  AACGGAGTTG  AATTTTCTTT   900
TAGAGGCTGT  TCAAACGGCT  GTCGATGCTG  GAGCAACTTA  TATTAATATT  CCTGACACTG   960
TCGGTTATAC  GACACCAGAA  GAATATGGAA  AAATTTTTAA  ATTTTTGATT  GATAATACTA  1020
AGTCTGACCG  AGAAATTATT  TTTAGTCCAC  ATTGTCATGA  TGATTTAGGA  ATGGCTGTAG  1080
CTAATTCATT  AGCTGCAATT  AAAGCTGGGG  CTGGGAGAGT  TGAAGGAACT  GTCAATGGTA  1140
TTGGAGAGCG  AGCTGGGAAT  GCTGCTCTTG  AAGAAATTGC  TGTGGCACTA  CATATTCGTA  1200
AAGATTTTTA  TCAGGCACAA  AGTCCTTTAA  AACTTTCAGA  AACTGCTGCA  ACGGCAGAAC  1260
TAATTTCACA  ATTTTCAGGA  ATTGCTATTC  CAAAAAATAA  AGCAATTGTT  GGTGCTAATG  1320
CTTTTGCACA  CGAATCAGGA  ATTCATCAAG  ATGGTGTCCT  TAAAAATGCT  GAAACTTATG  1380
AAATTATTAC  ACCAGAACTT  GTCGGAATAA  AGCATAATTC  GTTGCCTTTA  GGTAAACTTT  1440
CTGGTCGTCA  TGCTTTTAGT  GAAAAATTGA  CGGAACTTAA  TATTGCTTAT  GACGATGAAA  1500
```

```
GTCTTGCAAT TTTATTTGAA AAATTTAAAA AATTAGCTGA CAAGAAAAAA GAAATTACTG    1560
ACGCAGATAT TCATGCCTTG TTTACAGGAG AAACGGTAAA AATCTAGCT  GGATTTATAC    1620
TTGATAATGT TCAAATTGAT GGGCACAAGG CATTGGTGCA ACTAAAAAAT CAAGAAGAGG    1680
AAATTTATGT TAGCCAAGGA GAGGGGTCAG GTTCAGTGGA TGCAATTTTT AAAGCTATTG    1740
ATAAAGTCTT TAATCATCAA CTAAAATTAA TTTCCTATTC AGTTGATGCT GTAACTGATG    1800
GAATTGATGC ACAAGCAACG ACTTTGGTTT CTGTTGAAAA TCTATCTACA GGCACTATAT    1860
TTAATGCTAA AGGTGTTGAT TATGATGTAT TGAAAGGAAG CGCCATTGCT TACATGAACG    1920
CTAATGTTTT AGTTCAAAAA GAAAATTTAC AAGGAAAGGT TGAACAAATT TCAGCTCATG    1980
ATGGAATTTA AGGTGAAAAA TATTGTCTAA AAAAATTGTG ACACTTGCGG GAGATGGAAT    2040
TGGGCCAGAA ATTATGTCAG CTGGTTTAAG TGTTTTAAAA GCTGTCAGTA AAAAAATTGA    2100
TTTGAGTAT  GAATTAGAAG CTAAAGATTT TGGAGGAATT GCAATTGATA AGCATGGTCA    2160
TCCTTTACCA GAAGAAACTT TGCAAGCAGT TAAAAATGCT GACGCAATCT TGCTCGCTGC    2220
AATTGGTCAT CCTAAATACA ACAATGCAAA AGTTAGACCA GAACAAGGGC TACTTGCTTT    2280
ACGAAAAGAA TTAGGACTGT ATGCTAATGT TCGTCCATTA AAAATTTATC CGGCTCTAAA    2340
AAAACTTTCT CCCATACGAA ATGTTGAAAA TGTTGATTTC CTAGTGATTC GCGAACTTAC    2400
AGGGGGAATC TATTTCGGTC AGCATGAATT GGCAGATGAT AAAGCACGAG ATGTCAATGA    2460
TTATTCTGCT GATGAAATAA GGAGAATTCT TCATTTTGCT TTCAAAAGTG CTCAAAGTCG    2520
GCCCAGAAAA TTACTGACTT CGGTTGATAA ACAAAATGTT CTTGCAACTT CTAAATTATG    2580
GCGAAAAATG GCTGATGAAA TTGCTGACGA ATATCCTGAT GTACGATTAG AGCACCAATT    2640
GGTCGATTCT TGTGCGATGT TACTGATTAC TAATCCGCAA CAATTTGATG TGATAGTCAC    2700
TGAAAATCTA TTTGGTGATA TTCTCTCTGA TGAAGCAAGT AGTTTGGCCG GTAGCTTAGG    2760
AGTGATGCCT TCGAGTTCGC ATGGATTTAA CGGTTTAGCA CTCTATGAGC CAATTCATGG    2820
TTCGGCACCA GATATTGCAG GAAAAGGAAT TGCGAACCCT GTTTCGATGA TTCTATCAAT    2880
TGCCATGATG CTAAGAGAAT CTTTTGGGCA AGAAGATGGG GCTGCGATGA TTGAAAAAGC    2940
CGTAACCCAA ACTTTTACTG ACGGAATTTT GACTAAAGAT TTAGGTGGGA CTGCAACAAC    3000
TAAAGAAATG ACAGAAGCAA TCCTGAAAAA TTGTCAGTAA AATGCGATTG AATAGTGAGC    3060
ATTTTAGTTG TAGATAAAAG AACCGTCAGC ATAGCTGACA ATTCTGTCAG TAAATGCGAT    3120
TGAATAGTGA GCATTTAGT  TGTAGATAAA AGAACCGTCA GCATAGCTGA CAATTCTGTC    3180
AGTAATTGCG ATTGAATAGT GAGCATTTTA GTTGTAGATA AAGAACCGT  CAGCATAGCT    3240
GACAATTCTG TCAGTAATTG CGATTGAATA GTGAGCATTT AGTTGTAGA  TAAAAGAACT    3300
ATCAGCGTAA CTGACAATTC TGTCAGTAAA TATTACTGAC AAAAAGTACA AAATTACTGA    3360
CAGAATTTGT CAGAATAAAT TTTTAAAAAA GGAAATAAAA AATGTCAGG  TAAAACAATA    3420
TTTGATAAAC TTTGGGATCA GCATGTGATT GCTGGAAATG AGGGAGAACC TCAACTGCTT    3480
TATATTGACC TTCATGTTAT TCATGAGGTT ACGAGTCCGC AAGCATTTCA GGGCTTACGT    3540
GAAGCAGGAC GTCGTGTTCG GAGAAAAGAT TTGACATACG GAACTCTTGA CCACAATGTT    3600
CCAACACAAA ATATTTTTAA TATTCAAGAT TTGATTTCTA AAAACAAAT  TGATACTTTT    3660
ACTAAAAATG TCAAAGAATT TGATGTTCCA GCGGAGACTC ATGGTGGAAA AGGACAAGGA    3720
ATTGTTCACA TGGTAGCACC TGAATCTGGC AGAACTCAAC CGGGAAAAAC AATTGTTTGT    3780
GGCGATAGTC ATACCGCAAC AAATGGAGCA TTTGGTGCAA TTGCTTTTGG AATTGGTACA    3840
AGTGAAGTTG AACATGTTCT TGCAACTCAA ACCATTTGGC AAGTTAAACC CAAGCGTATG    3900
```

| | | | | | |
|---|---|---|---|---|---|
| AAAATTGAAT | TTCAAGGTCA | TCCACAAAAA | GGAATTTATA | GCAAAGACTT | TATCCTCGCA | 3960
| TTAATTGCTA | AATATGGTGT | GGATGCAGGT | GTAGGTTATG | CGGTTGAATA | TAGTGGGGAT | 4020
| GCTATCAGTG | ATTTAAGCAT | GGAAGAACGG | ATGACAATCT | GTAACATGTC | AATTGAATTT | 4080
| GGGGCAAAAA | TTGGCCTGAT | GAATCCTGAT | GAAAAACTT | ATGACTATGT | CAAGGGCGT | 4140
| GAACATGCAC | CTAAAAACTT | TGATGAAGCT | GTCAGTAAAT | GGGAAAAACT | TGTCAGTGAT | 4200
| TCTGATGCAC | AATACGATAA | GATTTTAAGT | CTTGATGTCA | GCCAGTTGAA | ACCAATGGTG | 4260
| ACATGGGGAA | CAAATCCCGG | AATGGGCCTA | GAATTTGGCG | AAAAGTTTCC | GGAAATTAAC | 4320
| AATGATTTGA | ATTATGAACG | TGCTTATCAG | TACATGGATT | TAAAGCCAGG | CCAAACCGCT | 4380
| TCTGACATAG | ATTTAGGCTA | TATTTTCATT | GGTTCTTGTA | CGAATGCTAG | ACTTGGTGAT | 4440
| TTAGAAGAAG | CTGCAAAAAT | TATTGGAGAC | AGACATATTG | CTGATGGACT | GACAGGAATT | 4500
| GTCGTCCCTG | GAAGCAGACC | TGTGAAAGAA | GCGGCTGAAG | CACAAGGGCT | TGATAAAATT | 4560
| TTTAAAGAAG | CTGGTTTTGA | ATGGCGGGAA | CCGGGTTGCT | CAGCCTGTCT | TGGAATGAAT | 4620
| CCTGACCAAA | TTCCAGAATA | CGTTCATTGT | GCTTCAACCT | CTAATCGAAA | TTTTGAAGGT | 4680
| CGTCAAGGAC | ATAATGCAAG | AACGCACCTG | TGCTCTCCAG | CTATGGCTGC | TGCCGCCGCA | 4740
| ATCGCTGGTA | AATTTGTAGA | TGTTAGAATG | CTCGTAACAG | ATTAGTCTGT | AGAAAGAAAA | 4800
| AAAGATGGAA | AAATTCACGA | TTTACAAAGG | GACAAGTGTT | CCAGTCATGA | ACGATAATAT | 4860
| TGACACAGAC | CAAATTATTC | CTAAACAATT | TTTGAAAGCA | ATCGATAAAA | AGGGCTTTGG | 4920
| GAAAAATTTA | TTTTATGAAT | GGCGTTATCT | TAAAGATTAC | GATGAGAATC | CTGATTTTAT | 4980
| TTTGAATGCT | CCAAAATACA | AAAAAGCTTC | TCTGTTAATT | TCAGGAGATA | ATTTTGGTTC | 5040
| GGGTTCTTCA | AGAGAACATG | CGGCATGGGC | CTTATCAGAT | TACGGCTTTC | GGGCAATTAT | 5100
| TGCTGGCTCT | TACTCAGATA | TTTTTTATAA | TAATGCTTTA | AAAAATGGCT | TGTTACCAAT | 5160
| TAAACAACCA | AGAGAAGTTC | TAAATCAACT | GACAAAACTG | TCAAGTCAAG | AAGAAATTAC | 5220
| AATTGATTTA | CCCCATCAGC | TAATCATCAC | AAGCCTTGGT | GACTTTCATT | TTGAGATTGA | 5280
| CCCCATTTGG | AAAGACAAAT | TAATTAATGG | CTTAGATGAT | ATTGGAATAA | CTTGCAATA | 5340
| TGAAGAAGCA | ATCTCAGCTT | ACGAACAAAA | AAATCAATAA | GAGCGAGCCT | AAAATGACAA | 5400
| TTATTAATTT | AAAGAATGTA | AATCTTACTC | GAAATAAAAA | AGAAATTCTT | AAAGATATTA | 5460
| CTTGGAAAGT | AAATCCCGGC | GAAAATTGGG | TTATTCTGGG | CCTCAACGGC | TCTGGAAAAT | 5520
| CAAGTCTTTT | GAAATTGATT | TTAGCAGAAG | AATGGAAAAC | TTCTGGTGAA | ATCACTGTTT | 5580
| TAAATACTCA | ATTTAGAAAT | GGAGAAATTC | CTAAGTTGAG | AAAAAGAATC | AGCGTAGTTG | 5640
| GCTCATTTAT | TGCTGAAAGA | TTTCAACCAA | ATATTAAGGC | TGAAAACCTT | GTTTATACTG | 5700
| GGAAATTTAA | TTCGAGCATG | CTCTATAAAC | CCTACACAGA | TCAGGAACTT | GATGAGGCCC | 5760
| GTCAGCTTTT | AAGACAAATG | GGCGCAAAAT | CACTTATTGG | CCGAAATTAT | GCCAGCCTTT | 5820
| CTCAAGGGGA | AAAGCAAGTT | CTTCTTATTG | CTAGGAGCTT | AATTTAAAG | CCTGAGCTTT | 5880
| TAATTTTGGA | CGAAGCAACG | AACGGTTTAG | ATTTATTTGC | TAAAGAAAAA | TTATTAAAGC | 5940
| AACTGCAGCA | GATTAATCAA | TTAAAAACCG | CACCAACACT | AATTTATATT | TCTCATCATC | 6000
| CCGATGAAAT | CACTGATATT | TTTACTCACC | TTTTACTTTT | AAGAGAAGGA | AAAGTGATTC | 6060
| AATCAGGGAA | AAAAGAAAAC | TTATTAAATG | AAAAGATACT | TACTGATTTT | TATCAAGAAA | 6120
| AAGTAGAAGT | TCACCGTTTT | GAGCAGAAAT | ATTTTGTAAT | TCCTGCTAAC | TGAGAAAGGA | 6180
| AAGCAAAAGT | ATTTTATATA | CTATATAGAA | TATTCTGACA | GATTATTGTA | TTTTCATTTT | 6240
| TTTAGTGATA | AAATAGCTCT | ATGTAAATTT | ACGGGGAGGT | CAAAAAGATA | ACATATGGAA | 6300

| | | | | | | |
|---|---|---|---|---|---|---|
| TTCAAATATA | ACGGAAAAGT | TGAATCAGTG | GAACTCAATA | AATATTCTAA | GACATTGACT | 6360 |
| CCAAGATCAA | CACAACCAGC | GACTCAAGCG | ATGTACTACG | GCATTGGTTT | TAAAGATGAG | 6420 |
| GATTTCAAAA | AAGCTCAGGT | CGGAATCGTC | AGCATGGATT | GGGACGGAAA | TCCATGTAAT | 6480 |
| ATGCACTTGG | GAACACTTGG | GAGTAAAATC | AAAAGTTCTG | TCAACCAAAC | TGACGGATTG | 6540 |
| ATTGGACTTC | AATTTCATAC | TATTGGAGTT | TCTGATGGAA | TTGCTAACGG | AAAGCTTGGC | 6600 |
| ATGAGATATT | CTTTGGTCAG | TCGTGAAGTT | ATTGCTGACA | GCATCGAAAC | CAACGCTGGC | 6660 |
| GCAGAATATT | ATGATGCCAT | CGTTGCCATT | CCCGGTTGTG | ATAAAAATAT | GCCCGGGTCA | 6720 |
| ATTATCGGAA | TGGCTCGCTT | AAATCGTCCG | TCAATTATGG | TCTATGGTGG | AACGATTGAA | 6780 |
| CATGGCGAAT | ATAAGGTGA | AAAATTAAAT | ATTGTTTCGG | CCTTTGAAGC | TCTGGGCAA | 6840 |
| AAAATCACTG | GAAATATTTC | TGATGAAGAT | TATCATGGCG | TTATTTGCAA | TGCCATTCCA | 6900 |
| GGACAAGGTG | CTTGCGGAGG | AATGTACACT | GCCAATACCC | TGGCTGCTGC | TATTGAAACT | 6960 |
| TTGGGAATGA | GTTTACCTTA | TTCCTCTTCC | AATCCAGCAG | TCAGTCAAGA | AAAACAAGAA | 7020 |
| GAGTGTGATG | ACATTGGTTT | AGCCATCAAA | AATTATTAG | AAAAGATAT | TAAACCAAGT | 7080 |
| GATATCATGA | CCAAGAAGC | TTTTGAAAAT | GCCATAACAA | TTGTCATGGT | CCTTGGAGGC | 7140 |
| TCAACCAATG | CTGTGCTTCA | TATCATTGCA | ATGGCAAATG | CCATTGGTGT | AGAAATTACG | 7200 |
| CAAGATGATT | TCCAACGTAT | TTCAGATATT | ATCCCTGTTC | TTGGCGATTT | CAAACCGAGC | 7260 |
| GGAAAATATA | TGATGGAAGA | TCTGCACAAA | ATTGGTGGCC | TTCCTGCTGT | TTTGAAATAC | 7320 |
| CTACTTAAAG | AAGGAAAACT | TCACGGTGAT | TGTTTGACCG | TCACAGGTAA | AACTTTGGCT | 7380 |
| GAAAATGTTG | AAACAGCATT | AGATTTGGAC | TTTGACAGTC | AAGATATTAT | GCGACCACTA | 7440 |
| AAAAATCCAA | TTAAAGCTAC | TGGACATTTA | CAAATTTTGT | ACGGTAATCT | TGCCCAAGGG | 7500 |
| GGTTCTGTTG | CAAAAATTTC | TGGTAAAGAA | GGCGAATTTT | TCAAAGGAAC | AGCTCGTGTT | 7560 |
| TTTGACGGAG | AACAACACTT | TATCGATGGC | ATTGAGTCTG | GCCGATTGCA | TGCCGGTGAT | 7620 |
| GTTGCGGTCA | TTAGAAATAT | TGGCCCAGTC | GGAGGTCCGG | GAATGCCAGA | GATGTTAAAA | 7680 |
| CCAACCTCAG | CATTAATTGG | AGCAGGACTT | GGAAAATCTT | GTGCCCTAAT | TACTGACGGA | 7740 |
| AGATTTTCTG | GTGGCACACA | CGGCTTTGTT | GTGGGTCATA | TCGTCCCTGA | AGCAGTTGAA | 7800 |
| GGTGGGTTGA | TTGGTTTAGT | TGAAGATGAT | GATATTATCG | AAATTGATGC | GGTGAATAAT | 7860 |
| AGTATTAGTT | TAAAAGTTTC | TAATGAAGAA | ATTGCTAAAC | GACGTGCCAA | TTATCAAAAA | 7920 |
| CCAACCCCTA | AAGCAACGCG | TGGTGTTCTT | GCAAAATTTG | CCAAACTTAC | GCGCCCCGCT | 7980 |
| AGTGAAGGTT | GCGTTACAGA | TTTATAGAAA | GGTTTGAATG | AAAAAAATAA | AGTTAGAAAA | 8040 |
| ACCTACTTCC | GGTTCCCAAC | TTGTTCTCCA | AACCTTAAAA | GAACTTGGAG | TAGAAATTAT | 8100 |
| TTTTGGTTAT | CCTGGTGGGG | CCATGCTCCC | CTTGTATGAT | GCGATTCATA | ATTTTGAAGG | 8160 |
| AATTCAACAT | ATTTTAGCCC | GTCATGAGCA | AGGAGCAACG | CATGAAGCCG | AAGGTTACGC | 8220 |
| TAAATCGTCT | GGTAAAGTTG | GTGTCGTCGT | TGTTACGTCA | GGACCAGGAG | CGACTAATGC | 8280 |
| AGTAACCGGA | ATTGCTGACG | CTTATCTTGA | TTCAGTCCCA | TTGTTAGTTT | TCACAGGTCA | 8340 |
| AGTTGGCCGT | CAGTCAATTG | GTAAAGATGC | TTTTCAAGAA | GCAGATACTG | TTGGAATTAC | 8400 |
| AGCCCCAATT | ACAAAATATA | ATTATCAAAT | TAGGGAAACC | GCAGATATTC | CAAGAATTGT | 8460 |
| TACAGAAGCC | TATTATTTGG | CAAGGACAGG | ACGTCCTGGA | CCAGTAGAAA | TTGATTTACC | 8520 |
| AAAAGATGTT | CCACCCTTG | AAGTCACTGA | AATTAATGAC | CCAAGCTTGA | ATCTTCCTCA | 8580 |
| TTATCACGAA | AGTGAAAAAG | CGACTGATGA | ACAATTGCAA | GAATTACTGA | CAGAACTTTC | 8640 |
| TGTCAGTAAA | AAACCAGTCA | TTATTGCTGG | CGGAGGAATT | AATTATTCTG | GCTCAGTTGA | 8700 |

```
TATTTTCAGA GCATTTGTCG AAAAATATCA AATTCCAGTT GTTTCTACAT TGCTTGGCTT    8760
AGGAACATTA CCAATCAGCC ACGAATTGCA ACTAGGAATG GCAGGAATGC ACGGTTCATA    8820
CGCTGCAAAT ATGGCTTTAG TTGAAGCTGA CTATATTATT AATTTGGGAT CACGTTTTGA    8880
CGATAGAGTT GTATCCAATC CTGCAAAATT TGCTAAAAAT GCTGTCGTTG CTCATATTGA    8940
TATTGACGCT GCTGAACTTG GCAAAATTGT AAAAACCGAT ATTCCAATCC TTTCTGATTT    9000
GAAAGCGGCT TTAAGCAGAC TTTTGCAATT AAATAAGGTC AGGACTGACT TTAATGATTG    9060
GATTAAAACT GTCATTGAAA ATAAAGAGAA AGCACCATTT ACTTATGAGC CCCAAAACCA    9120
TGATATCCGT CCACAGGAAA CAATTAAATT AATTGGAGAA TACACTCAAG GAGATGCAAT    9180
CATTGTAACT GACGTTGGGC AACATCAAAT GTGGGTGGCG CAATATTATC CTTATAAAAA    9240
TGCAAGGCAA CTTATTACTT CTGGGGGAAT GGGAACGATG GGCTTTGGCA TTCCTGCAGC    9300
AATCGGTGCA AAGCTGGCAC AGCCAAATAA AAATGTCATT GTTTTGTTG GCGATGGTGG     9360
CTTTCAAATG ACTAATCAAG AATTAGCATT ACTTAATGGC TACGGTATTG CAATCAAAGT    9420
TGTGCTGATT AATAATCATT CATTGGGAAT GGTACGTCAA TGGCAAGAAT CATTCTATGA    9480
AGAGCGACGT TCACAATCGG TTTTTGATGT TGAACCCAAT TTCAATTGT TAGCCGAAGC     9540
TTATGGCATC AAACATGTTA AGTTAGATAA TCCAAAAACT TTGGCTGATG ATTTAAAAAT    9600
TATTACAGAA GATGAGCCAA TGCTTATTGA AGTTCTAATT TCAAAATCTG AGCATGTTTT    9660
ACCAATGATA CCAGCTGGAT TACACAATGA CGAAATGATT GGACTTCATT TTACTGATAA    9720
GAATGAGGAG ATAGATAATG CGTAGAATGA TTATCGCAAA ACTTCATAAC GTGACAGGAA    9780
TTATGAATCG ATTTACCGCC GTTCTCAATC GAAGGCAAGT GAACATTCTC TCAATTACCG    9840
CTGGAGTTAC AGAAAGTCAA GACTTAACTC ATACCACTTT TGTTATTGAA GTTGATCATC    9900
TTGATGAAGT AGAACAAATC ATTAAACAAT TAAATCGCTT AATAGATGTA ATTGAAGTAG    9960
CTGATATTAC TGATTTTCCT CATGTAGAAC GTGAAGTCGT CTTGATTAAA GTATCAGCTC    10020
CACCGACCAT TAGGGCAGAA ATTTTTACAA TGATTGAACC TTTTAGAGTA AATGTAGTTG    10080
ATGTCAATCT GGAAAATGTC ACCATTCAAT TAACGGGTGA TTCAGCAAAA ATCGAAGCAC    10140
TTATTGAGGT TGTTAGTCCT TATGGCATTC TAAATATGGC TCGGACAGGT AGTGCAGGTT    10200
TTGAGCGTGG CTAAATTTAA ATAAGTTAAC AAATAAATAG AAAAATAGAG GAAACAAAAA    10260
TGGCAGTTAC AATGTATTAT GAAGATGATG TAGAAGTATC AGCACTTGCT GGAAAGCAAA    10320
TTGCAGTAAT CGGTTATGGT TCACAAGGAC ATGCTCACGC ACAGAATTTG CGTGATTCTG    10380
GTCACAACGT TATCATTGGT GTGCGCCACG GAAAATCTTT TGATAAAGCA AAAGAAGATG    10440
GCTTTGAAAC ATTTGAAGTA GGAGAAGCAG TAGCTAAAGC TGATGTTATT ATGGTTTTGG    10500
CACCAGATGA ACTTCAACAA TCCATTTATG AAGAGGACAT CAAACCAAAC TTGAAAGCAG    10560
GTTCAGCACT TGGTTTTGCT CACGGATTTA ATATCCATTT TGGCTATATT AAAGTACCAG    10620
AAGACGTTGA CGTCTTTATG GTTGCGCCTA AGGCTCCAGG TCACCTTGTC CGTCGGACTT    10680
ATACTGAAGG TTTTGGTACA CCAGCTTTGT TTGTTTCACA CCAAAATGCA AGTGGTCATG    10740
CGCGTGAAAT CGCAATGGAT TGGGCCAAAG GAATTGGTTG TGCTCGAGTG GAATTATTG     10800
AAACAACTTT TAAAGAAGAA ACAGAAGAAG ATTTGTTTGG AGAACAAGCT GTTCTATGTG    10860
GAGGTTTGAC AGCACTTGTT GAAGCCGGTT TTGAAACACT GACAGAAGCT GGATACGCTG    10920
GCGAATTGGC TTACTTTGAA GTTTTGCACG AAATGAAATT GATTGTTGAC CTCATGTATG    10980
AAGGTGGTTT TACTAAAATG CGTCAATCCA TCTCAAATAC TGCTGAGTTT GGCGATTATG    11040
TGACTGGTCC ACGGATTATT ACTGACGAAG TTAAAAAGAA TATGAAGCTT GTTTTGGCTG    11100
```

| | | | | | |
|---|---|---|---|---|---|
| ATATTCAATC | TGGAAAATTT | GCTCAAGATT | TCGTTGATGA | CTTCAAAGCG | GGGCGTCCAA | 11160 |
| AATTAATAGC | CTATCGCGAA | GCTGCAAAAA | ATCTTGAAAT | TGAAAAAATT | GGGGCAGAGC | 11220 |
| ACGTCAAGCA | ATGCCATTCA | CACAATCTGG | TGATGACGAT | GCCTTTAAAA | TCTATCAGTA | 11280 |
| ATTTCTCTTA | TTGATTGAAC | AAAAACATAA | AAGCATTTTA | TGGAGGAATG | ACATAAATGA | 11340 |
| TAAGTGCCAA | AGAGGTTGAA | GATGCCTATG | ATTTGTTAAA | AGCAGTTGTC | ACTAAAACAC | 11400 |
| CTTTACAATT | AGACCCTTAC | CTTTCCAATA | AATATCAAGC | AAATATTTAC | TTAAAAGAAG | 11460 |
| TTGTCACTAA | AACACCTTTA | CAATTAGACC | CTTACCTTTC | CAATAAATAT | CAAGCAAATA | 11520 |
| TTTACTTAAA | AGAAGAAAAC | TTACAGAAAG | TTCGTTCTTT | TAAATTACGA | GGAGCTTATT | 11580 |
| ATTCTATCAG | TAAATTATCT | GATGAGCAAC | GCTCTAAAGG | AGTGGTTTGT | GCCTCAGCAG | 11640 |
| GAAATCATGC | ACAAGGGGTT | GCTTTTGCTG | CAAATCAATT | AAATATTTCT | GCGACAATTT | 11700 |
| TTATGCCCGT | TACCACACCT | AACCAAAAAA | TTTCACAAGT | TAAATTTTTT | GGCGAAAGTC | 11760 |
| ACGTAACAAT | TCGTTTAATT | GGTGATACTT | TTGATGAATC | AGCCAGAGCA | GCAAAAGCTT | 11820 |
| TTTCTCAAGA | TAATGACAAA | CCATTTATAG | ACCCTTTTGA | TGATGAAAAT | GTAATTGCTG | 11880 |
| GTCAAGGGAC | AGTGGCTTTA | GAAATTTTTG | CGCAAGCTAA | AAAACAAGGA | ATAAGTTTAG | 11940 |
| ATAAGATTTT | TGTACAGATT | GGTGGAGGTG | GTTAATTGC | AGGAATTACT | GCCTACAGTA | 12000 |
| AGGAGCGCTA | TCCCCAAACT | GAAATTATCG | GAGTTGAAGC | AAAAGGGGCA | ACAAGTATGA | 12060 |
| AAGCTGCCTA | CTCTGCTGGT | CAGCCCGTCA | CCTTGGAACA | CATTGATAAA | TTTGCTGACG | 12120 |
| GAATTGCGGT | TGCGACTGTC | GGTCAGAAAA | CTTACCAACT | TATTAATGAC | AAAGTGAAAC | 12180 |
| AATTGCTTGC | GGTTGATGAA | GGTTTAATTT | CTCAAACCAT | ACTCGAATTG | TATTCAAAAT | 12240 |
| TAGGAATTGT | CGCCGAGCCA | GCAGGTGCAA | CATCTGTTGC | CGCACTTGAA | CTTATTAAAG | 12300 |
| ATGAAATCAA | GGGTAAAAAT | ATCGTCTGTA | TCATCAGCGG | CGGAAATAAT | GATATTAGTC | 12360 |
| GAATGCAAGA | AATTGAAGAA | AGAGCTTTGG | TTTATGAAGG | TCTAAAACAT | TATTTTGTCA | 12420 |
| TTAACTTTCC | TCAAAGACCA | GGATCCTTAC | GAACTTTGT | CAGTGATATT | TTAGGGCCAA | 12480 |
| ATGATGATAT | CACCCGATTT | GAGTACATCA | AAAGGGCTGA | TAAAGGTAAA | GGACCTTGTC | 12540 |
| TTGTTGGGAT | TTTACTTTCA | GATGCTAGTG | ATTATGATTC | ATTGATTAAT | CGGATTGAAA | 12600 |
| GATTTGATAA | TCGTTATGTT | AACTTACGTG | GAAATGATAG | TTTATACGAA | CTTTTGGTCT | 12660 |
| AACTAACCAA | TTGGTTTGAG | CCATTTTCTA | GTTCAATTC | TCTTTAAATC | ACTAGAAATT | 12720 |

( 2 ) INFORMATION FOR SEQ ID NO: 12:

( i ) SEQUENCE CHARACTERISTICS:
            ( A ) LENGTH: 1728 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( v i ) ORIGINAL SOURCE:
            ( A ) ORGANISM: Lactococcus lactis subsp. lactis
            ( C ) INDIVIDUAL ISOLATE: ilvB ( x i ) SEQUENCE DESCRIPTION: SEQ ID NO: 12:

| | | | | | |
|---|---|---|---|---|---|
| ATGAAAAAAA | TAAAGTTAGA | AAAACCTACT | TCCGGTTCCC | AACTTGTTCT | CCAAACCTTA | 60 |
| AAAGAACTTG | GAGTAGAAAT | TATTTTTGGT | TATCCTGGTG | GGGCCATGCT | CCCCTTGTAT | 120 |
| GATGCGATTC | ATAATTTTGA | AGGAATTCAA | CATATTTTAG | CCCGTCATGA | GCAAGGAGCA | 180 |
| ACGCATGAAG | CCGAAGGTTA | CGCTAAATCG | TCTGGTAAAG | TTGGTGTCGT | CGTTGTTACG | 240 |

| | | | | | |
|---|---|---|---|---|---|
| TCAGGACCAG | GAGCGACTAA | TGCAGTAACC | GGAATTGCTG | ACGCTTATCT | TGATTCAGTC | 300 |
| CCATTGTTAG | TTTTCACAGG | TCAAGTTGGC | CGTCAGTCAA | TTGGTAAAGA | TGCTTTTCAA | 360 |
| GAAGCAGATA | CTGTTGGAAT | TACAGCCCCA | ATTACAAAAT | ATAATTATCA | AATTAGGGAA | 420 |
| ACCGCAGATA | TTCCAAGAAT | TGTTACAGAA | GCCTATTATT | TGGCAAGGAC | AGGACGTCCT | 480 |
| GGACCAGTAG | AAATTGATTT | ACCAAAAGAT | GTTTCCACCC | TTGAAGTCAC | TGAAATTAAT | 540 |
| GACCCAAGCT | TGAATCTTCC | TCATTATCAC | GAAAGTGAAA | AAGCGACTGA | TGAACAATTG | 600 |
| CAAGAATTAC | TGACAGAACT | TTCTGTCAGT | AAAAAACCAG | TCATTATTGC | TGGCGGAGGA | 660 |
| ATTAATTATT | CTGGCTCAGT | TGATATTTTC | AGAGCATTTG | TCGAAAAATA | TCAAATTCCA | 720 |
| GTTGTTTCTA | CATTGCTTGG | CTTAGGAACA | TTACCAATCA | GCCACGAATT | GCAACTAGGA | 780 |
| ATGGCAGGAA | TGCACGGTTC | ATACGCTGCA | AATATGGCTT | TAGTTGAAGC | TGACTATATT | 840 |
| ATTAATTTGG | GATCACGTTT | TGACGATAGA | GTTGTATCCA | ATCCTGCAAA | ATTTGCTAAA | 900 |
| AATGCTGTCG | TTGCTCATAT | TGATATTGAC | GCTGCTGAAC | TTGGCAAAAT | TGTAAAAACC | 960 |
| GATATTCCAA | TCCTTTCTGA | TTTGAAAGCG | GCTTAAGCA | GACTTTTGCA | ATTAAATAAG | 1020 |
| GTCAGGACTG | ACTTTAATGA | TTGGATTAAA | ACTGTCATTG | AAAATAAAGA | GAAAGCACCA | 1080 |
| TTTACTTATG | AGCCCCAAAA | CCATGATATC | CGTCCACAGG | AAACAATTAA | ATTAATTGGA | 1140 |
| GAATACACTC | AAGGAGATGC | AATCATTGTA | ACTGACGTTG | GGCAACATCA | AATGTGGGTG | 1200 |
| GCGCAATATT | ATCCTTATAA | AAATGCAAGG | CAACTTATTA | CTTCTGGGGG | AATGGGAACG | 1260 |
| ATGGGCTTTG | GCATTCCTGC | AGCAATCGGT | GCAAAGCTGG | CACAGCCAAA | TAAAAATGTC | 1320 |
| ATTGTTTTTG | TTGGCGATGG | TGGCTTTCAA | ATGACTAATC | AAGAATTAGC | ATTACTTAAT | 1380 |
| GGCTACGGTA | TTGCAATCAA | AGTTGTGCTG | ATTAATAATC | ATTCATTGGG | AATGGTACGT | 1440 |
| CAATGGCAAG | AATCATTCTA | TGAAGAGCGA | CGTTCACAAT | CGGTTTTTGA | TGTTGAACCC | 1500 |
| AATTTCAAT | TGTTAGCCGA | AGCTTATGGC | ATCAAACATG | TTAAGTTAGA | TAATCCAAAA | 1560 |
| ACTTTGGCTG | ATGATTTAAA | AATTATTACA | GAAGATGAGC | CAATGCTTAT | TGAAGTTCTA | 1620 |
| ATTTCAAAAT | CTGAGCATGT | TTTACCAATG | ATACCAGCTG | GATTACACAA | TGACGAAATG | 1680 |
| ATTGGACTTC | ATTTTACTGA | TAAGAATGAG | GAGATAGATA | ATGCGTAG | | 1728 |

( 2 ) INFORMATION FOR SEQ ID NO: 13:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: ilvN ( x i ) SEQUENCE DESCRIPTION: SEQ ID NO: 13:

| | | | | | |
|---|---|---|---|---|---|
| ATGCGTAGAA | TGATTATCGC | AAAACTTCAT | AACGTGACAG | GAATTATGAA | TCGATTTACC | 60 |
| GCCGTTCTCA | ATCGAAGGCA | AGTGAACATT | CTCTCAATTA | CCGCTGGAGT | TACAGAAAGT | 120 |
| CAAGACTTAA | CTCATACCAC | TTTTGTTATT | GAAGTTGATC | ATCTTGATGA | AGTAGAACAA | 180 |
| ATCATTAAAC | AATTAAATCG | CTTAATAGAT | GTAATTGAAG | TAGCTGATAT | TACTGATTTT | 240 |
| CCTCATGTAG | AACGTGAAGT | CGTCTTGATT | AAAGTATCAG | CTCCACCGAC | CATTAGGGCA | 300 |

-continued

| GAAATTTTTA | CAATGATTGA | ACCTTTTAGA | GTAAATGTAG | TTGATGTCAA | TCTGGAAAAT | 360 |
| GTCACCATTC | AATTAACGGG | TGATTCAGCA | AAAATCGAAG | CACTTATTGA | GGTTGTTAGT | 420 |
| CCTTATGGCA | TTCTAAATAT | GGCTCGGACA | GGTAGTGCAG | GTTTTGAGCG | TGGCTAA | 477 |

( 2 ) INFORMATION FOR SEQ ID NO: 14:

( i ) SEQUENCE CHARACTERISTICS:
        ( A ) LENGTH: 2231 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Lactococcus lactis subsp. lactis
        ( C ) INDIVIDUAL ISOLATE: ilvBN ( x i ) SEQUENCE DESCRIPTION: SEQ ID NO: 14:

| ATTTATAGAA | AGGTTTGAAT | GAAAAAAATA | AAGTTAGAAA | AACCTACTTC | CGGTTCCCAA | 60 |
| CTTGTTCTCC | AAACCTTAAA | AGAACTTGGA | GTAGAAATTA | TTTTGGTTA | TCCTGGTGGG | 120 |
| GCCATGCTCC | CCTTGTATGA | TGCGATTCAT | AATTTGAAG | GAATTCAACA | TATTTTAGCC | 180 |
| CGTCATGAGC | AAGGAGCAAC | GCATGAAGCC | GAAGGTTACG | CTAAATCGTC | TGGTAAAGTT | 240 |
| GGTGTCGTCG | TTGTTACGTC | AGGACCAGGA | GCGACTAATG | CAGTAACCGG | AATTGCTGAC | 300 |
| GCTTATCTTG | ATTCAGTCCC | ATTGTTAGTT | TTCACAGGTC | AAGTTGGCCG | TCAGTCAATT | 360 |
| GGTAAAGATG | CTTTTCAAGA | AGCAGATACT | GTTGGAATTA | CAGCCCCAAT | TACAAAATAT | 420 |
| AATTATCAAA | TTAGGGAAAC | CGCAGATATT | CCAAGAATTG | TTACAGAAGC | CTATTATTTG | 480 |
| GCAAGGACAG | GACGTCCTGG | ACCAGTAGAA | ATTGATTTAC | CAAAGATGT | TTCCACCCTT | 540 |
| GAAGTCACTG | AAATTAATGA | CCCAAGCTTG | AATCTTCCTC | ATTATCACGA | AAGTGAAAAA | 600 |
| GCGACTGATG | AACAATTGCA | AGAATTACTG | ACAGAACTTT | CTGTCAGTAA | AAAACCAGTC | 660 |
| ATTATTGCTG | GCGGAGGAAT | TAATTATTCT | GGCTCAGTTG | ATATTTCAG | AGCATTTGTC | 720 |
| GAAAAATATC | AAATTCCAGT | TGTTTCTACA | TTGCTTGGCT | TAGGAACATT | ACCAATCAGC | 780 |
| CACGAATTGC | AACTAGGAAT | GGCAGGAATG | CACGGTTCAT | ACGCTGCAAA | TATGGCTTTA | 840 |
| GTTGAAGCTG | ACTATATTAT | TAATTTGGGA | TCACGTTTTG | ACGATAGAGT | TGTATCCAAT | 900 |
| CCTGCAAAAT | TTGCTAAAAA | TGCTGTCGTT | GCTCATATTG | ATATTGACGC | TGCTGAACTT | 960 |
| GGCAAAATTG | TAAAACCGA | TATTCCAATC | CTTTCTGATT | TGAAAGCGGC | TTTAAGCAGA | 1020 |
| CTTTTGCAAT | TAAATAAGGT | CAGGACTGAC | TTTAATGATT | GGATTAAAAC | TGTCATTGAA | 1080 |
| AATAAAGAGA | AAGCACCATT | TACTTATGAG | CCCCAAAACC | ATGATATCCG | TCCACAGGAA | 1140 |
| ACAATTAAAT | TAATTGGAGA | ATACACTCAA | GGAGATGCAA | TCATTGTAAC | TGACGTTGGG | 1200 |
| CAACATCAAA | TGTGGGTGGC | GCAATATTAT | CCTTATAAAA | ATGCAAGGCA | ACTTATTACT | 1260 |
| TCTGGGGGAA | TGGGAACGAT | GGGCTTTGGC | ATTCCTGCAG | CAATCGGTGC | AAAGCTGGCA | 1320 |
| CAGCCAAATA | AAAATGTCAT | TGTTTTTGTT | GGCGATGGTG | GCTTTCAAAT | GACTAATCAA | 1380 |
| GAATTAGCAT | TACTTAATGG | CTACGGTATT | GCAATCAAAG | TTGTGCTGAT | TAATAATCAT | 1440 |
| TCATTGGGAA | TGGTACGTCA | ATGGCAAGAA | TCATTCTATG | AAGAGCGACG | TTCACAATCG | 1500 |
| GTTTTTGATG | TTGAACCCAA | TTTTCAATTG | TTAGCCGAAG | CTTATGGCAT | CAAACATGTT | 1560 |
| AAGTTAGATA | ATCCAAAAAC | TTTGGCTGAT | GATTTAAAAA | TTATTACAGA | AGATGAGCCA | 1620 |
| ATGCTTATTG | AAGTTCTAAT | TTCAAAATCT | GAGCATGTTT | TACCAATGAT | ACCAGCTGGA | 1680 |

```
TTACACAATG  ACGAAATGAT  TGGACTTCAT  TTTACTGATA  AGAATGAGGA  GATAGATAAT     1740

GCGTAGAATG  ATTATCGCAA  AACTTCATAA  CGTGACAGGA  ATTATGAATC  GATTTACCGC     1800

CGTTCTCAAT  CGAAGGCAAG  TGAACATTCT  CTCAATTACC  GCTGGAGTTA  CAGAAAGTCA     1860

AGACTTAACT  CATACCACTT  TTGTTATTGA  AGTTGATCAT  CTTGATGAAG  TAGAACAAAT     1920

CATTAAACAA  TTAAATCGCT  TAATAGATGT  AATTGAAGTA  GCTGATATTA  CTGATTTTCC     1980

TCATGTAGAA  CGTGAAGTCG  TCTTGATTAA  AGTATCAGCT  CCACCGACCA  TTAGGGCAGA     2040

AATTTTTACA  ATGATTGAAC  CTTTTAGAGT  AAATGTAGTT  GATGTCAATC  TGGAAAATGT     2100

CACCATTCAA  TTAACGGGTG  ATTCAGCAAA  AATCGAAGCA  CTTATTGAGG  TTGTTAGTCC     2160

TTATGGCATT  CTAAATATGG  CTCGGACAGG  TAGTGCAGGT  TTTGAGCGTG  GCTAAATTTA     2220

AATAAGTTAA  C                                                              2231
```

( 2 ) INFORMATION FOR SEQ ID NO: 15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 15:

```
CTAGTGAAGG  TTGCGTTACA                                                       20
```

( 2 ) INFORMATION FOR SEQ ID NO: 16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: YES ( x i ) SEQUENCE DESCRIPTION: SEQ ID NO: 16:

```
TGCCATTTTT  GTTTCCTCTA                                                       20
```